(12) United States Patent
Lamprecht et al.

(10) Patent No.: US 11,369,677 B2
(45) Date of Patent: Jun. 28, 2022

(54) USE OF NANOPARTICLES FOR IMMUNOTHERAPY

(71) Applicant: Alf Lamprecht, Wesseling (DE)

(72) Inventors: Alf Lamprecht, Wesseling (DE); Maryam Shetab Boushehri, Leverkusen (DE)

( * ) Notice: Subject to any disclaimer, the term of this patent is extended or adjusted under 35 U.S.C. 154(b) by 0 days.

(21) Appl. No.: 16/482,125

(22) PCT Filed: Jan. 31, 2018

(86) PCT No.: PCT/EP2018/052433
§ 371 (c)(1),
(2) Date: Jul. 30, 2019

(87) PCT Pub. No.: WO2018/141810
PCT Pub. Date: Aug. 9, 2018

(65) Prior Publication Data
US 2019/0351053 A1    Nov. 21, 2019

(30) Foreign Application Priority Data

Jan. 31, 2017 (EP) ..................... 17154040

(51) Int. Cl.
| | | |
|---|---|---|
| *A61K 39/39* | (2006.01) | |
| *A61K 9/16* | (2006.01) | |
| *A61P 35/00* | (2006.01) | |
| *A61K 39/00* | (2006.01) | |

(52) U.S. Cl.
CPC ............ *A61K 39/39* (2013.01); *A61K 9/1635* (2013.01); *A61K 9/1647* (2013.01); *A61P 35/00* (2018.01); *A61K 2039/55561* (2013.01); *A61K 2039/55572* (2013.01)

(58) Field of Classification Search
CPC .......... A61K 2039/55561; A61K 2039/55572; A61K 39/39; A61K 9/1635; A61K 9/1647; A61P 35/00
See application file for complete search history.

(56) References Cited

U.S. PATENT DOCUMENTS

| | | | |
|---|---|---|---|
| 2003/0148976 A1 | 8/2003 | Krieg et al. | |
| 2013/0209368 A1* | 8/2013 | Magdassi | A61K 49/0056 424/9.6 |
| 2014/0220143 A1 | 8/2014 | Dhar et al. | |
| 2016/0030349 A1 | 2/2016 | Francis et al. | |

FOREIGN PATENT DOCUMENTS

| | | |
|---|---|---|
| WO | 2011/042542 | 4/2011 |
| WO | 2016/004290 | 1/2016 |

OTHER PUBLICATIONS

Google NPL search; downloaded May 14, 2020.*
IP.com NPL search; downloaded May 14, 2020.*
Dillen et al.; "Evaluation of ciprofloxacin-loaded Eudragit RS100 or RL100/PLGA nanoparticles"; International Journal of Pharmaceutics 314 (2006); pp. 72-82.*
Haron et al.; "Ciprofloxacin induces apoptosis and inhibits proliferation of human colorectal carcinoma cells"; British Journal of Cancer (2002) 86, pp. 443-448.*
Yadav et al.; "Eudragit-Based Nanosuspension of Poorly Water-Soluble Drug: Formulation and In Vitro-In Vivo Evaluation"; AAPS PharmSciTech, vol. 13, No. 4, Dec. 2012.*
Dillen et al.; "Evaluation of ciprofloxacin-loaded Eudragit RSI 00 or RL100/PLGA nanoparticles"; International Journal of Pharmaceutics 314 (2006); pp. 72-82.*
Herold et al.; "Ciprofloxacin induces apoptosis and inhibits proliferation of human colorectal carcinoma cells"; British Journal of W Cancer (2002) 86, pp. 443-448.*
Aisha et al.; "Development of Polymeric Nanoparticles of Garcinia mangostana Xanthones in Eudragit RL100/RS100 for Anti-Colon Cancer Drug delivery"; Journal of Nanomaterials, vol. 2015, Article ID 701979, 12 pages, published online Nov. 2015.*
Bousheri et al.; Biomaterials (166), pp. 1-12; published online Mar. 2, 2018.*
Fried et al.; "Lipopolysaccharide (LPS) Promotes Apoptosis in Human Breast Epithelial × Breast Cancer Hybrids, but Not in Parental Cells"; PLOS One; DOI:10.1371/journal.pone.0148438; pp. 1-19; published Feb. 10, 2016.*
Jahrsdorfer et al.; "CpG oligodeoxynucleotides as immunotherapy in cancer"; Update Cancer Ther. Mar. 2008 ; 3(1): 27-32.*
Kirtane et al.; "Exploiting Nanotechnology to Overcome Tumor Drug Resistance: Challenges and Opportunities"; Adv Drug Deliv Rev. Nov. 30, 2013.*
Moris et al.; "The Role of NSAIDs in Breast Cancer Prevention and Relapse: Current Evidence and Future Perspectives"; Breast Care 2016;11:339-344; published online Oct. 24, 2016.*
Ulbrich et al.; "Targeted drug-delivery approaches by nanoparticulate carriers in the therapy of inflammatory diseases"; J. R. Soc. Interface (2010) 7, S55-S66; published online Nov. 25, 2009.*
Varshosaz et al.; "Eudragit nanoparticles loaded with silybin: a detailed study of preparation, freeze-drying condition and in vitro/in vivo evaluation"; J Microencapsul, 2015; 32(3): 211-223; published online Dec. 30, 2014.*
International Search Report dated Mar. 21, 2018 in PCT/EP2018/052433.
Written Opinion dated Mar. 21, 2018 in PCT/EP2018/052433.
Handbook of Pharmaceutical Excipients, 5th edition, Pharmaceutical Press, 2006, pp. 553-560.
Liu et al., Bio-Protoc. 2013;3(17):e892-896 (4 pages).
*Polymers (Basel).* Sep. 1, 2011; 3(3): 1377-1397.
Evonik Industries AG, "EUDRAGIT® Polymers and PLASTOID® B," Technical Information, Jun. 2014, 4 pages.
Evonik Nutrition & Care GmbH, "Eudragit® Setting benchmarks in oral solid dosage forms since 1954," Brochure, 2015, 16 pages.

\* cited by examiner

*Primary Examiner* — Jeffrey T. Palenik
(74) *Attorney, Agent, or Firm* — Grüneberg and Myers PLLC

(57) ABSTRACT

A composition is for use as a medicament. The composition contains nanoparticles, wherein the nanoparticles contain a polymer selected from the group consisting of PLGA, PLA, PGA, PCL and poly(meth)acrylates, or a lipid. Further, the composition may contain nanoparticles made of a polymer selected from PLGA, amino alkyl methacrylate copolymers, methacrylic acid copolymers, methacrylic ester copolymers, and ammonio alkyl methacrylate copolymers.

16 Claims, 58 Drawing Sheets

Specification includes a Sequence Listing.

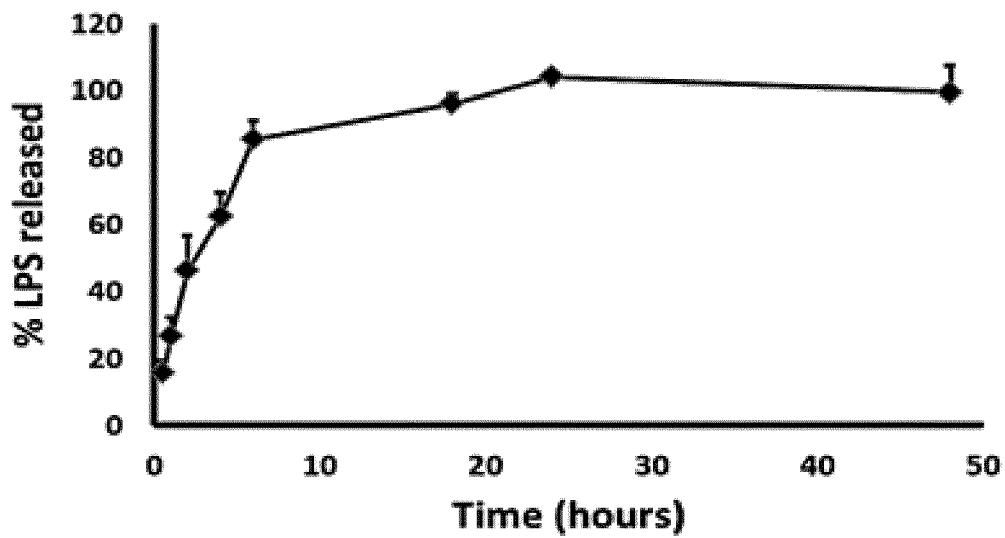
Fig. 2
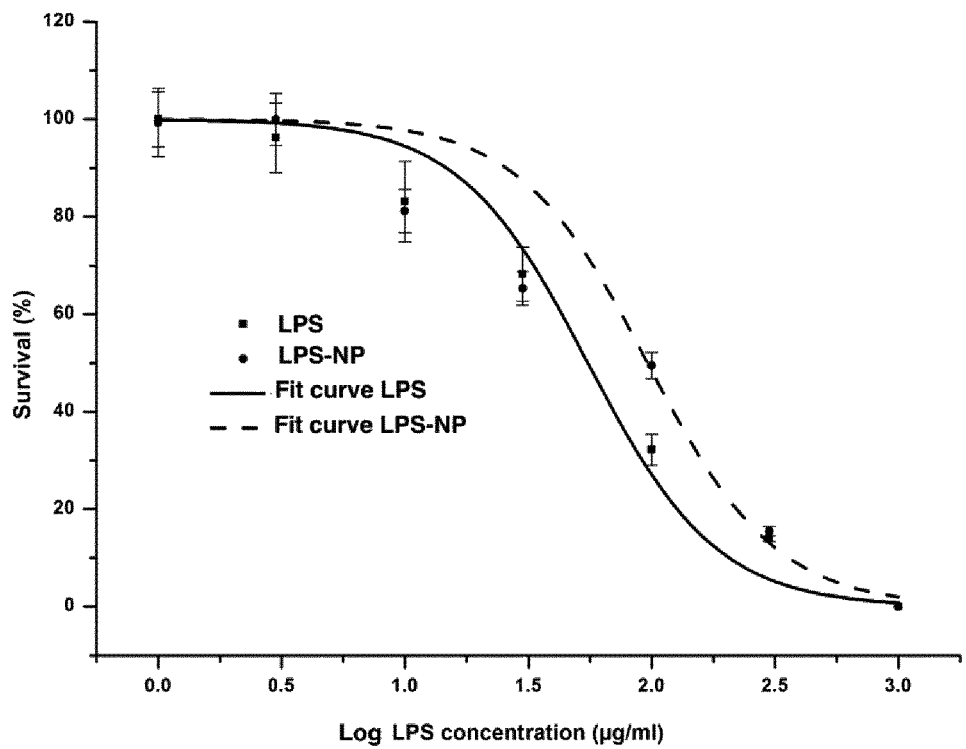
Fig. 3-A

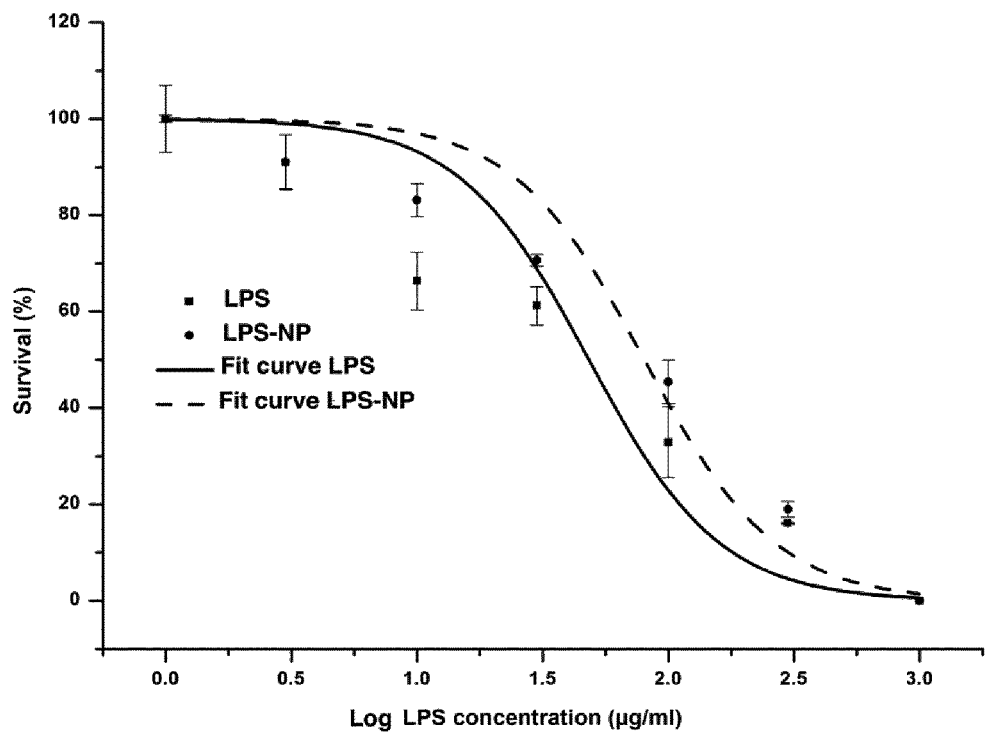
Figure 3-B
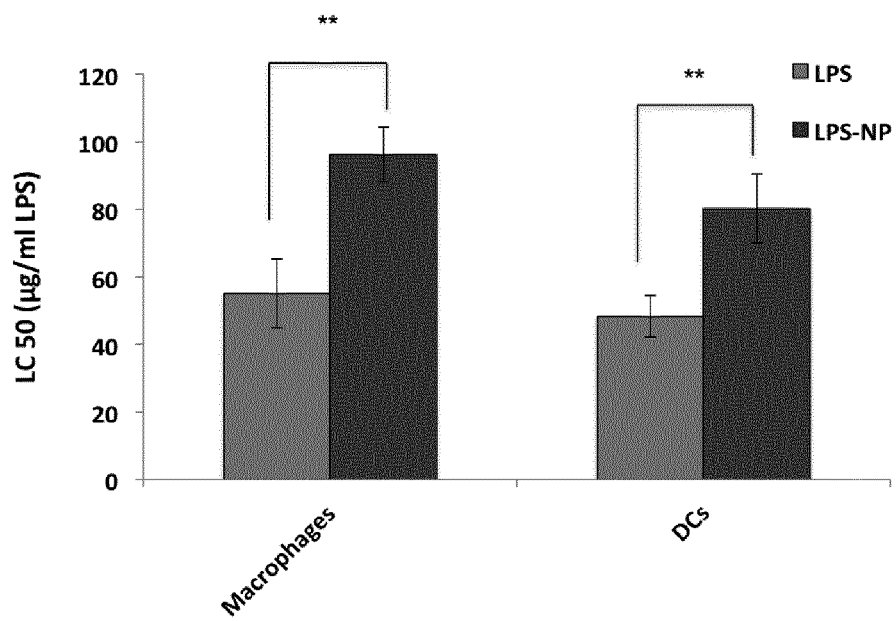
Fig. 3-C

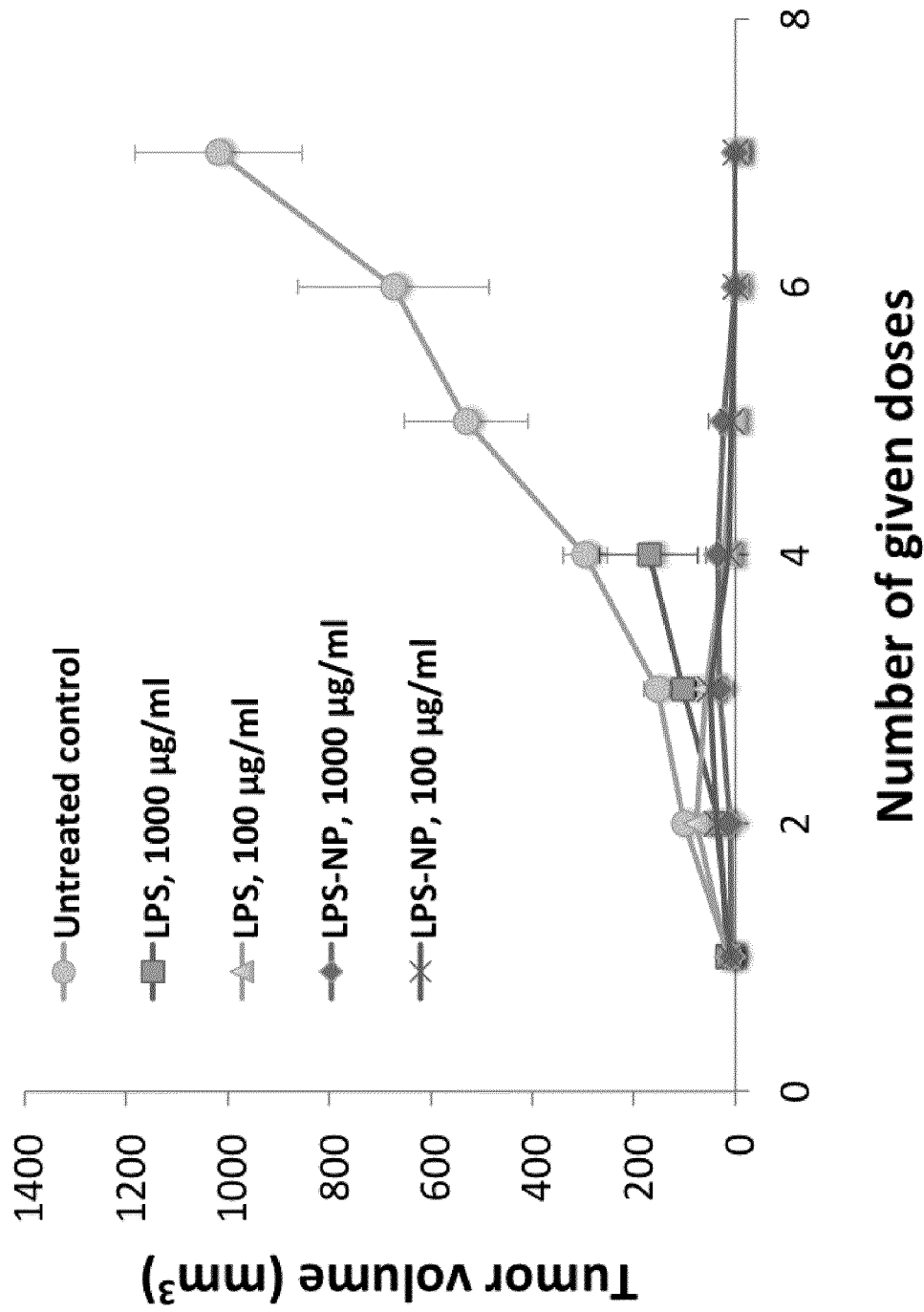
Fig. 5-A

Fig. 5-B

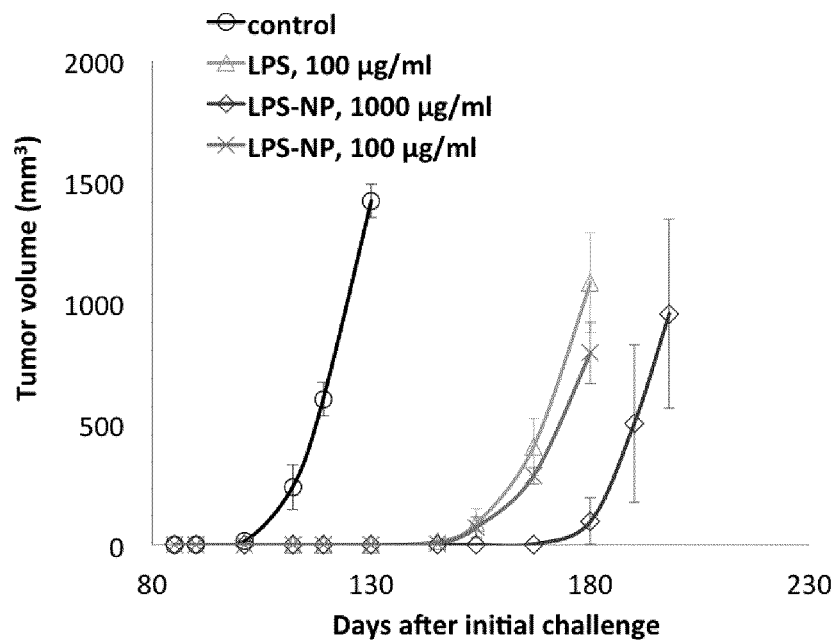
Fig. 5-C
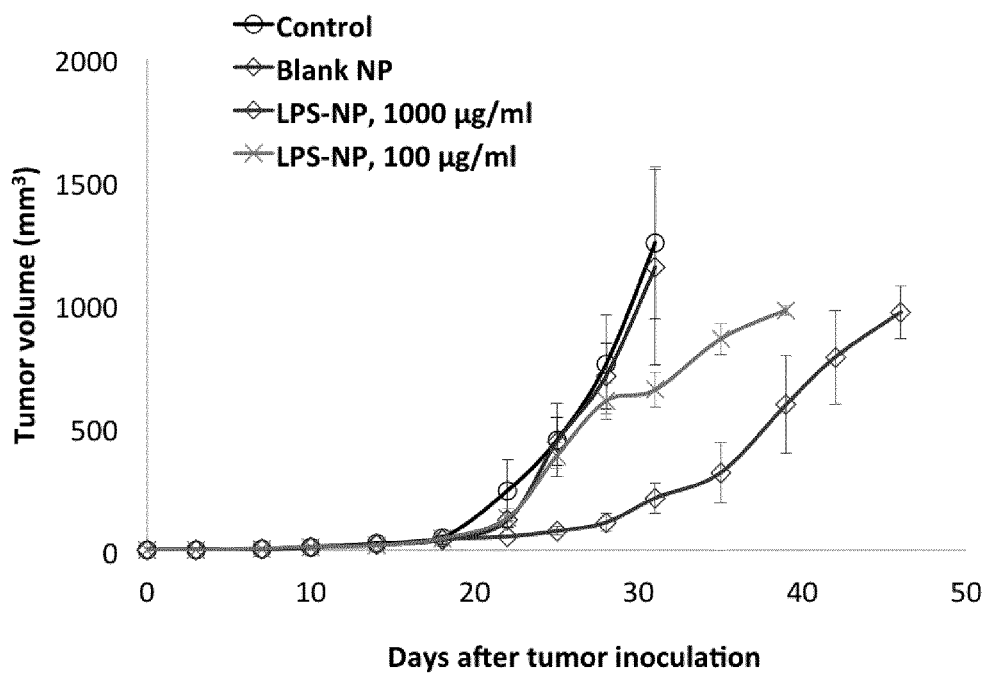
Fig. 5-D

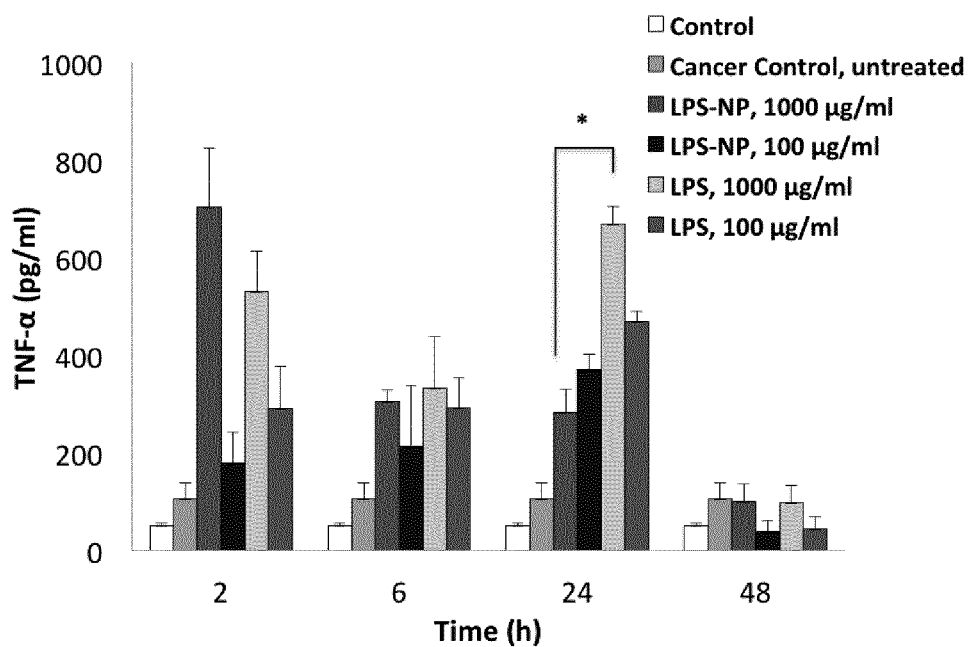
Fig. 6-A
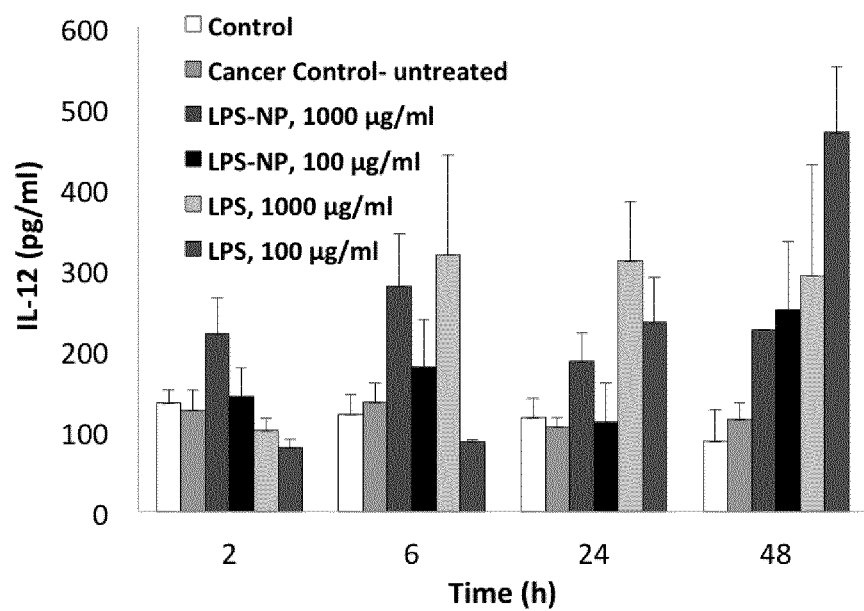
Fig. 6-B

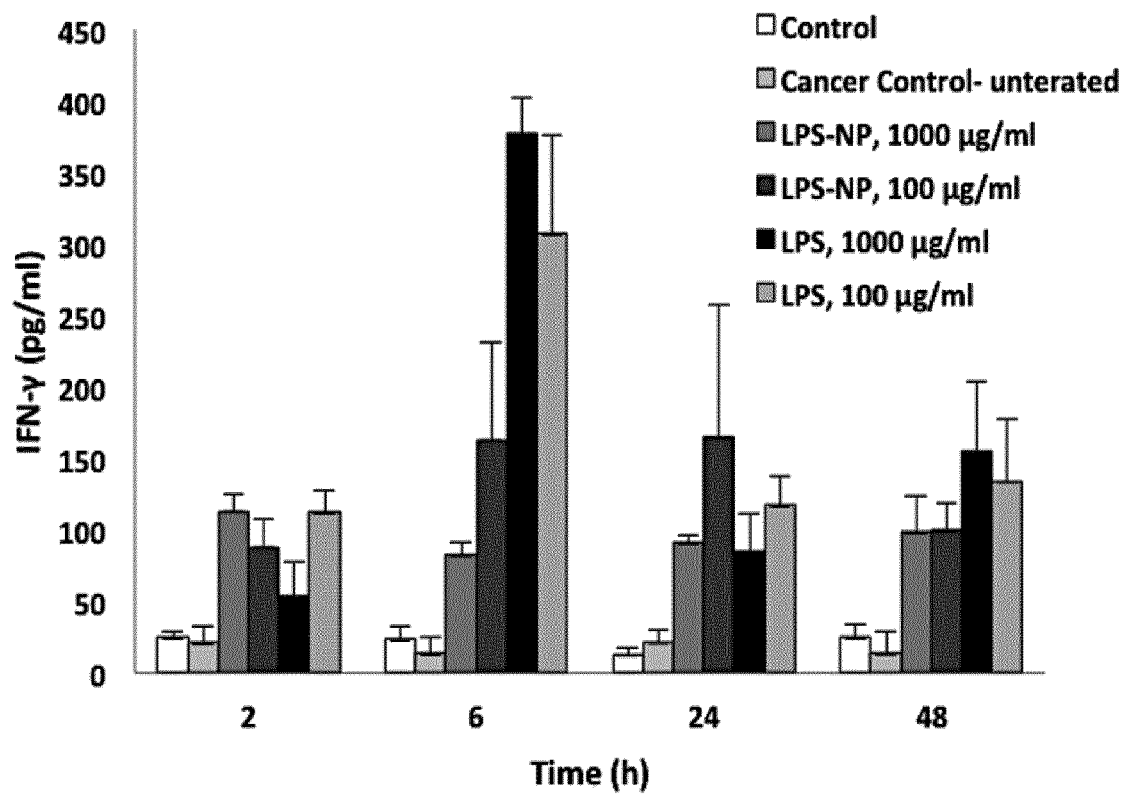
Fig. 6-C
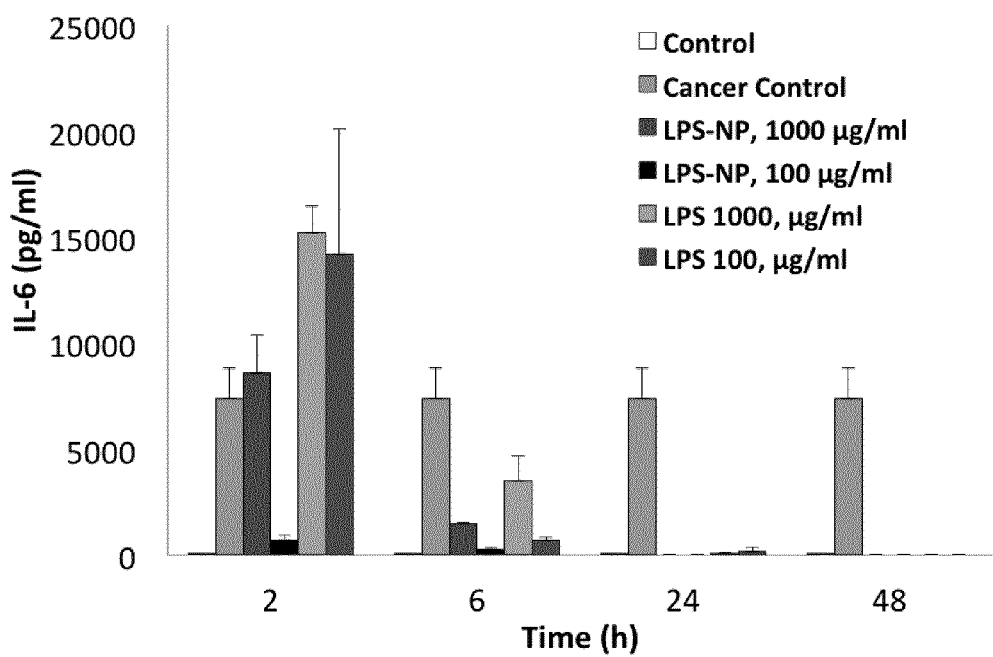
Fig. 6-D

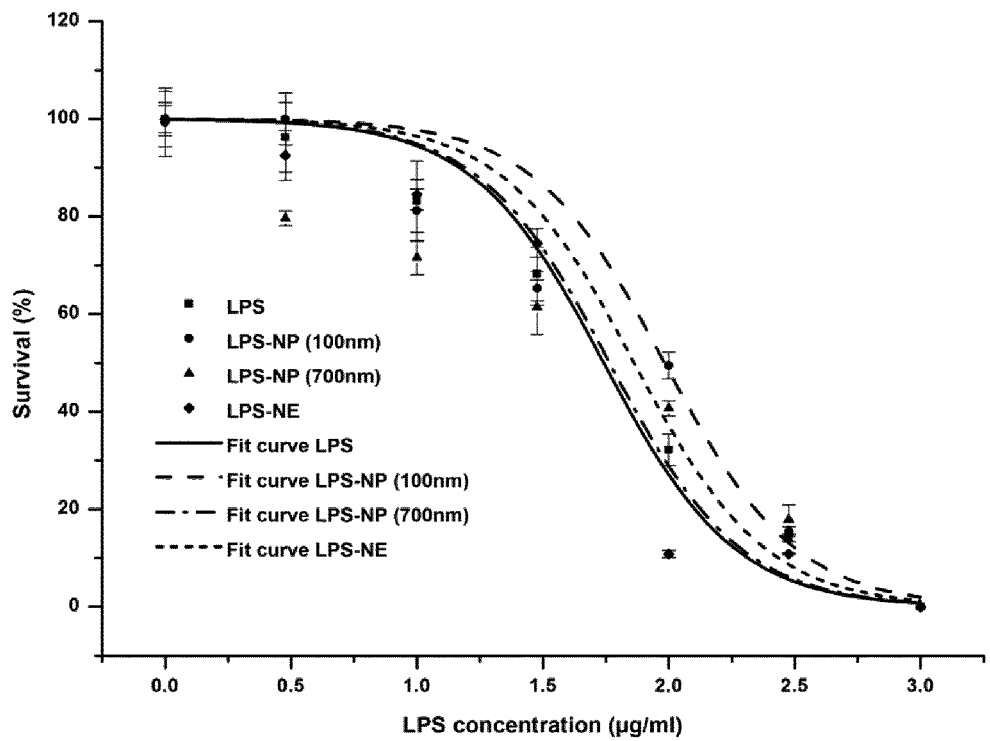
Fig. 9-A
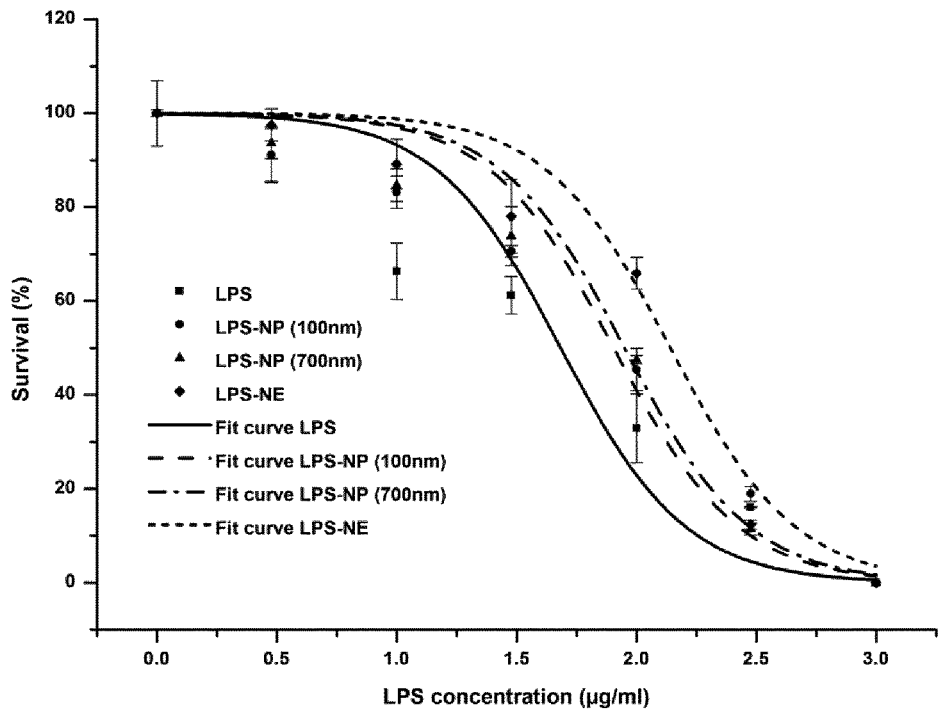
Fig. 9-B

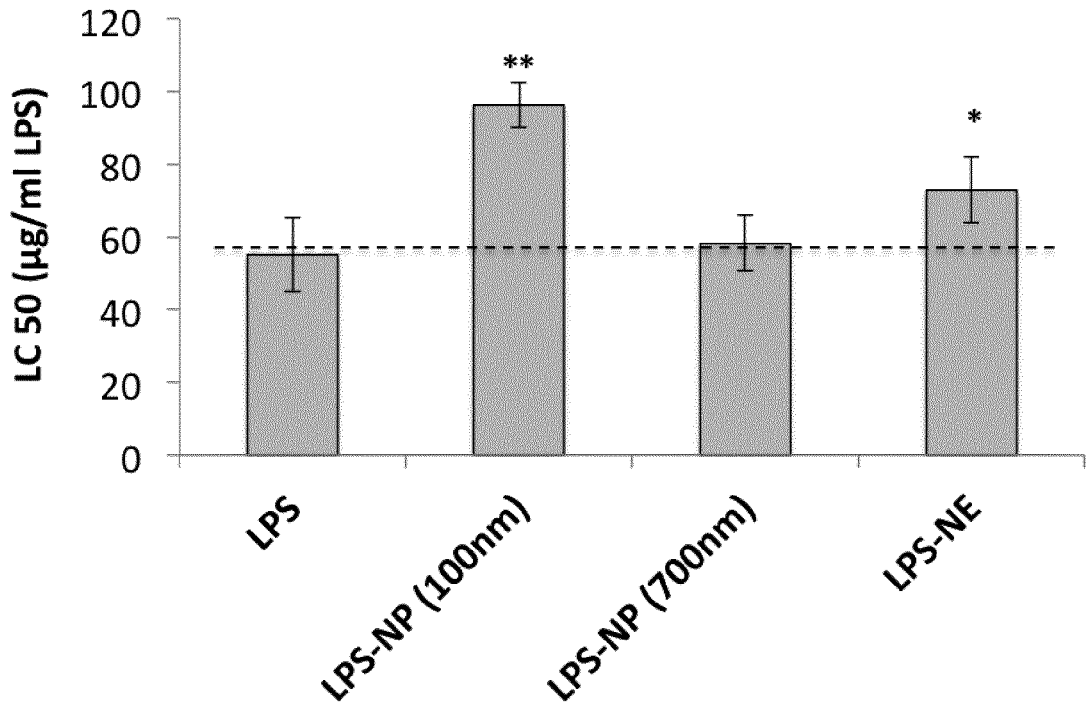
Fig. 9-C
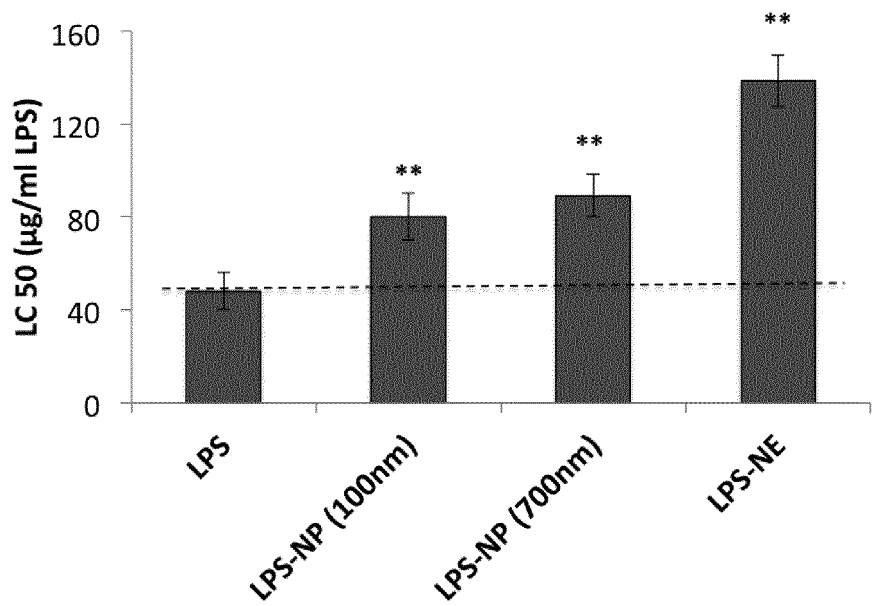
Fig. 9-D

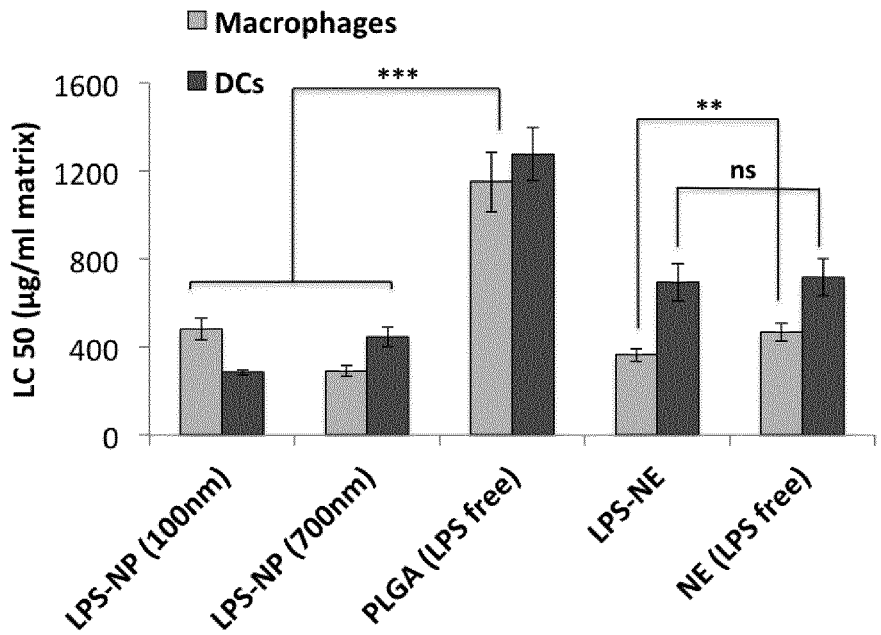
Fig. 9-E
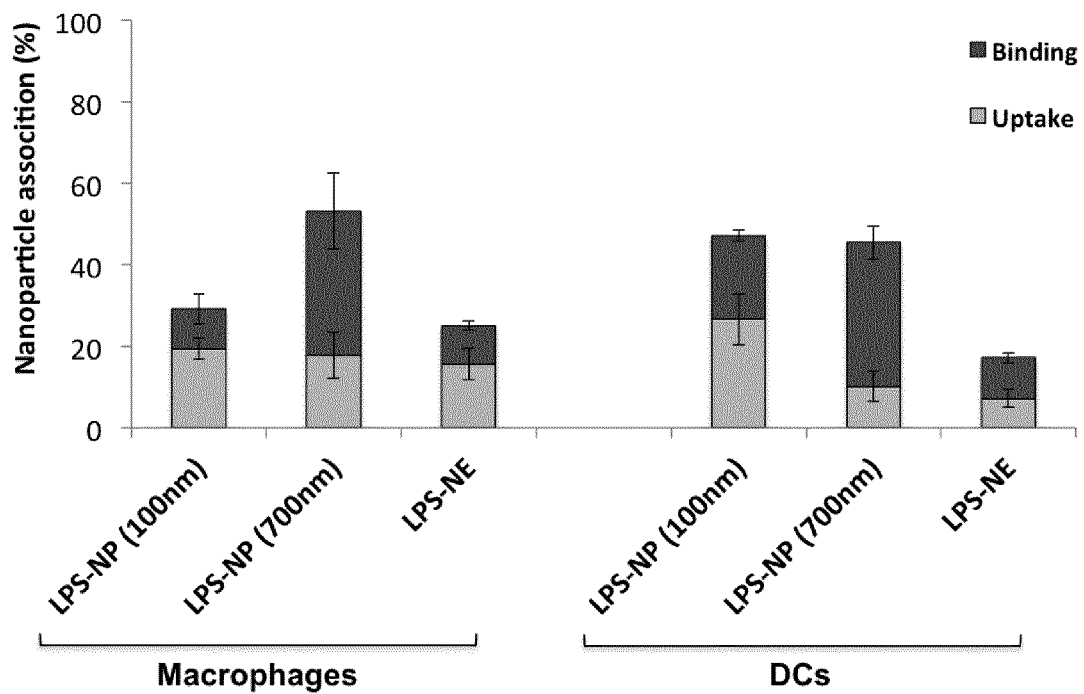
Fig. 10-A

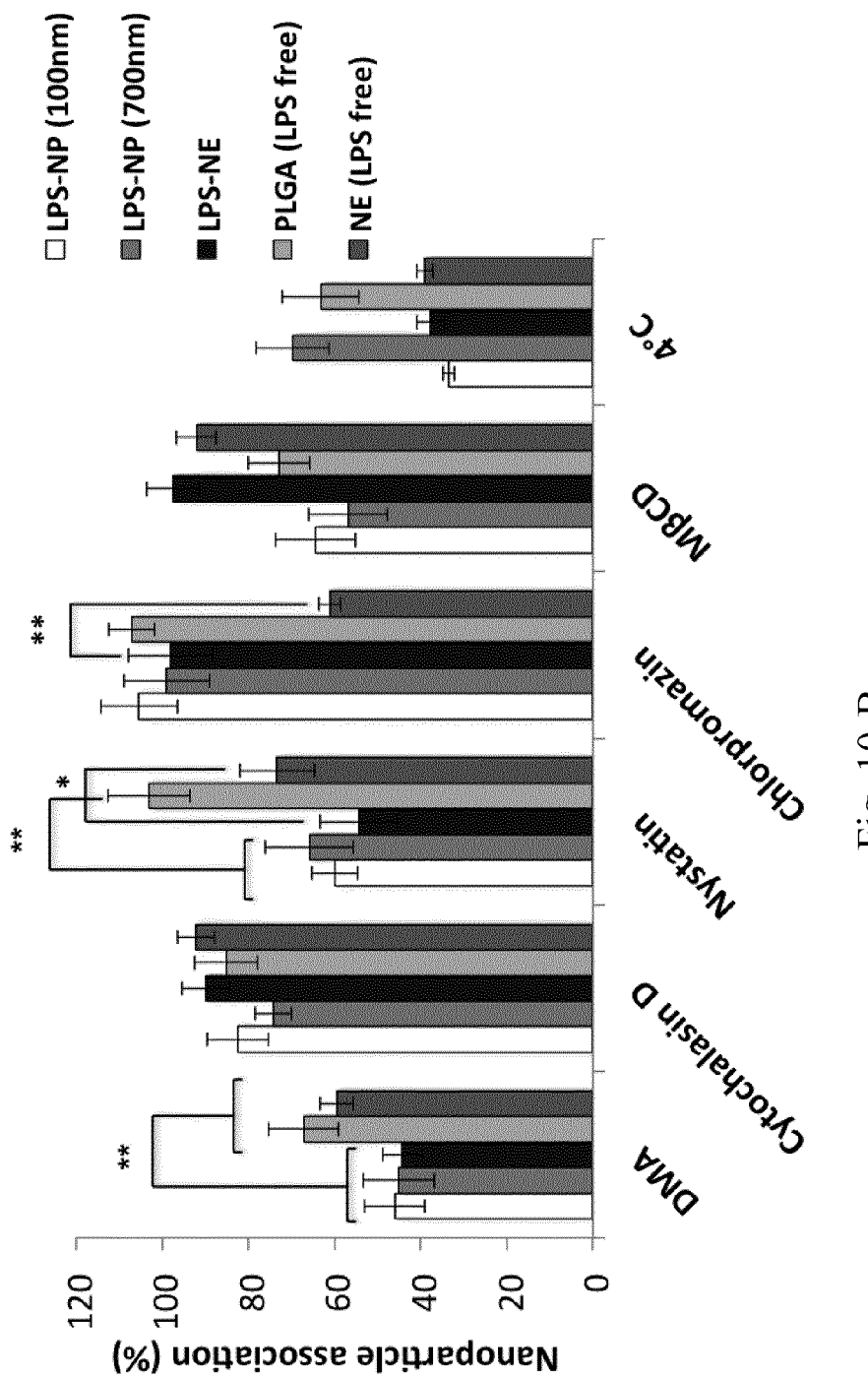
Fig. 10-B

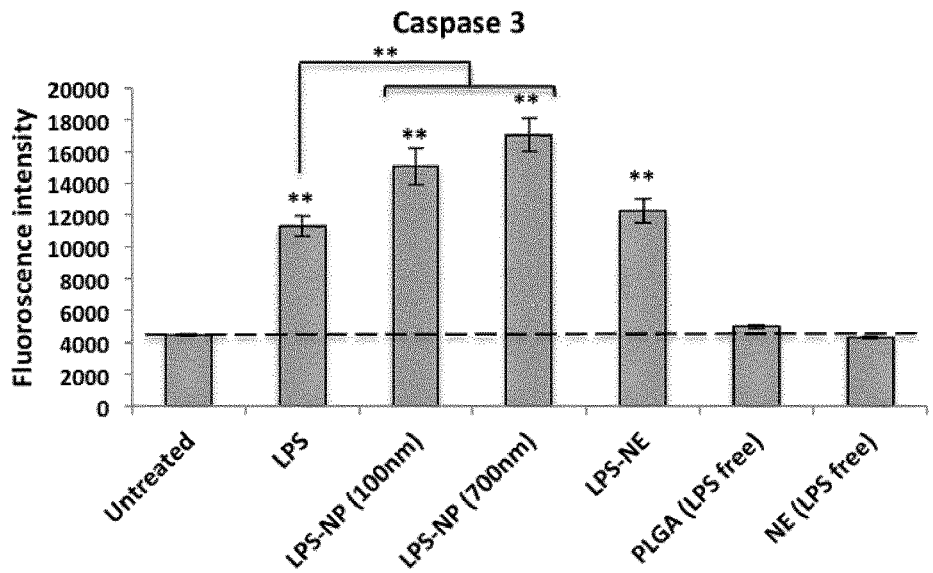
Fig. 11
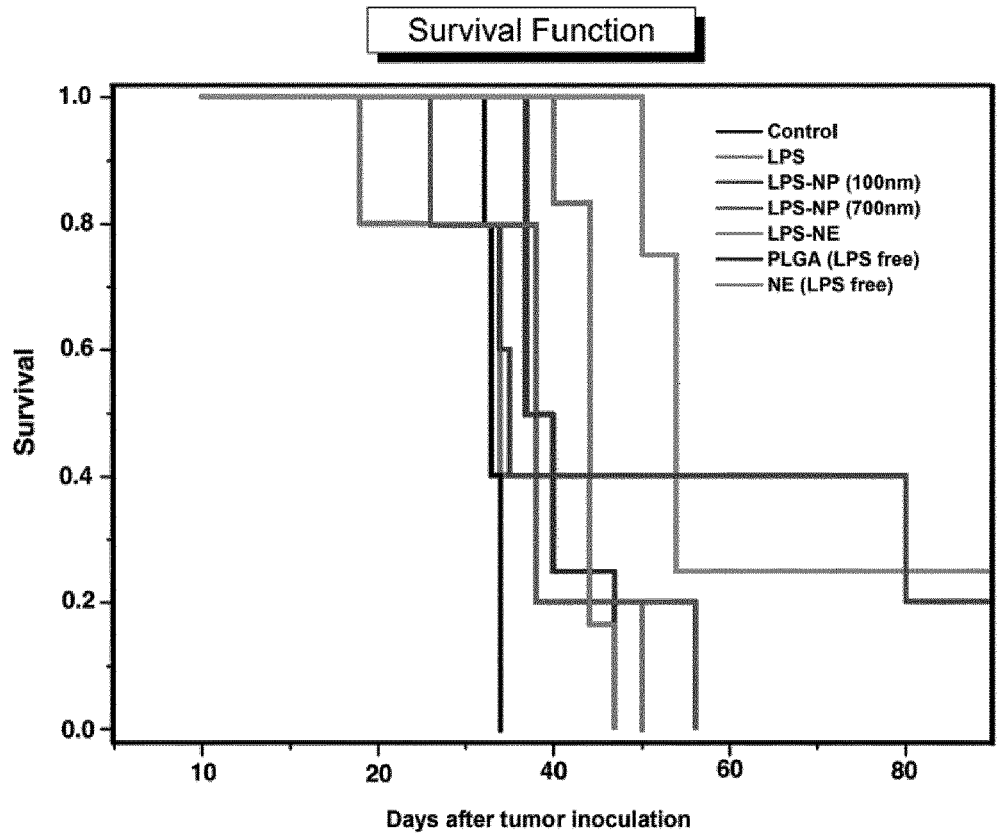
Fig. 12-A

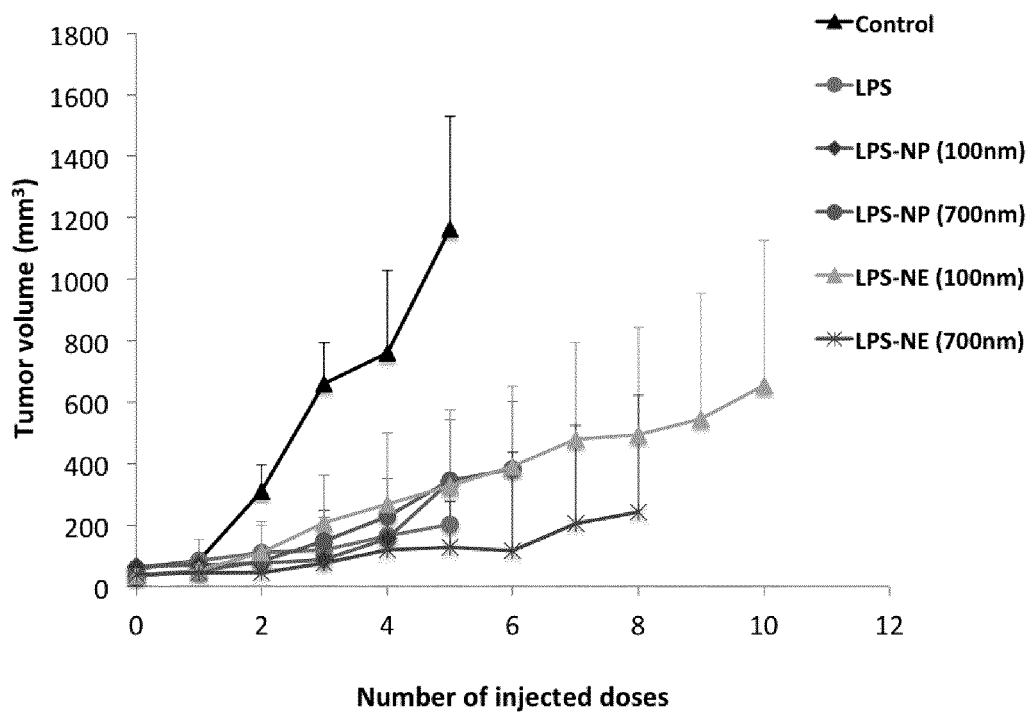
Fig. 12-B
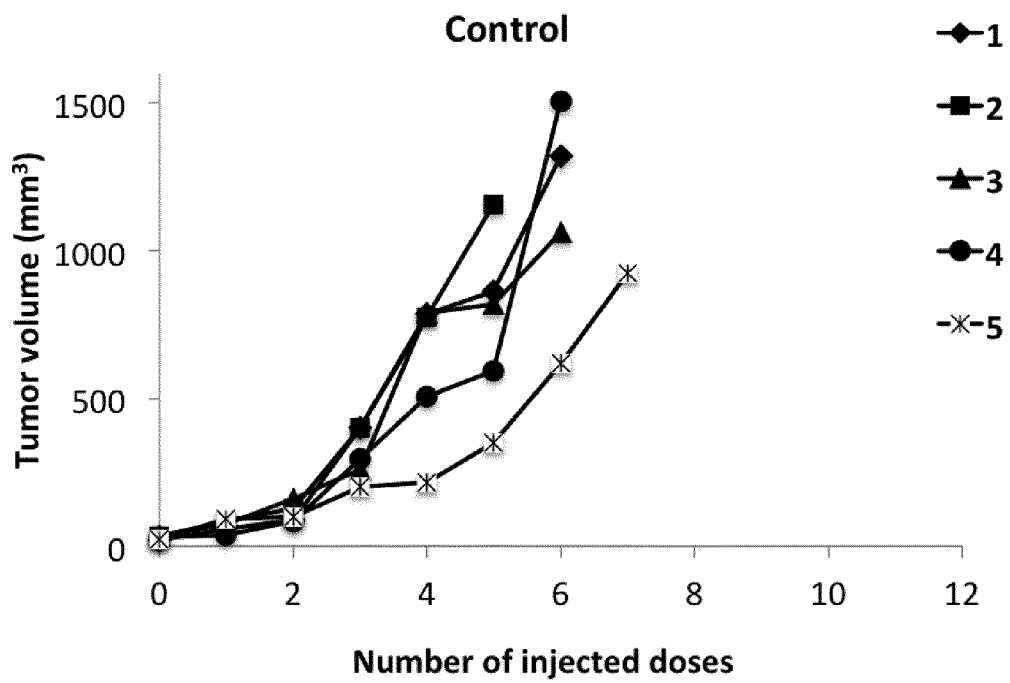
Fig. 13-A

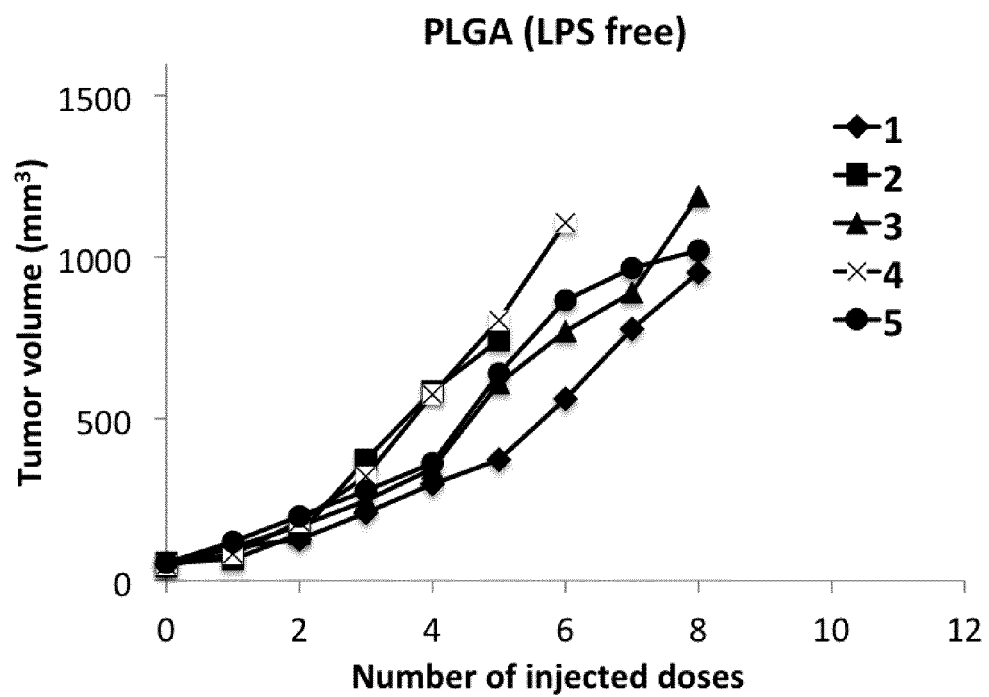
Fig. 13-B
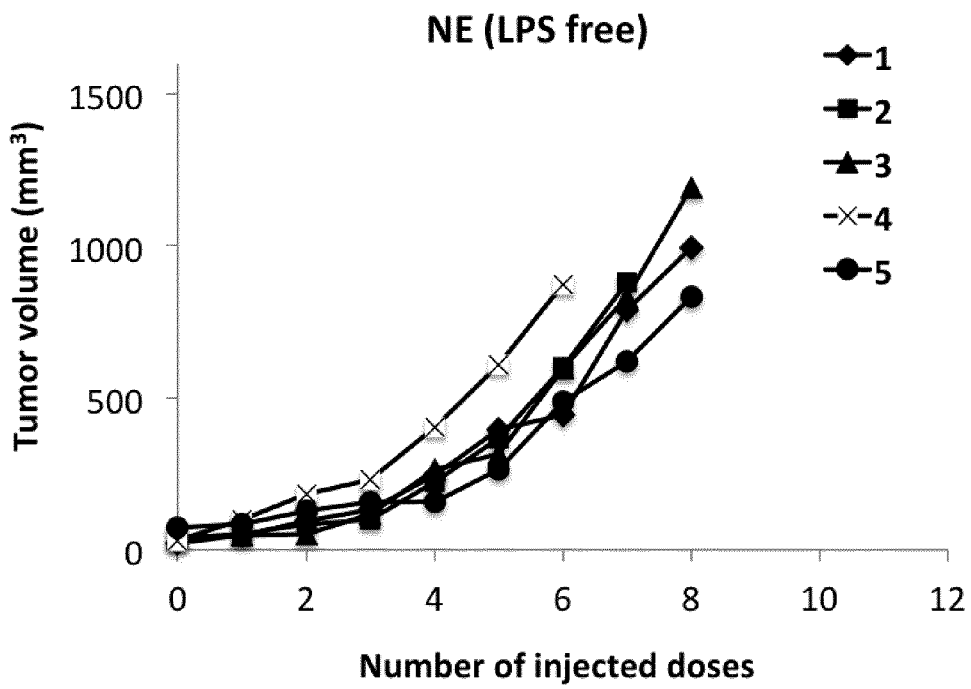
Fig. 13-C

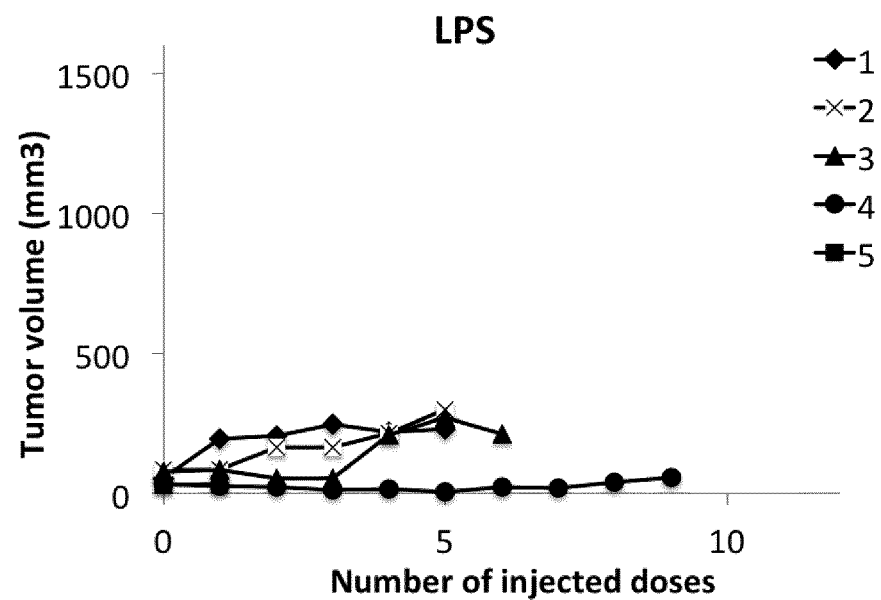
Fig. 13-D
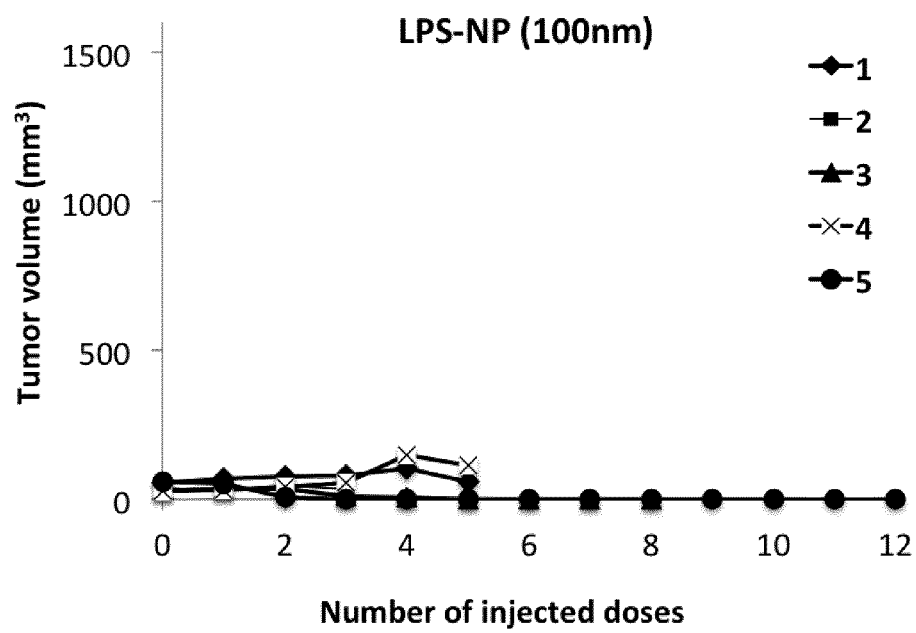
Fig. 13-E

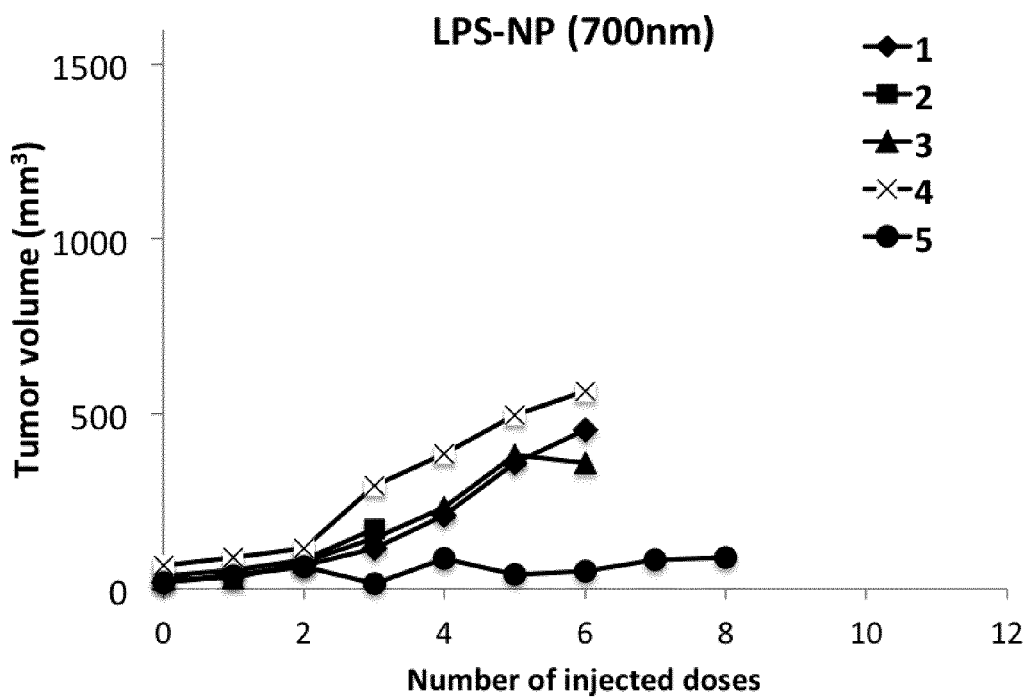
Fig. 13-F
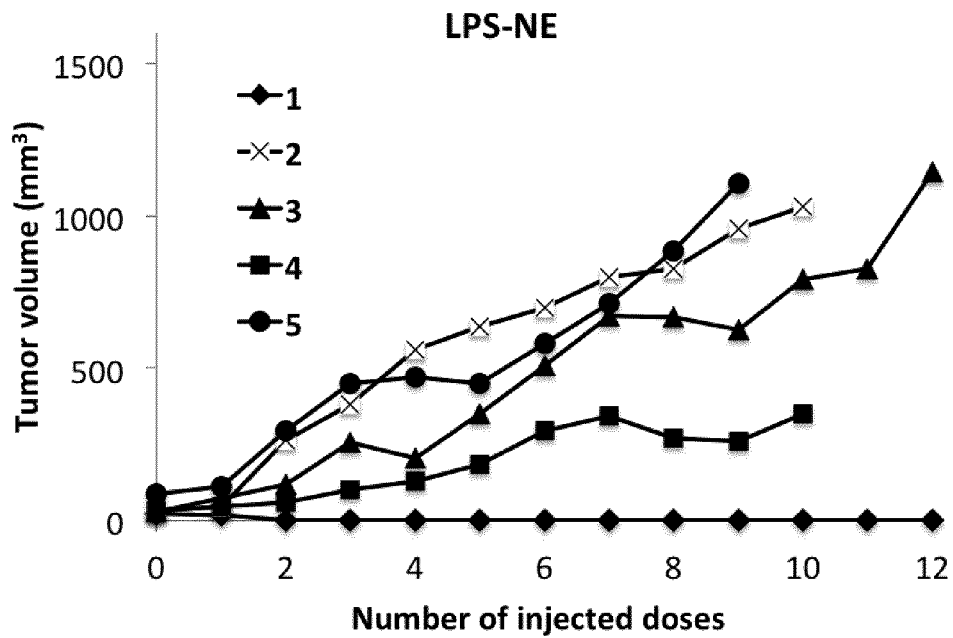
Fig. 13-G

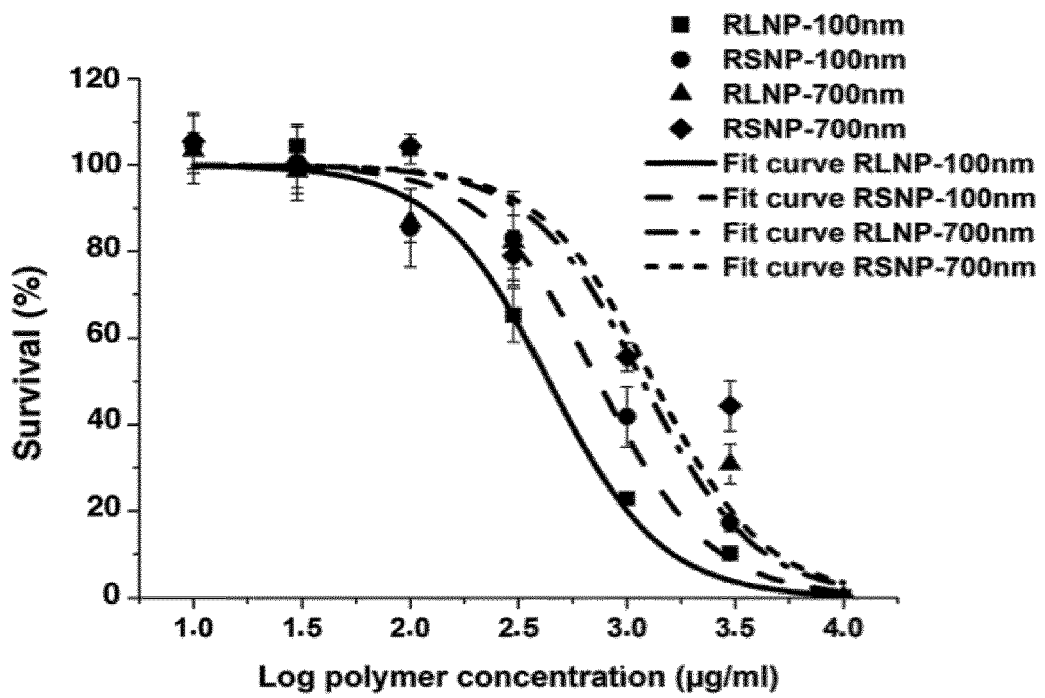
Fig. 15-A
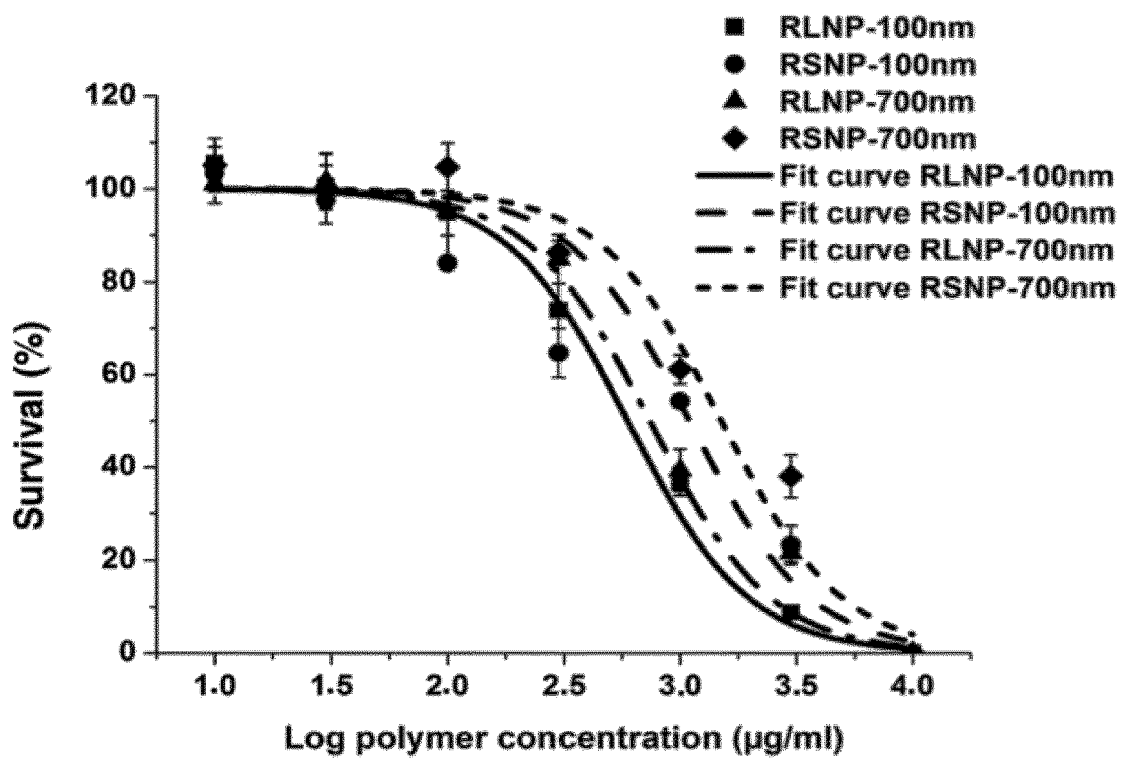
Fig. 15-B

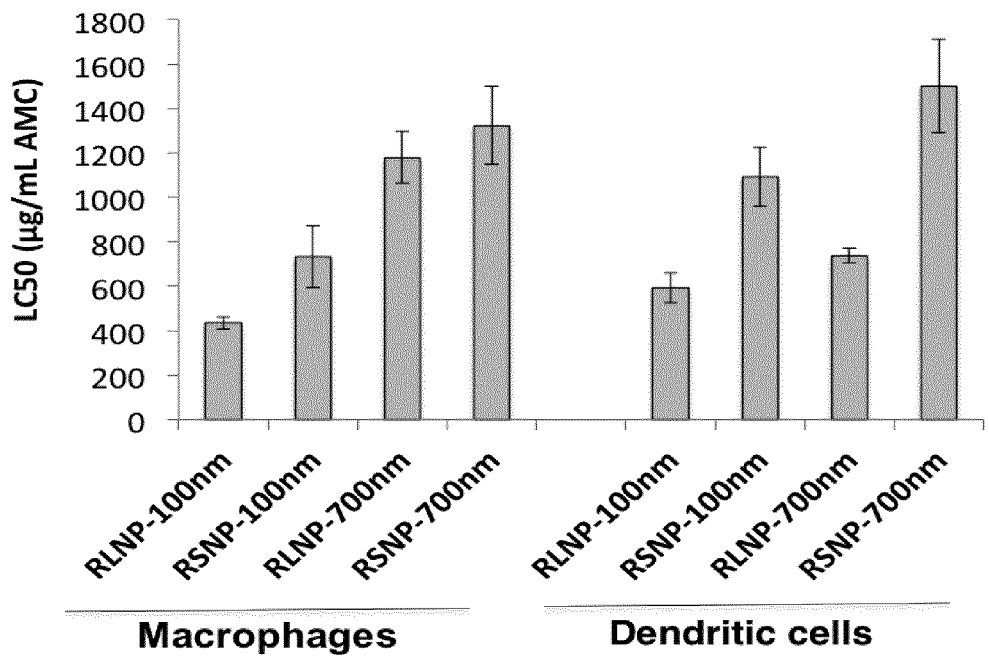
Fig. 15-C
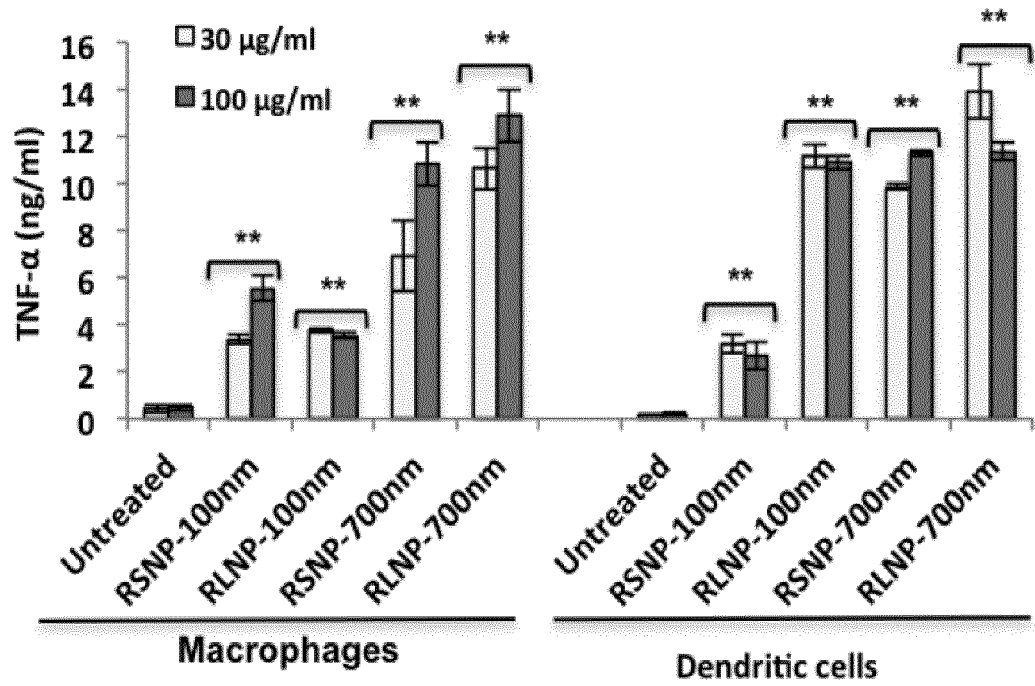
Fig. 16-A

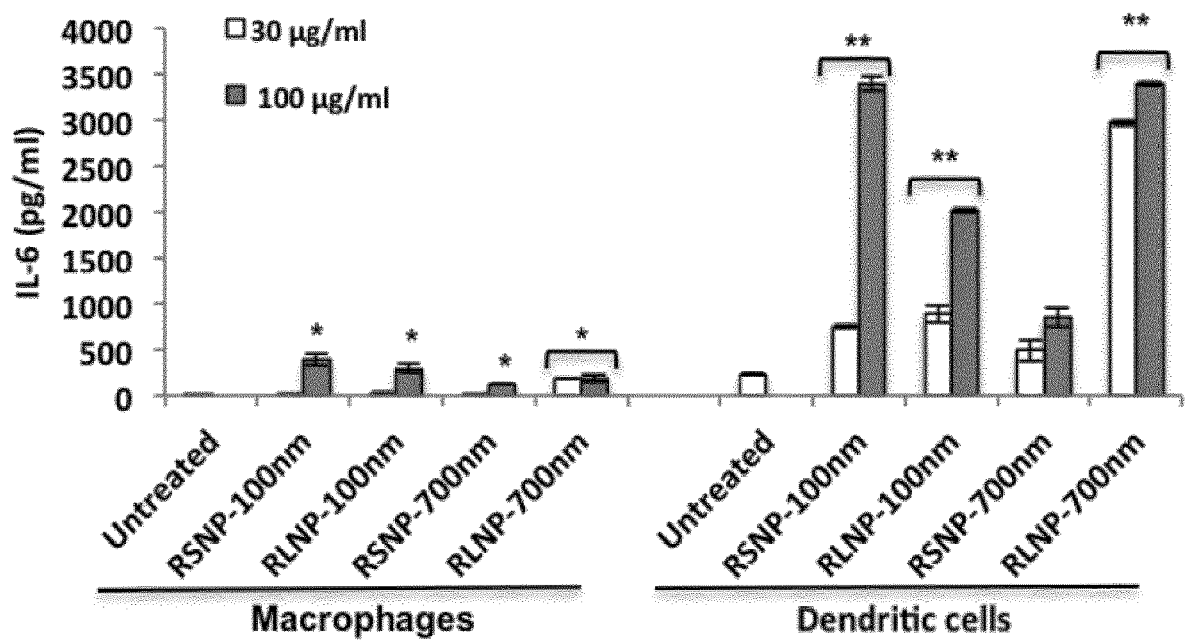
Fig. 16-B
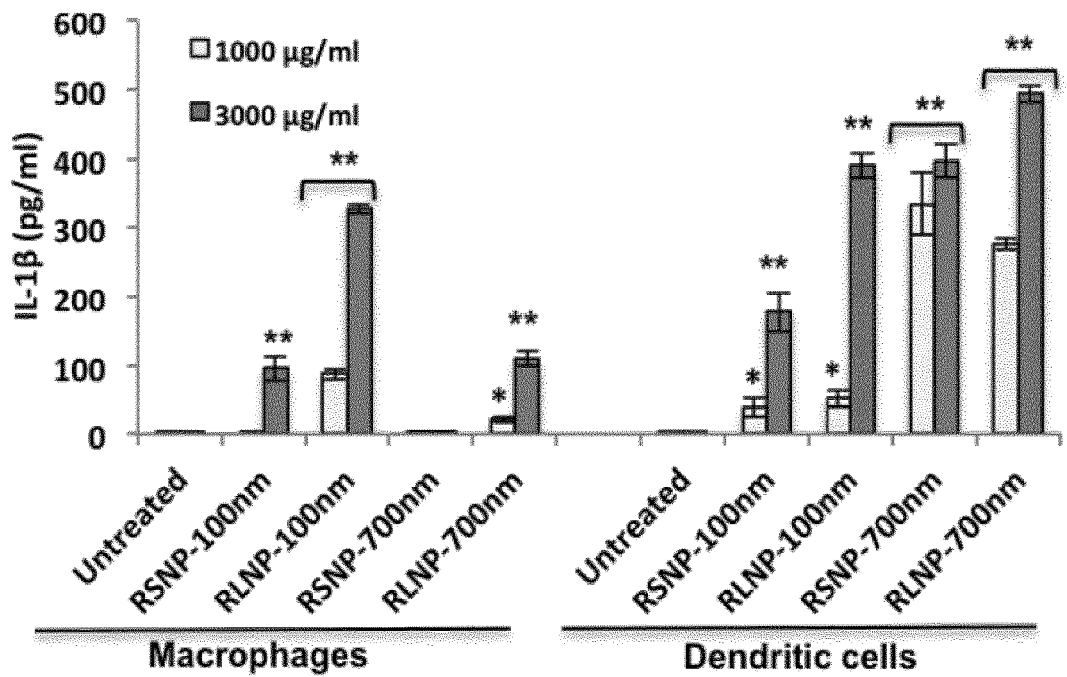
Fig. 16-C

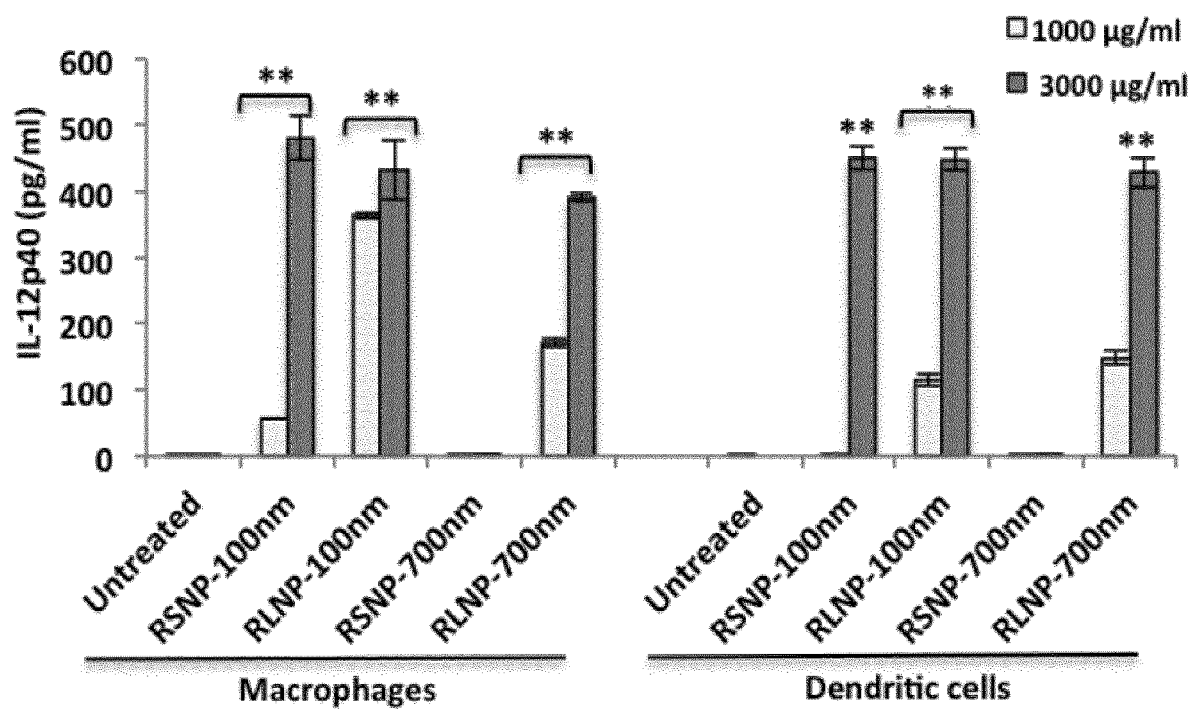
Fig. 16-D
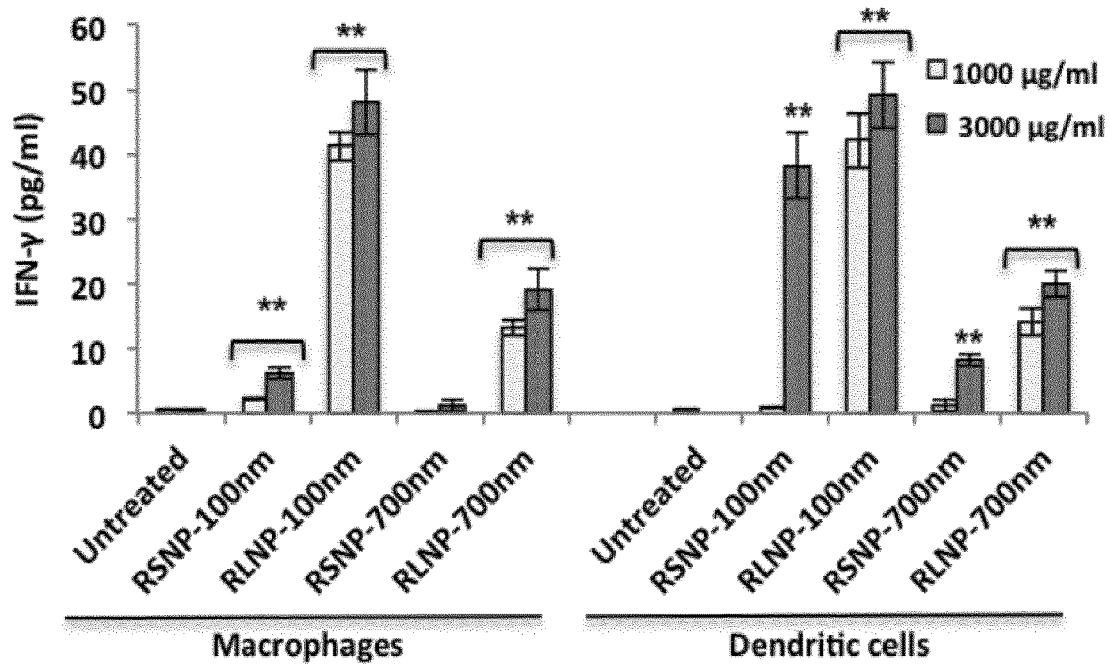
Fig. 16-E

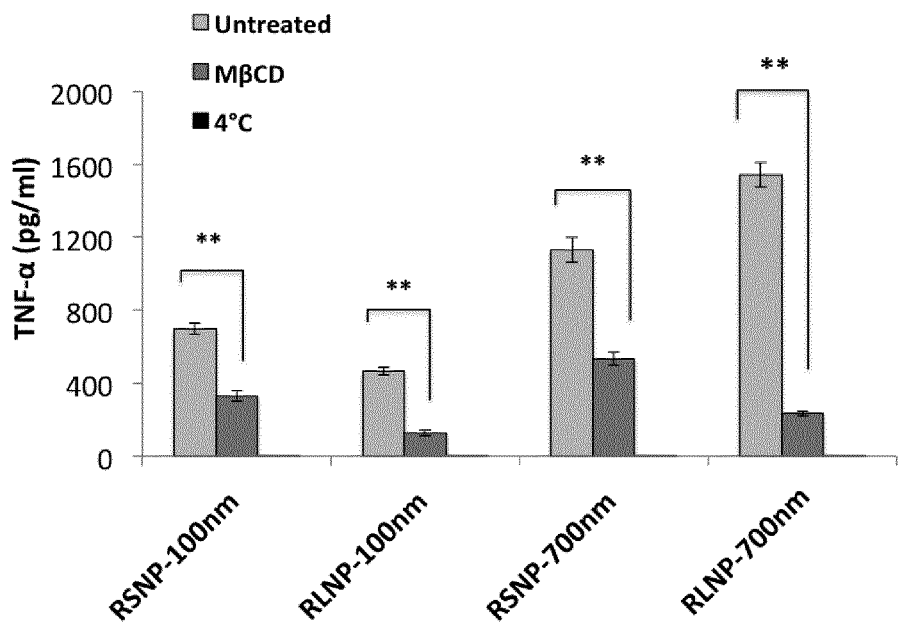
Fig. 16-F
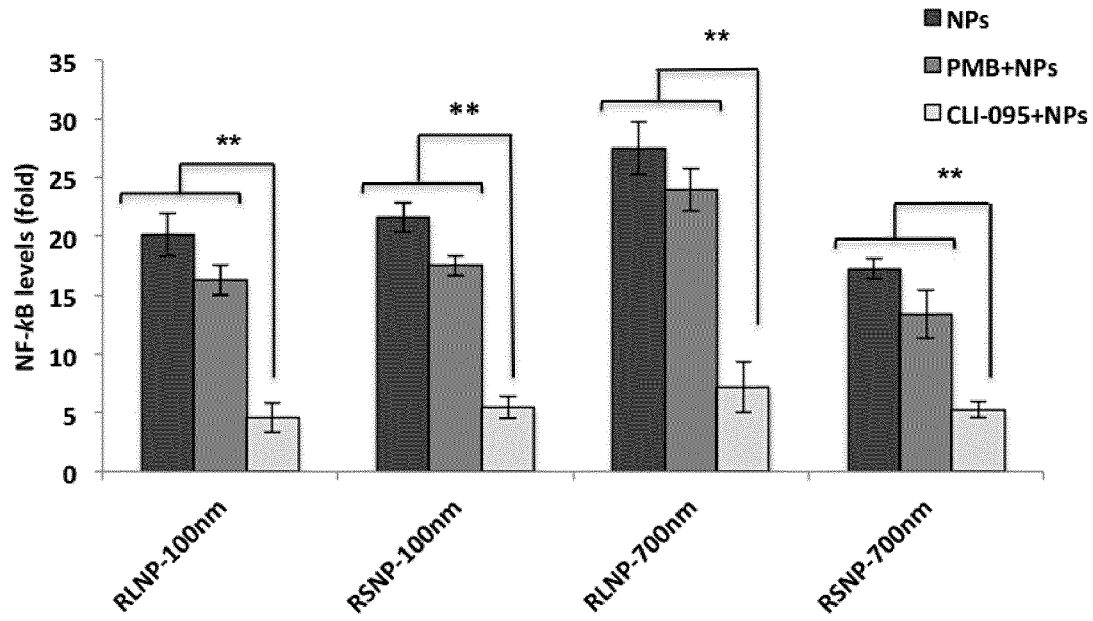
Fig. 17

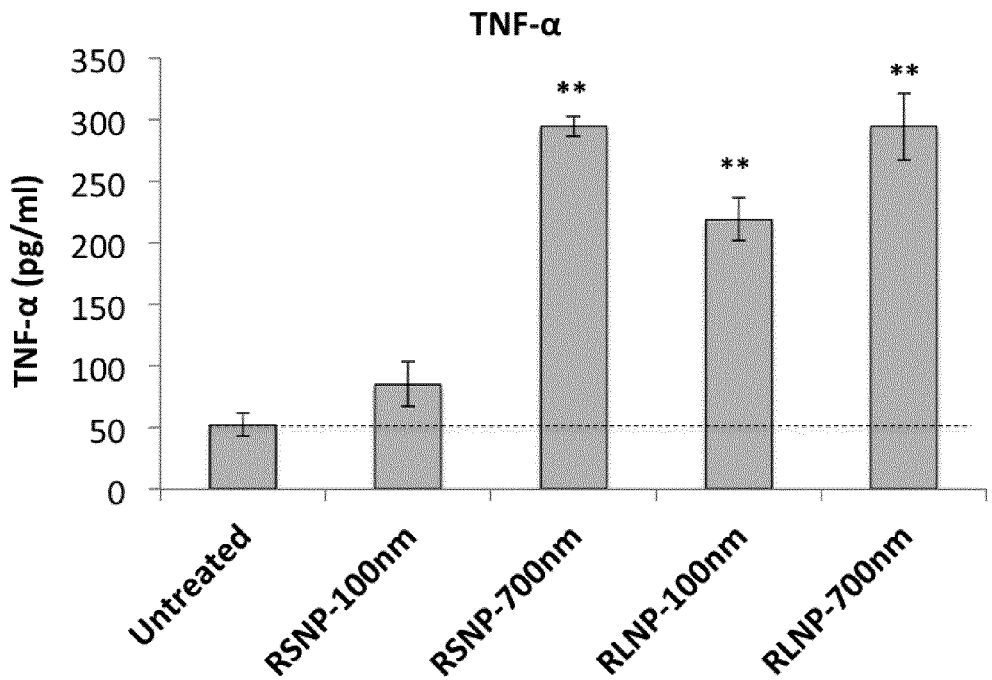
Fig. 18-A-1
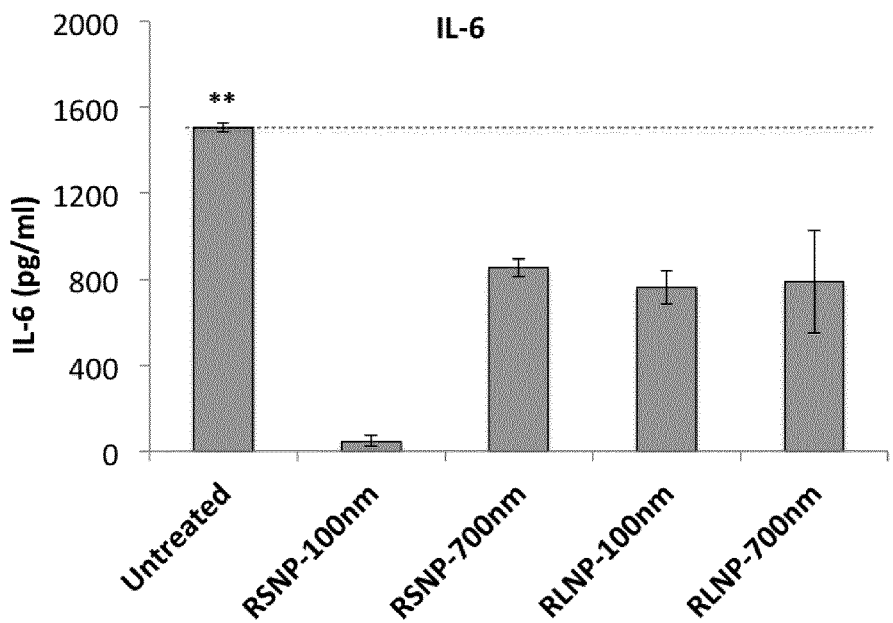
Fig. 18-A-2

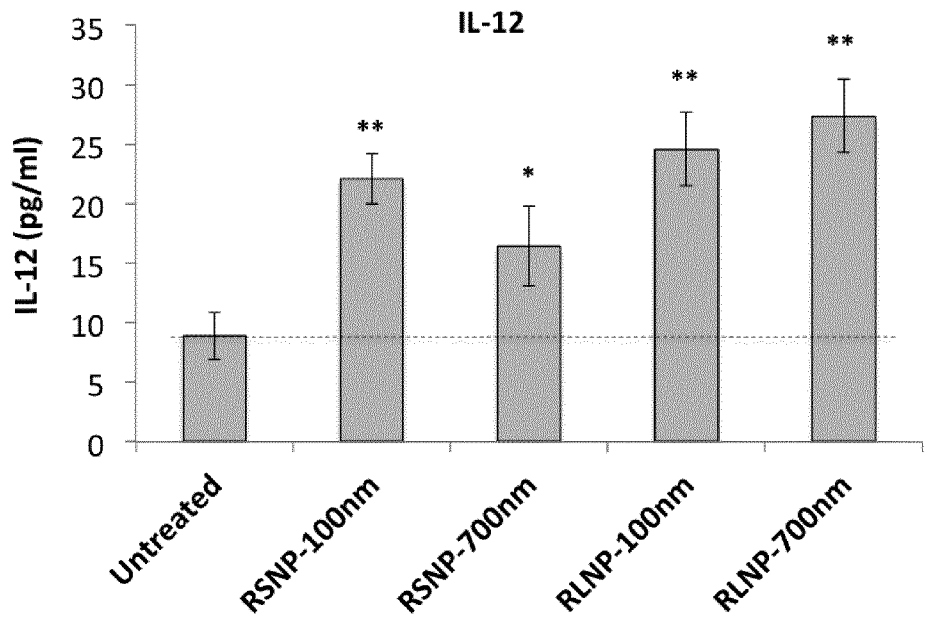
Fig. 18-A-3
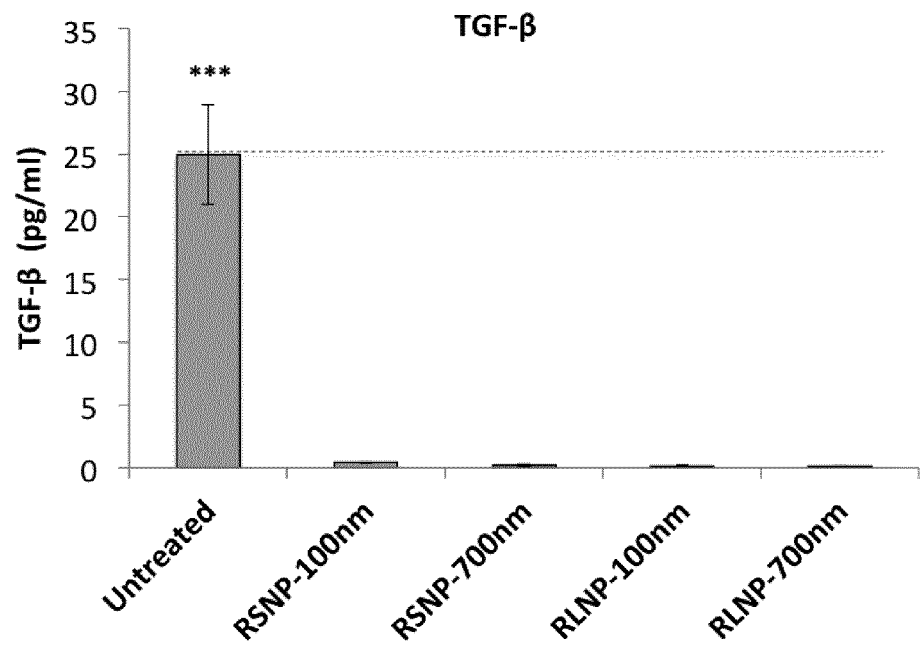
Fig. 18-A-4

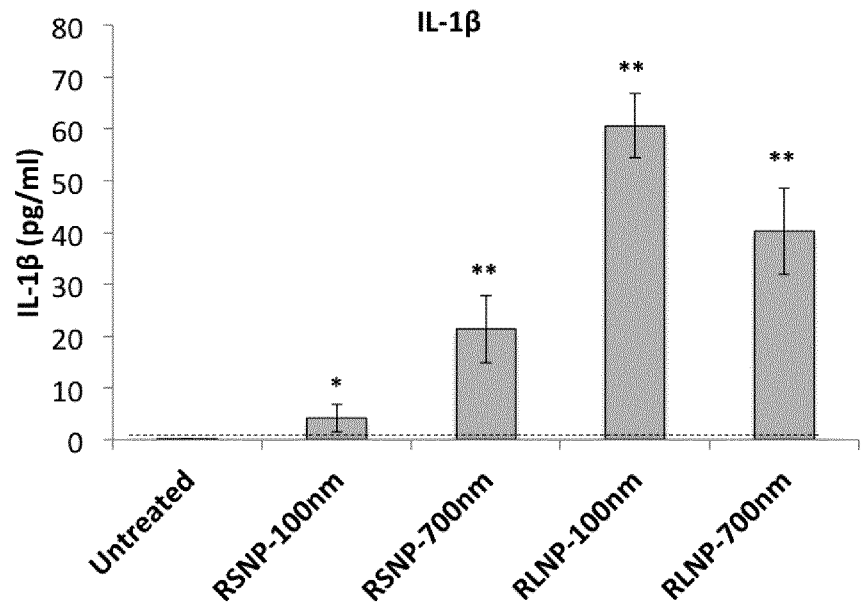
Fig. 18-A-5
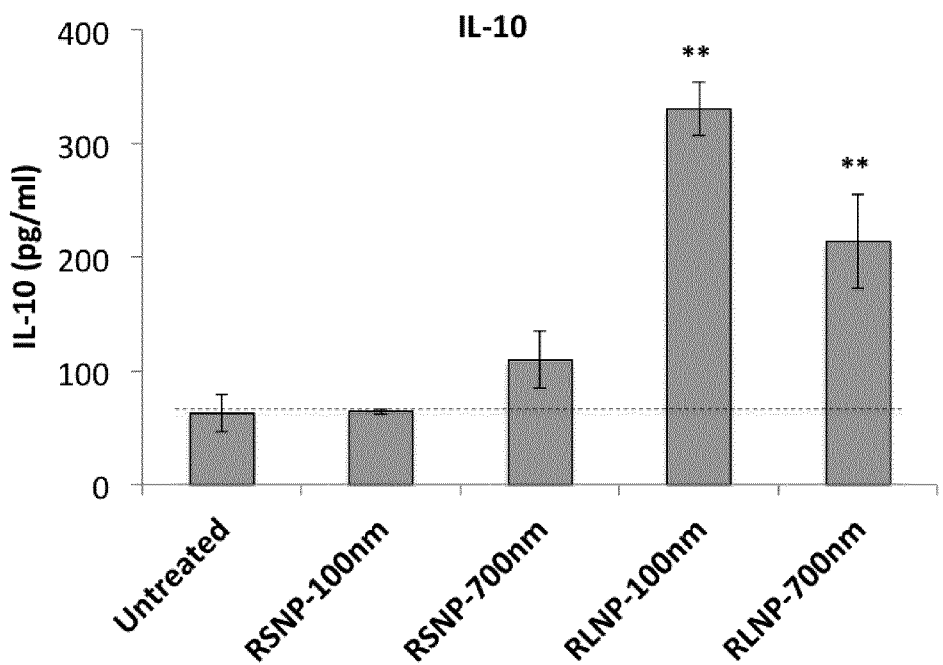
Fig. 18-A-6

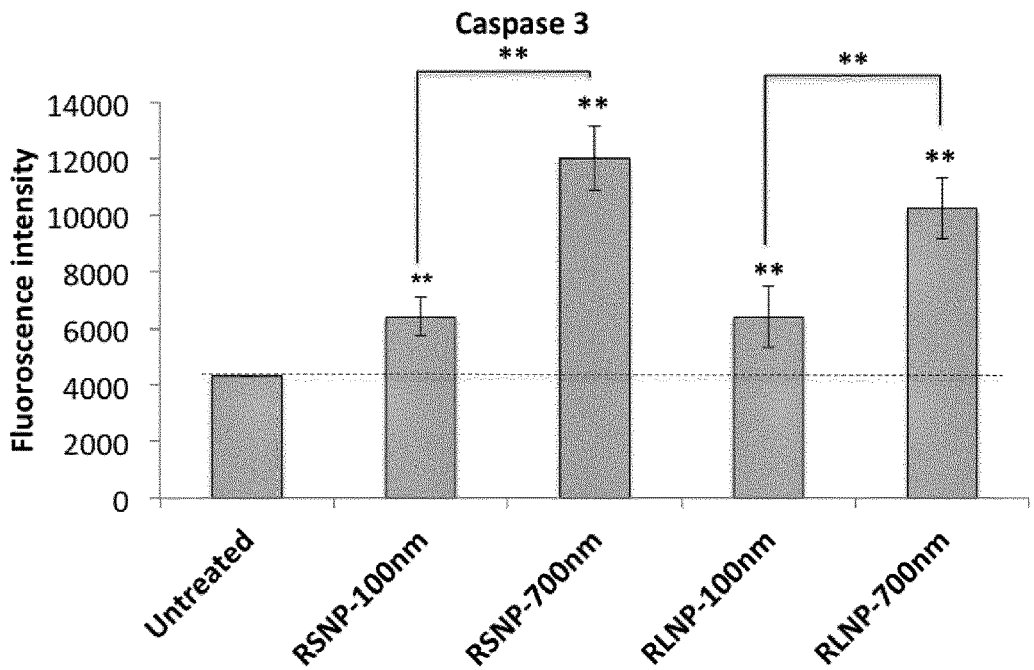
Fig. 18-B
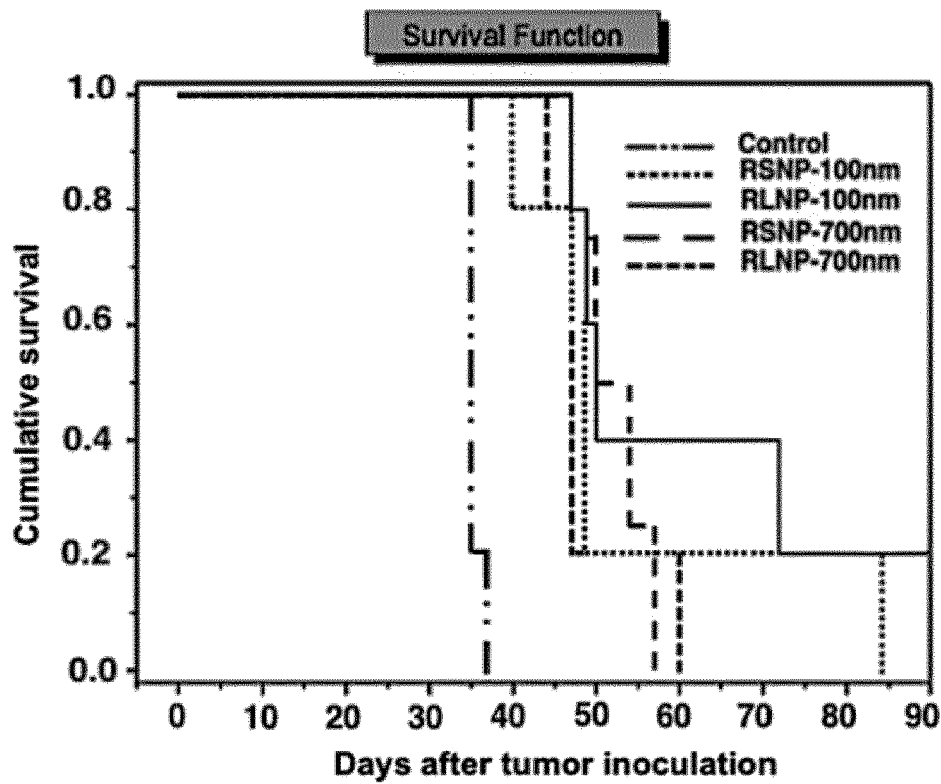
Fig. 19-A

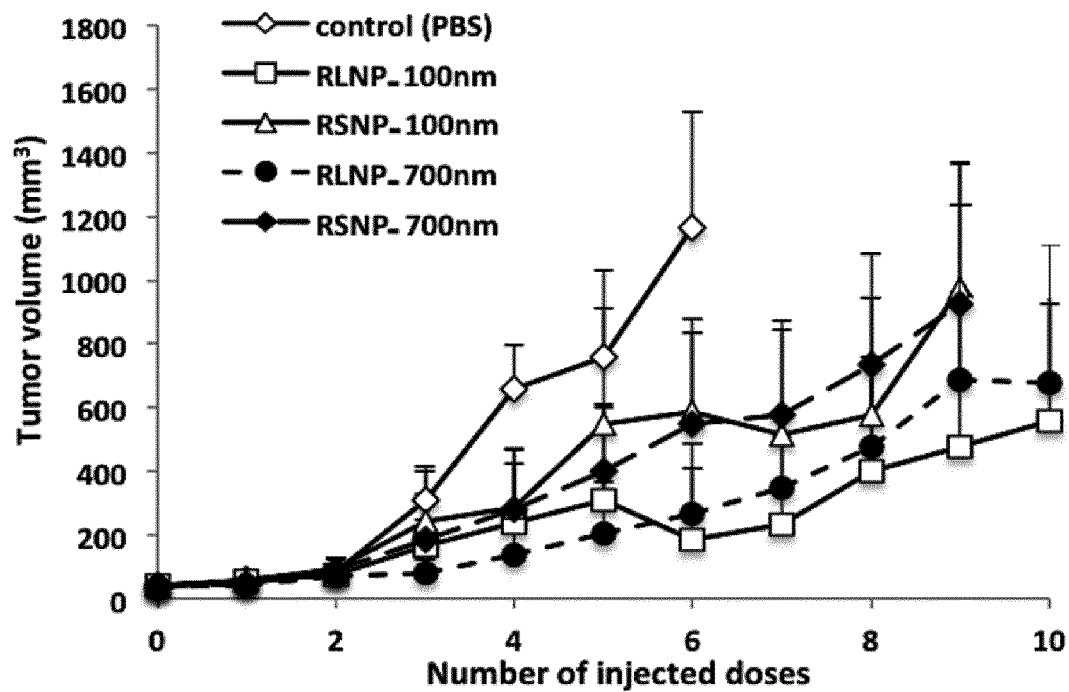
Fig. 19-B
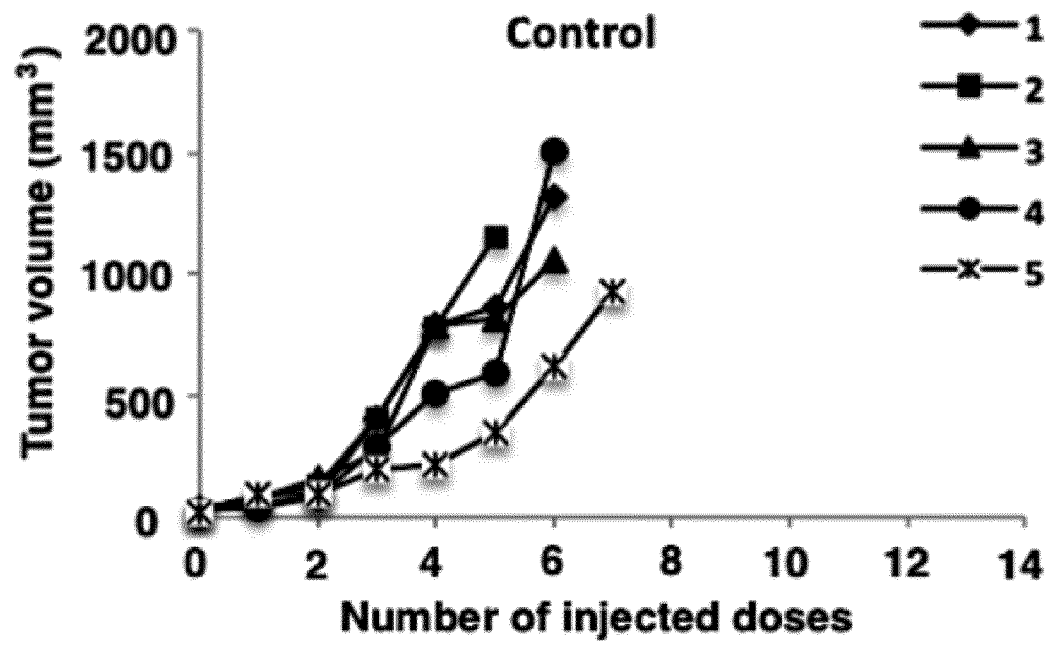
Fig. 19-C-1

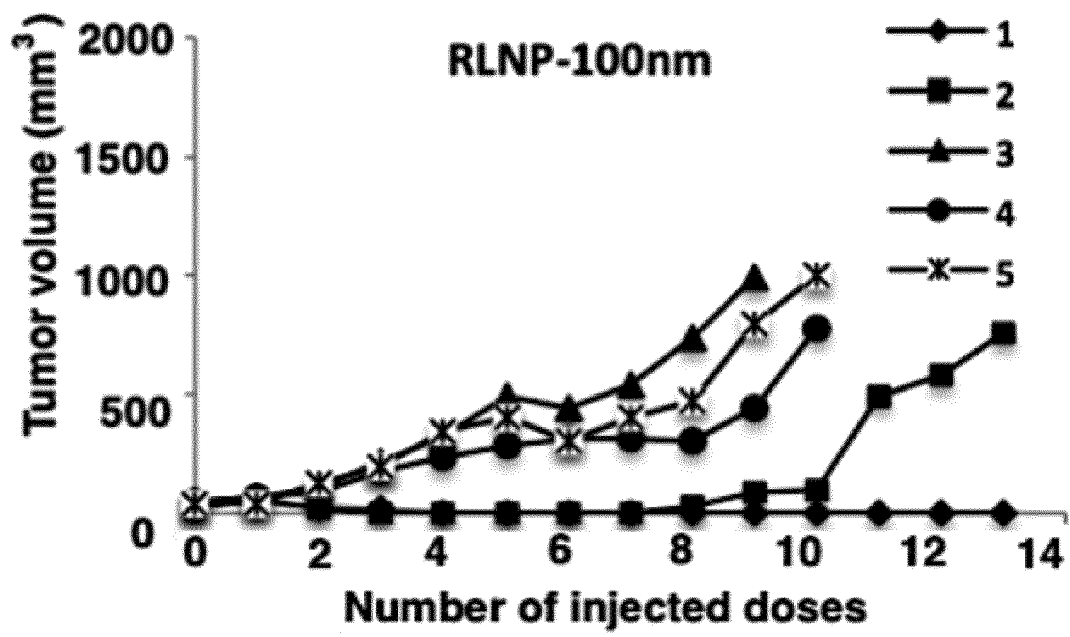
Fig. 19-C-2
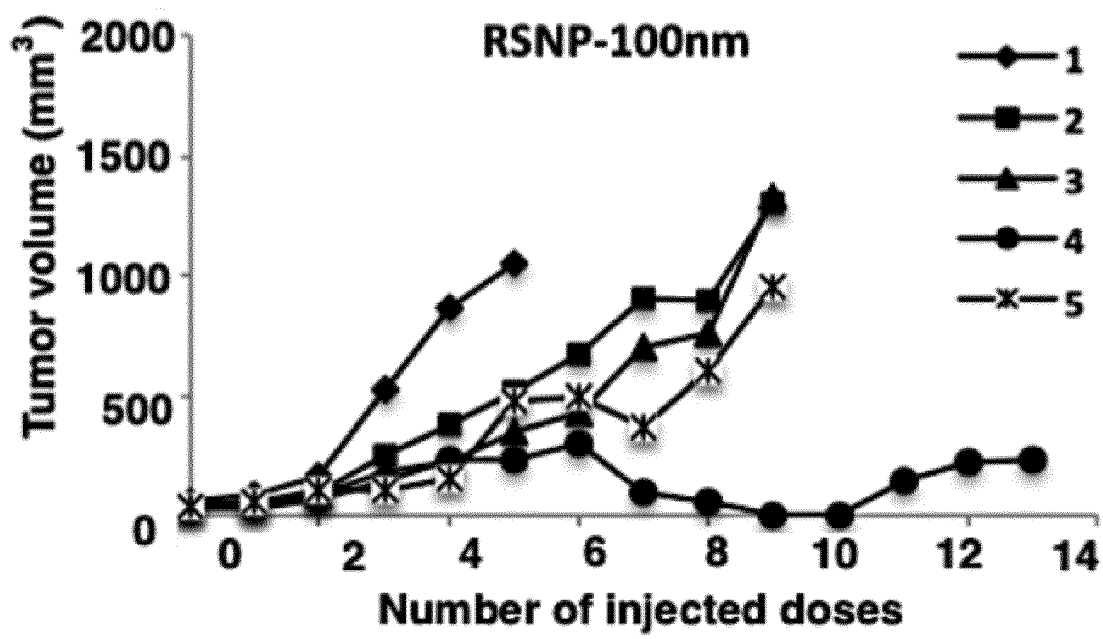
Fig. 19-C-3

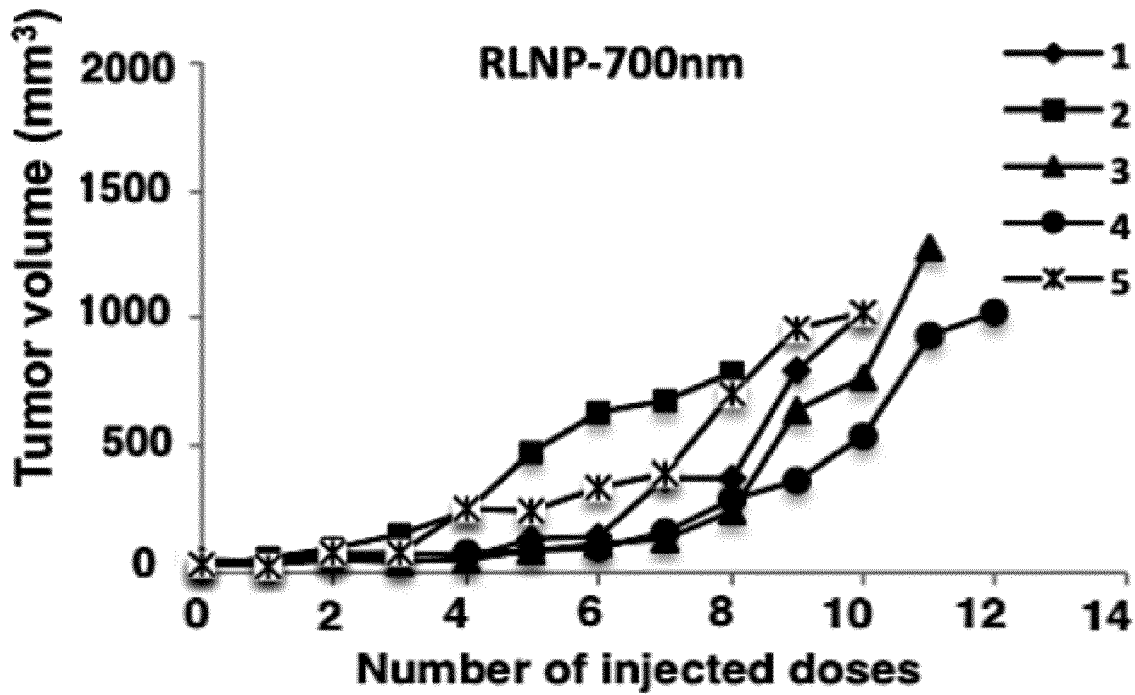
Fig. 19-C-4
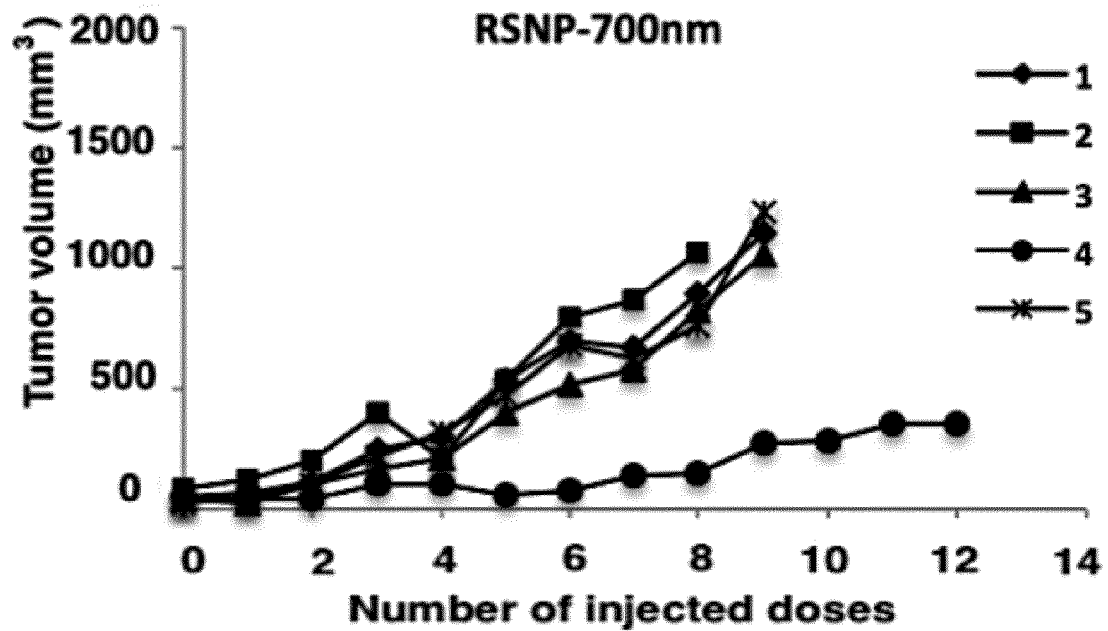
Fig. 19-C-5

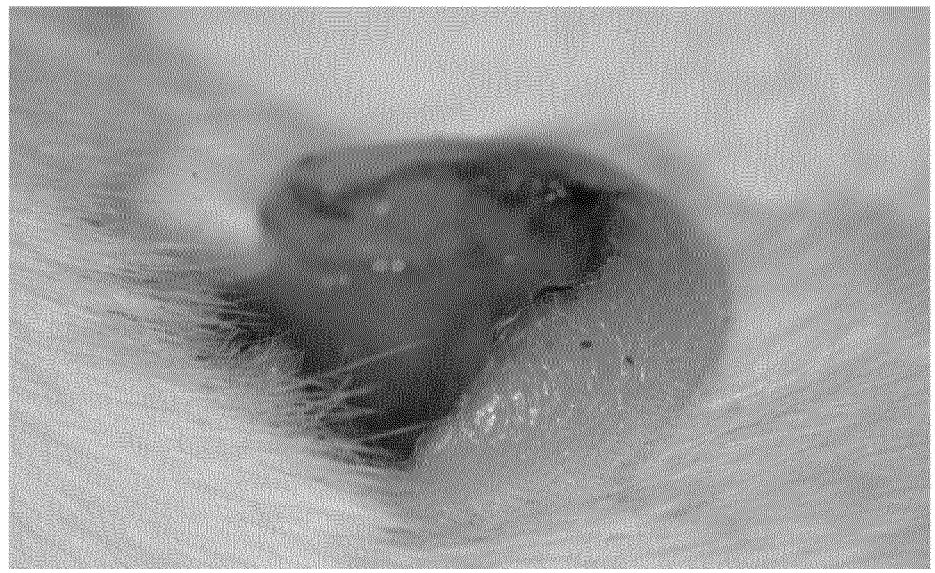
Fig. 19-D
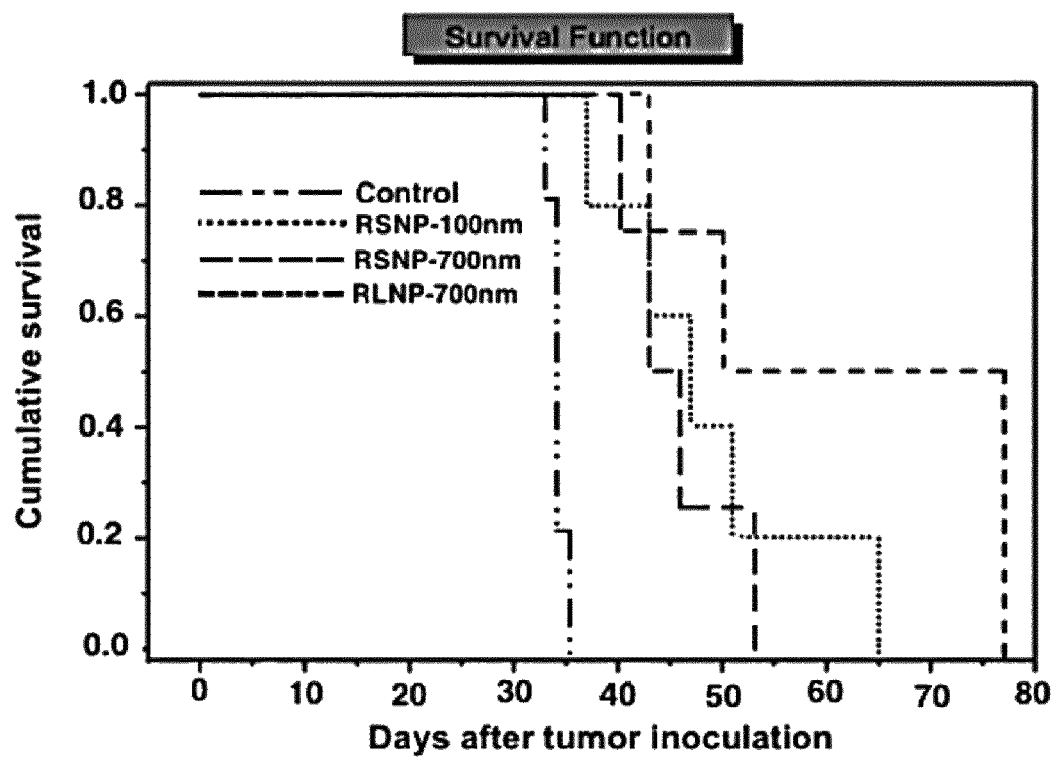
Fig. 20-A

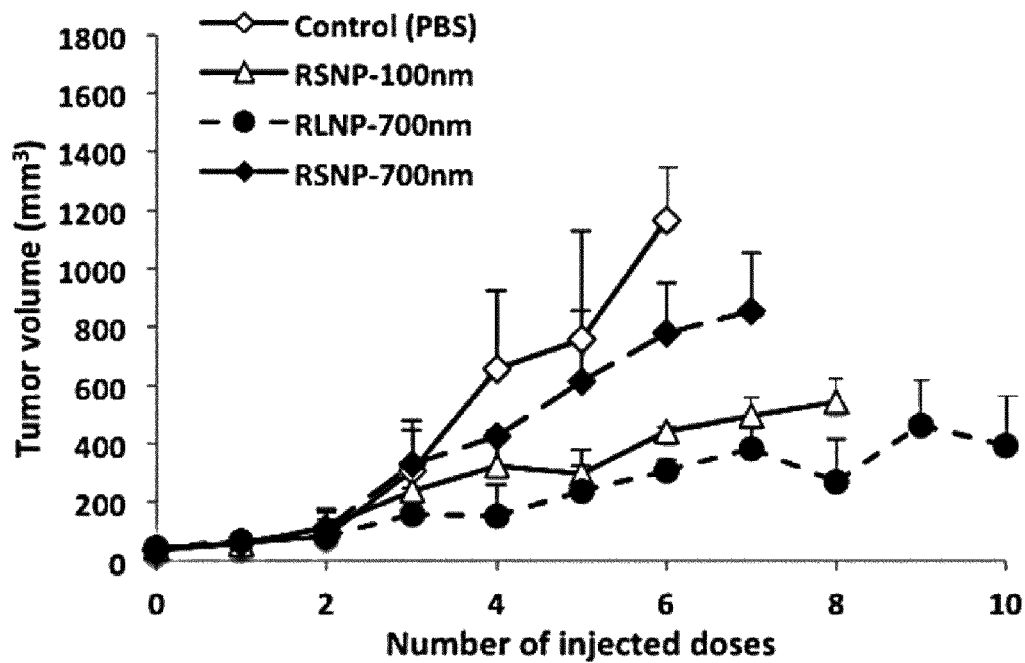
Fig. 20-B
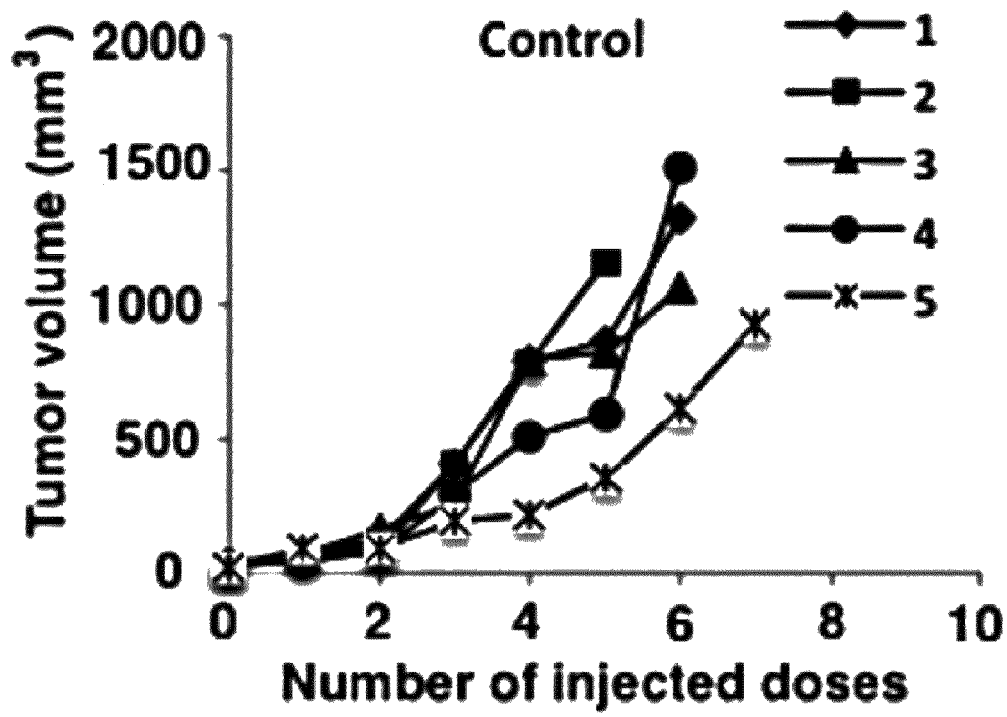
Fig. 20-C-1

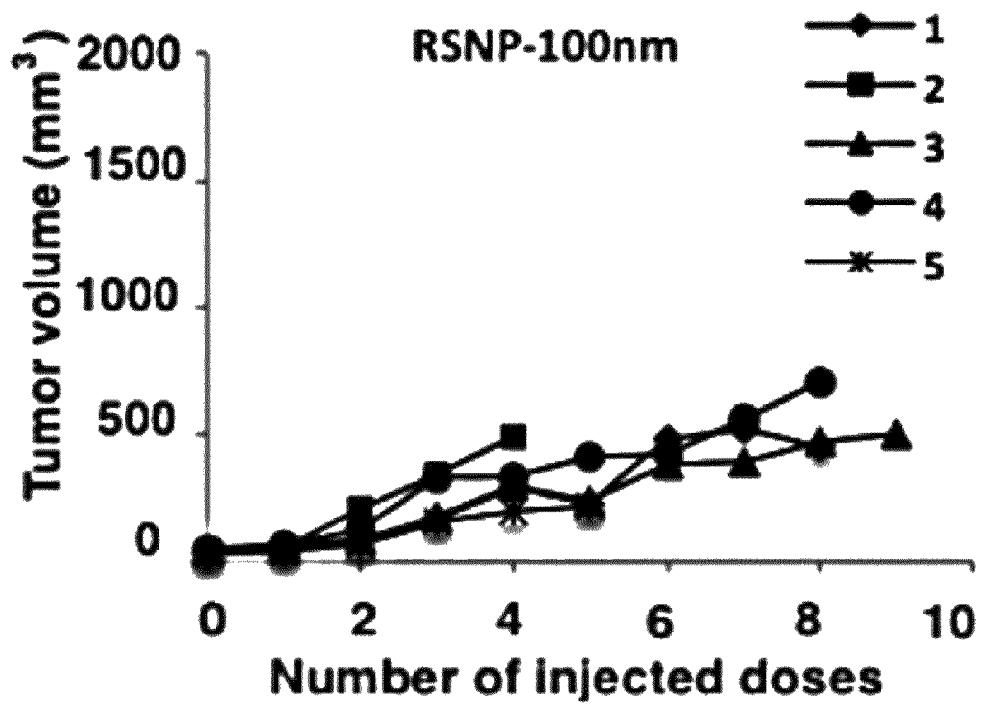
Fig. 20-C-2
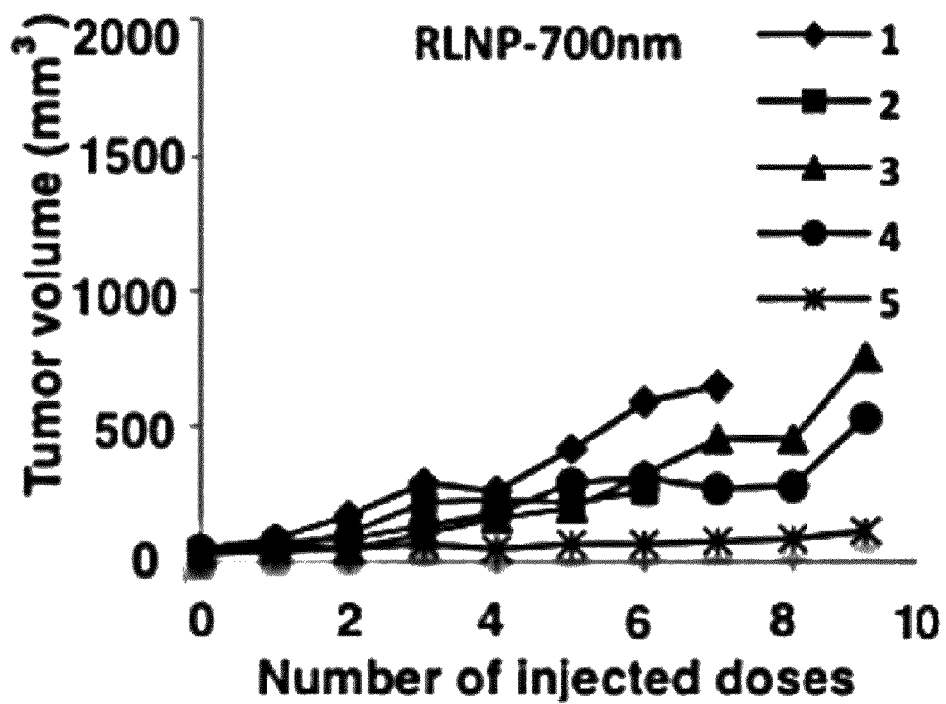
Fig. 20-C-3

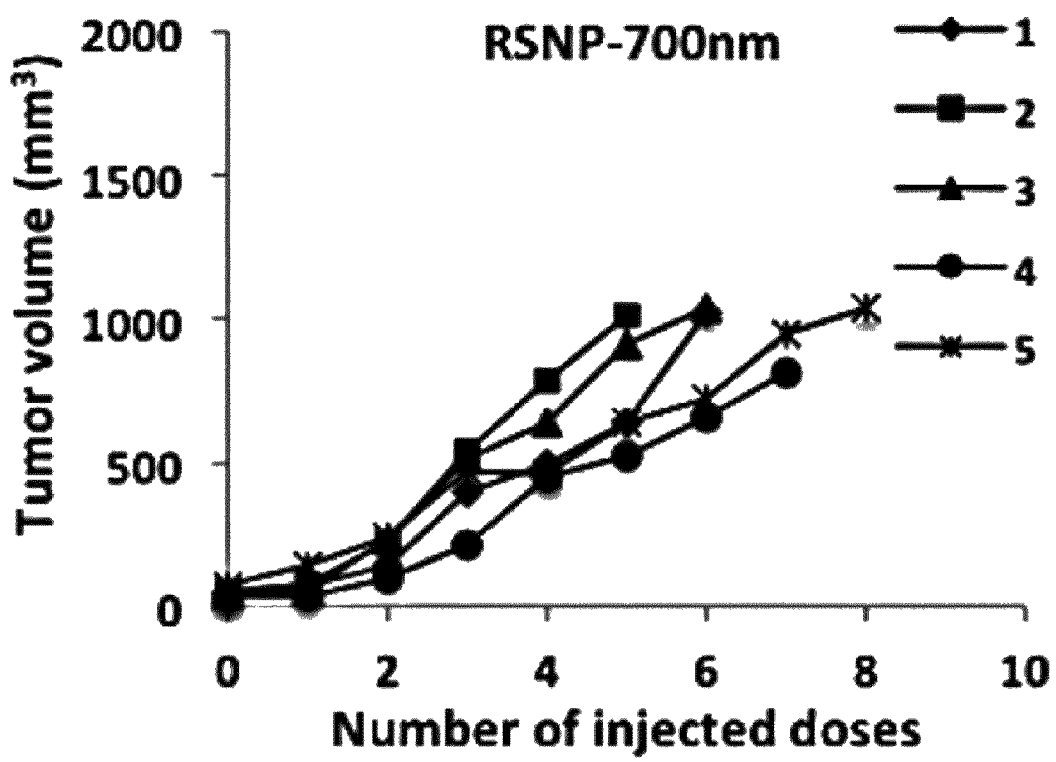
Fig. 20-C-4
Fig. 20-D-1

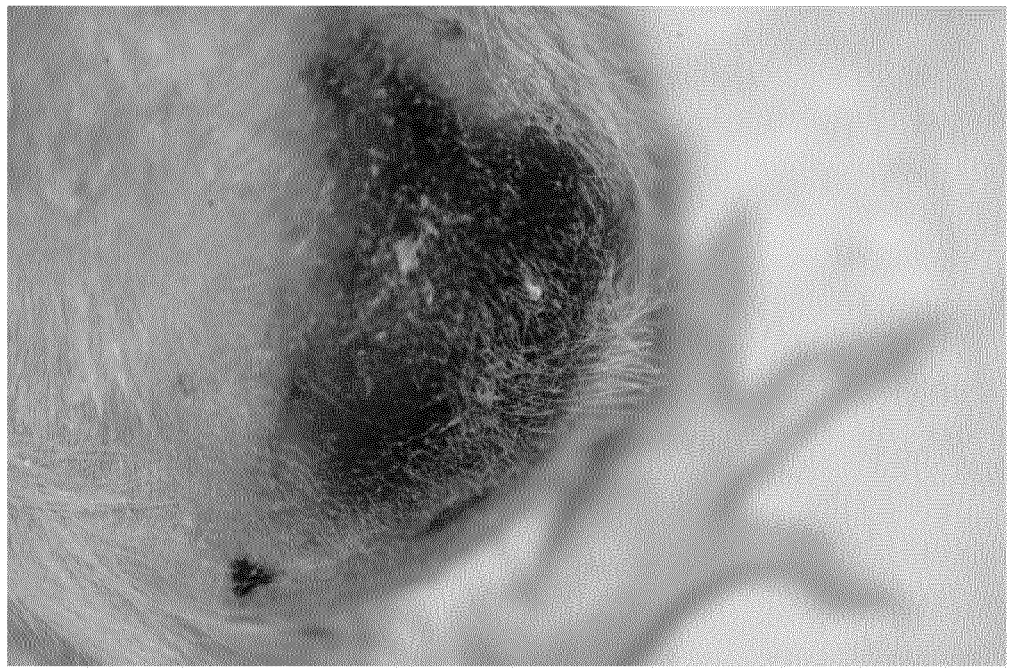
Fig. 20-D-2
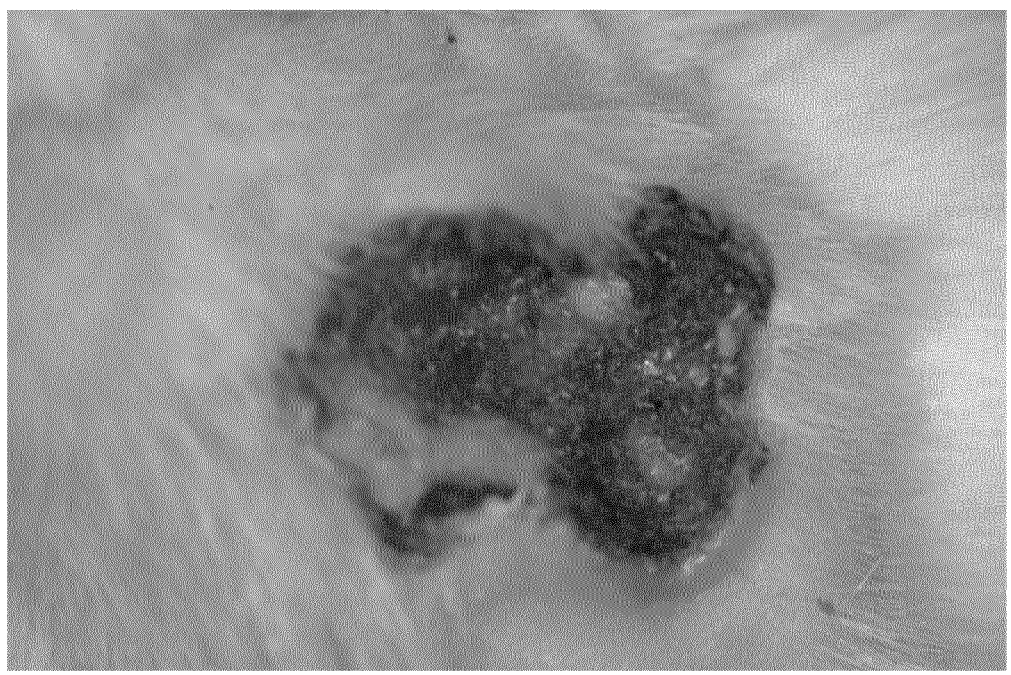
Fig. 20-D-3

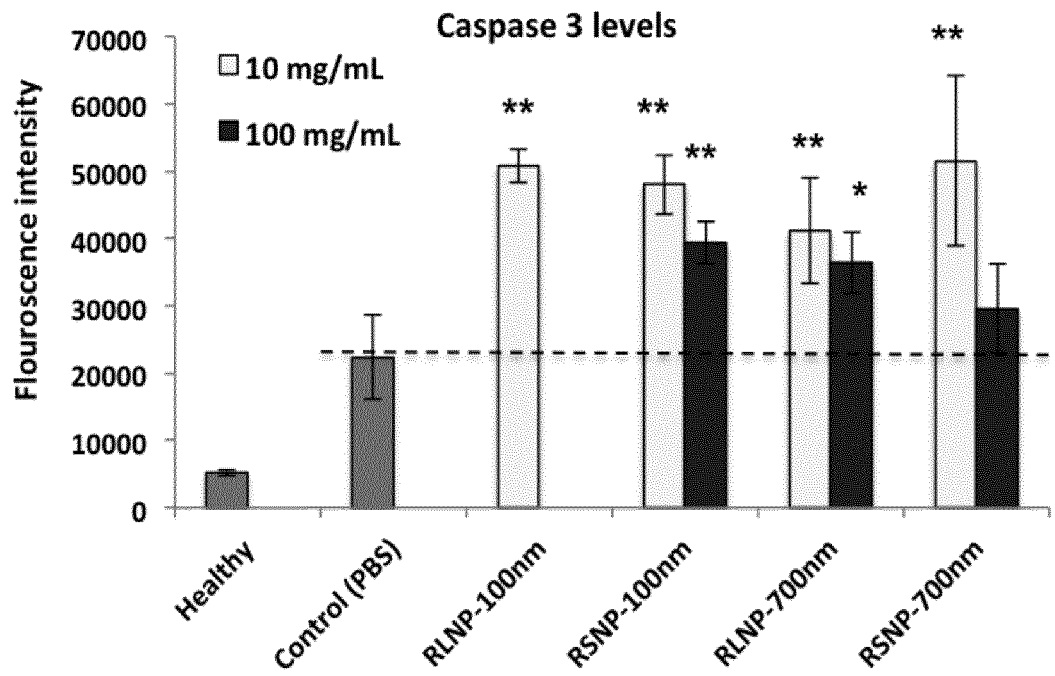
Fig. 21-A
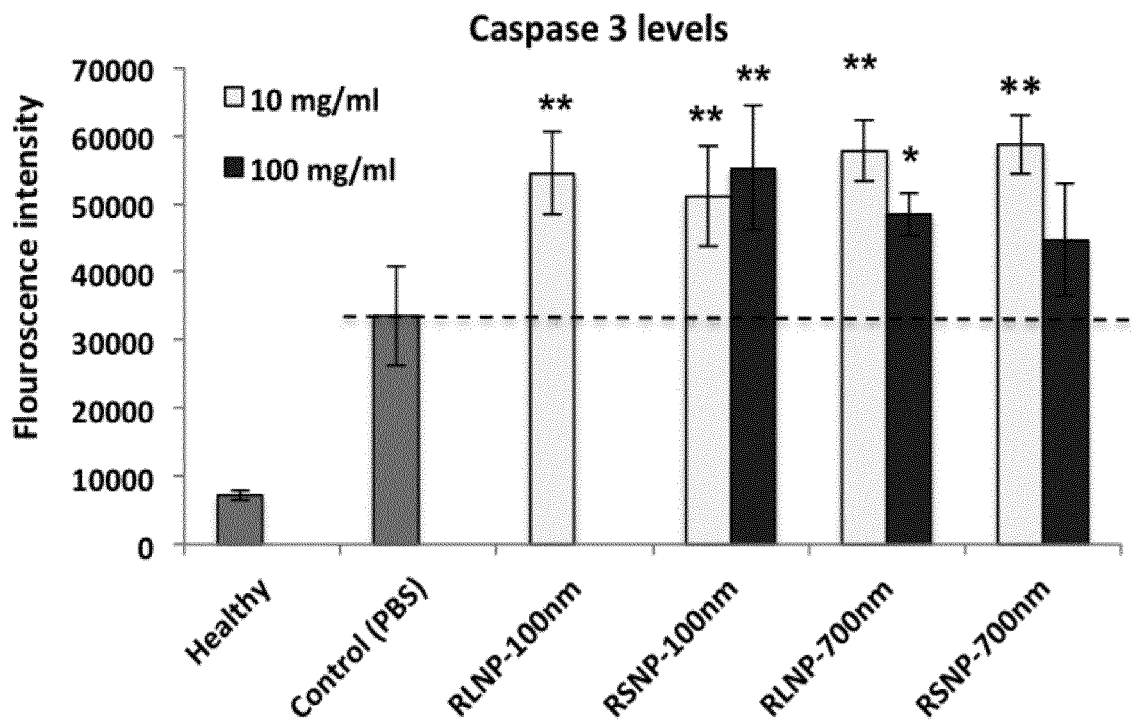
Fig. 21-B

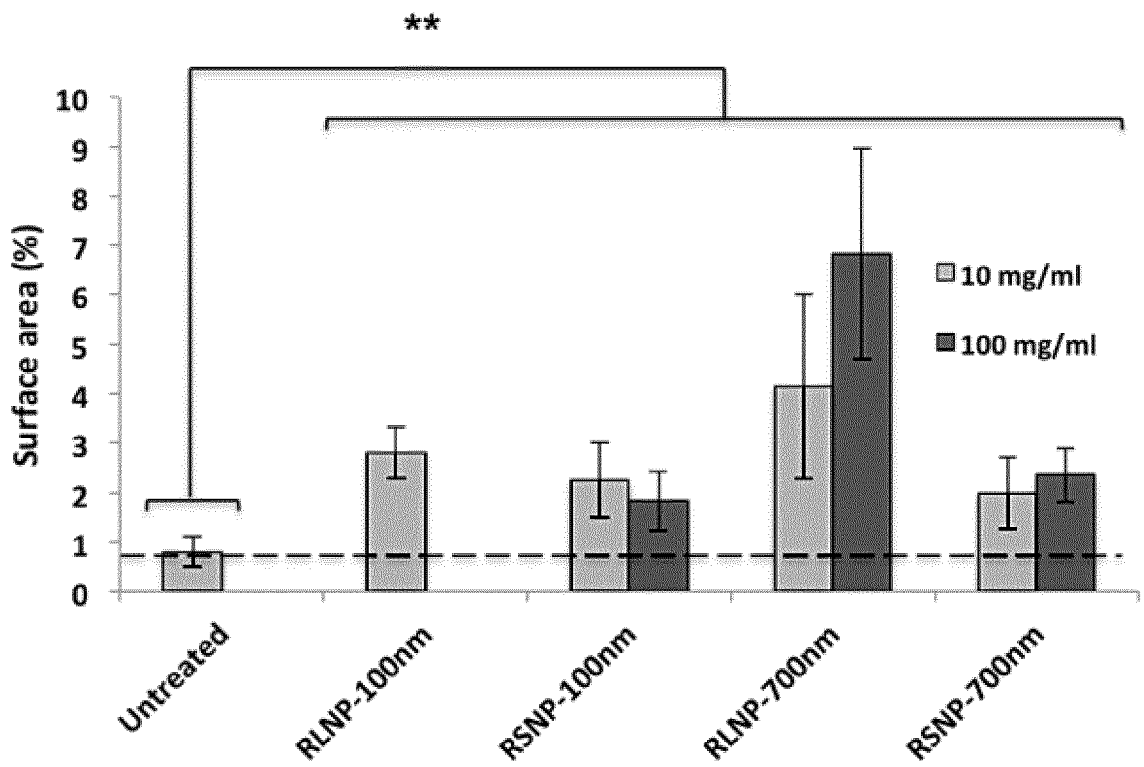
Fig. 22
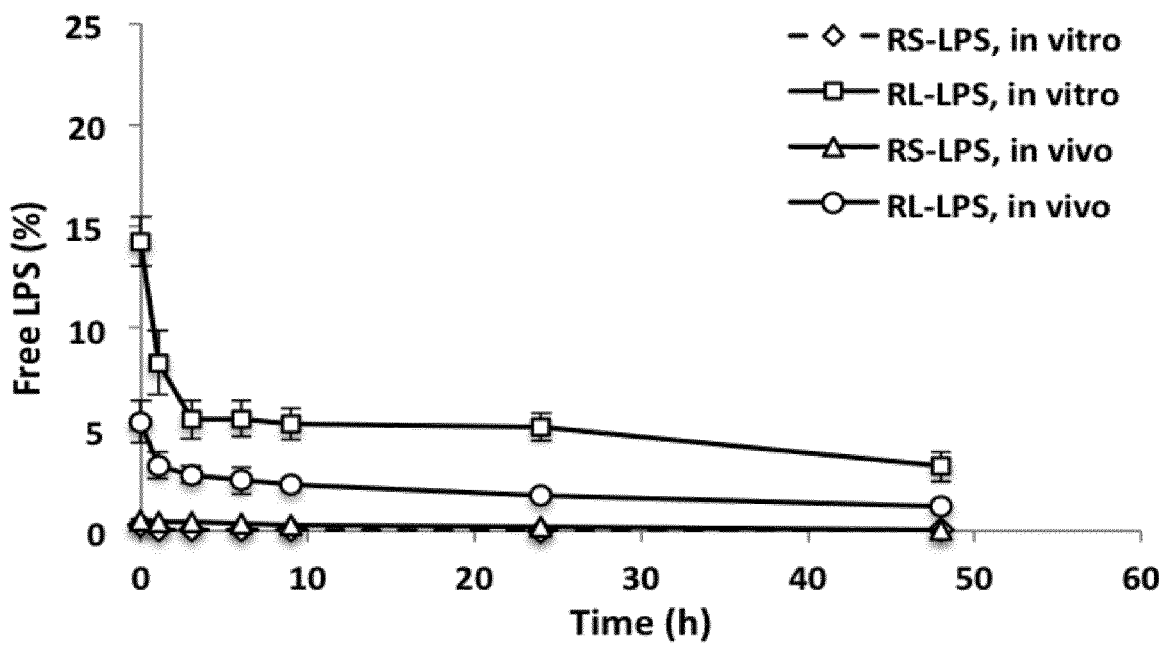
Fig. 23-A

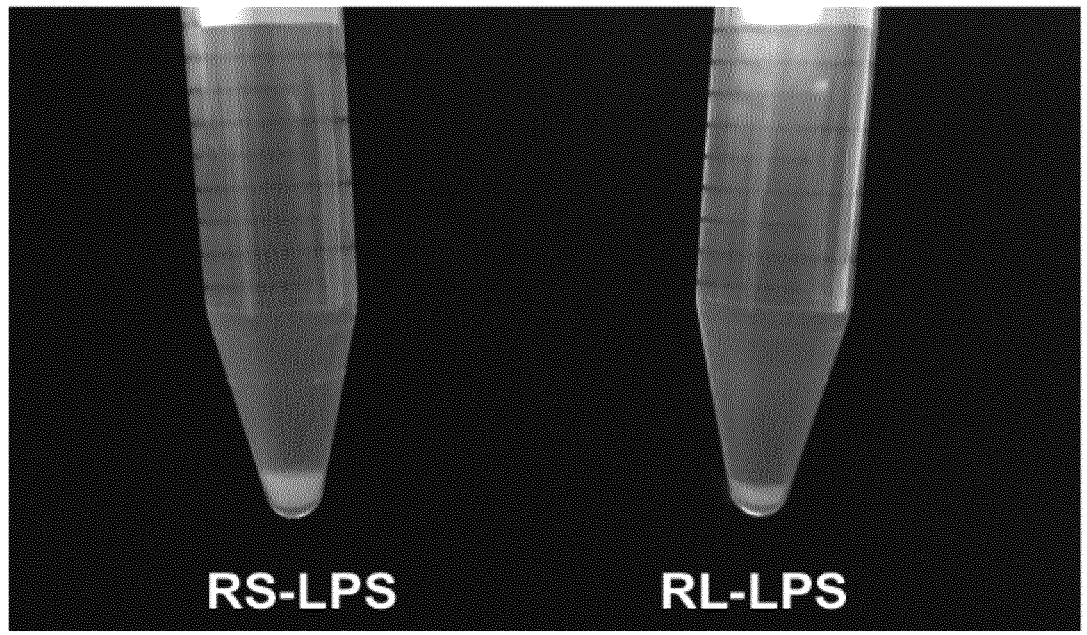
Fig. 23-B
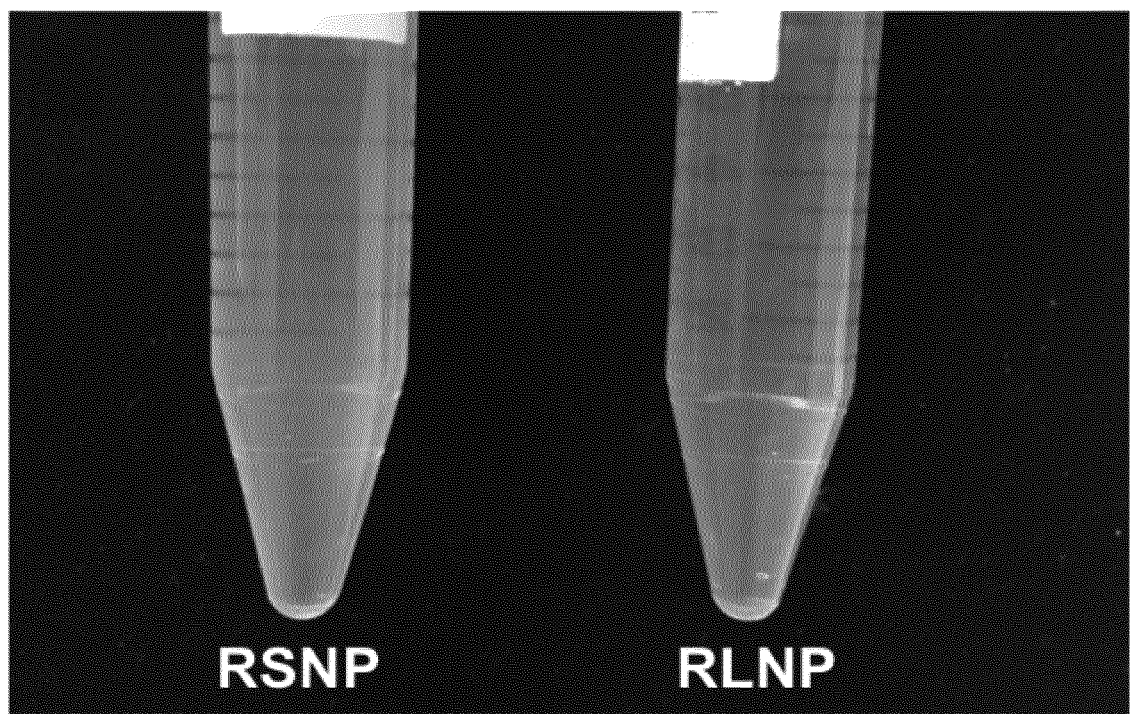
Fig. 23-C

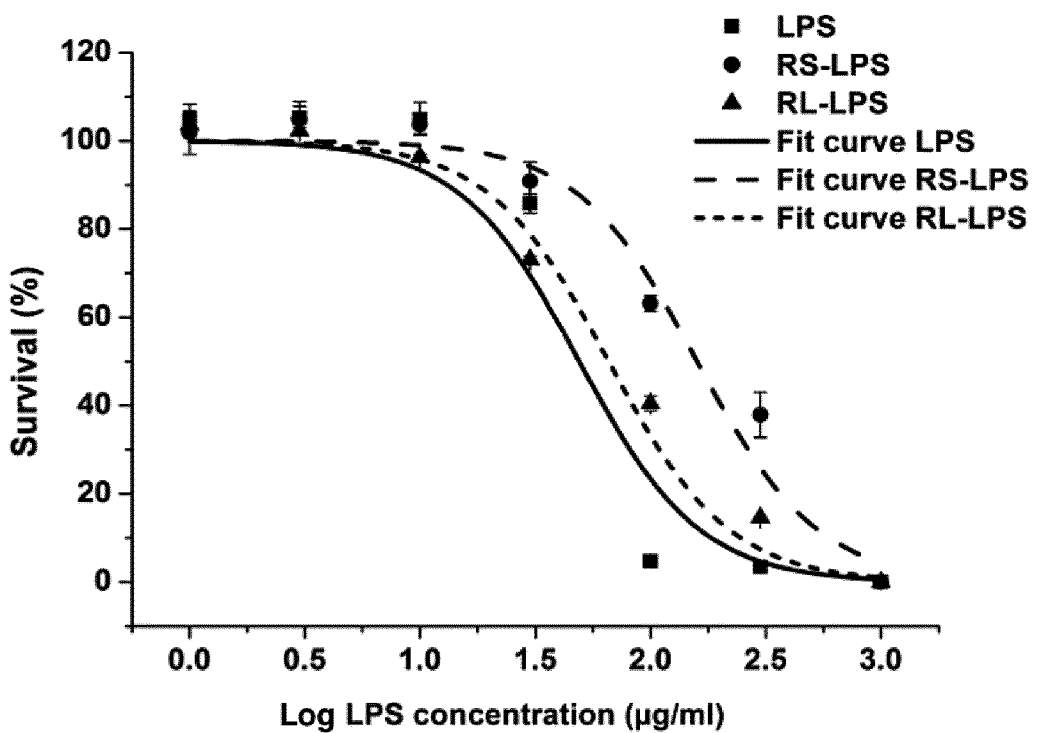
Fig. 24-A
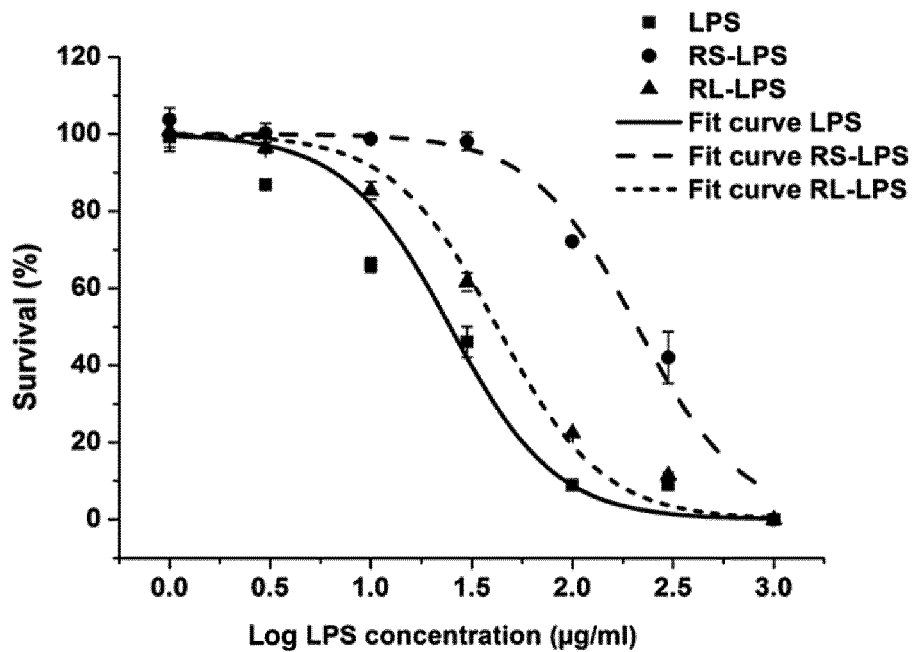
Fig. 24-B

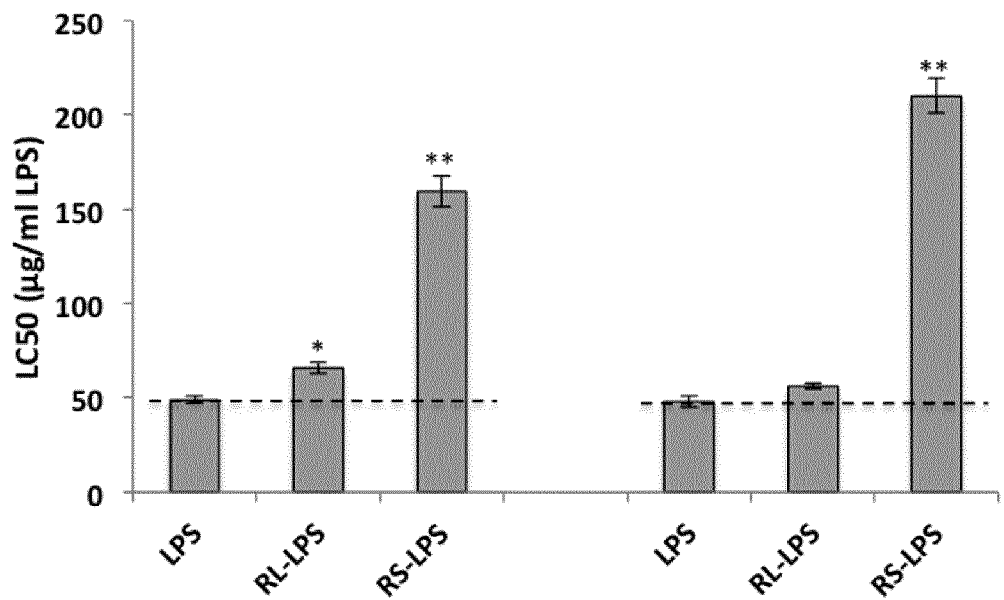
Fig. 24-C
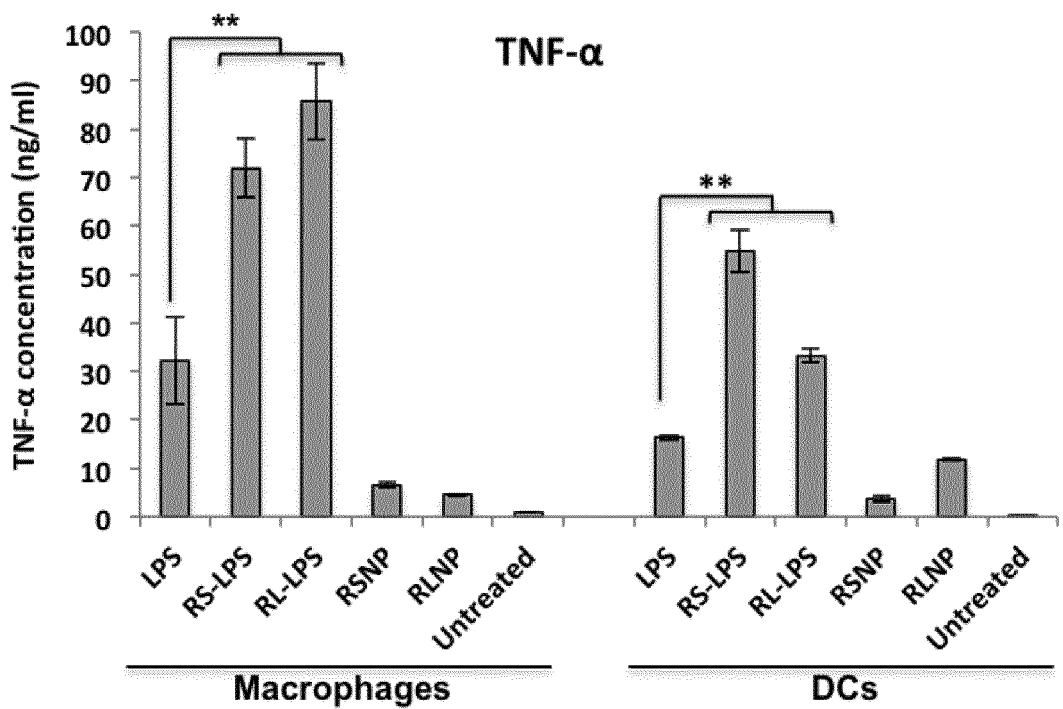
Fig. 25-A

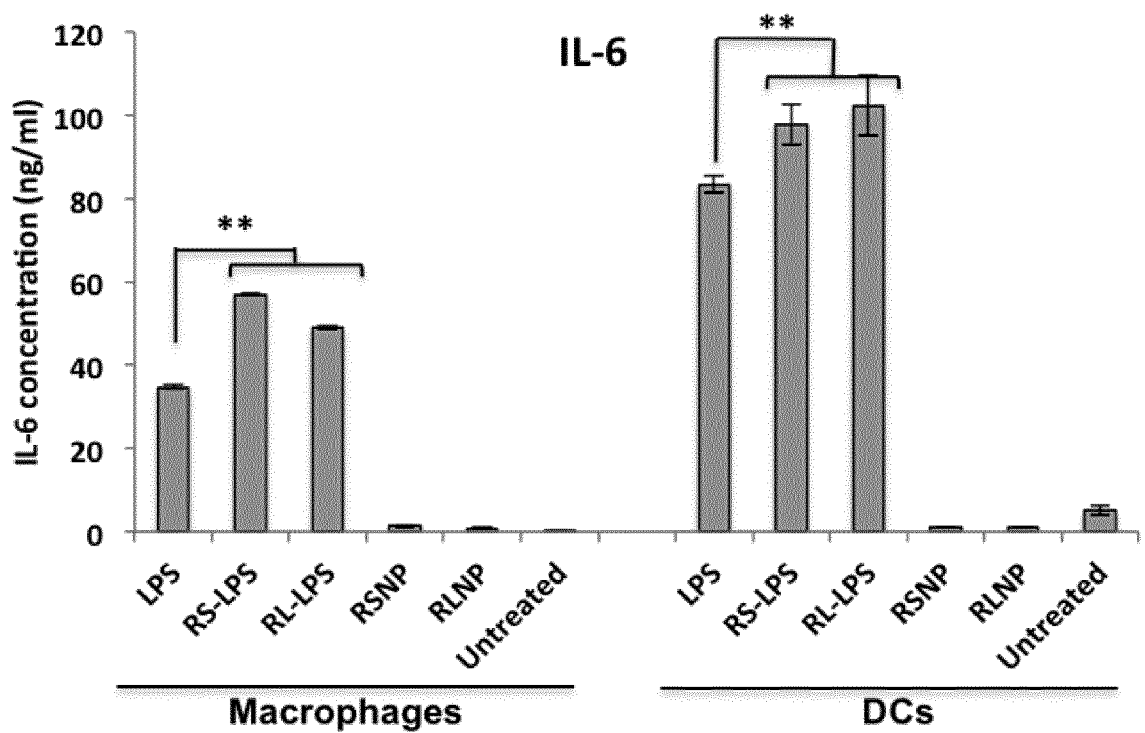
Fig. 25-B
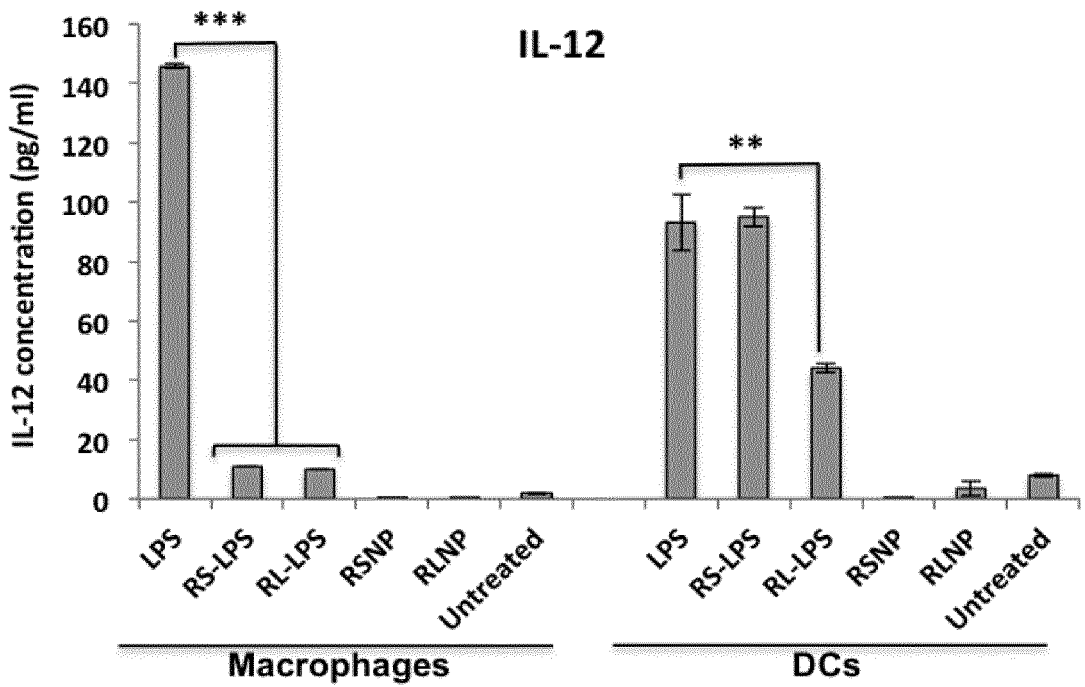
Fig. 25-C

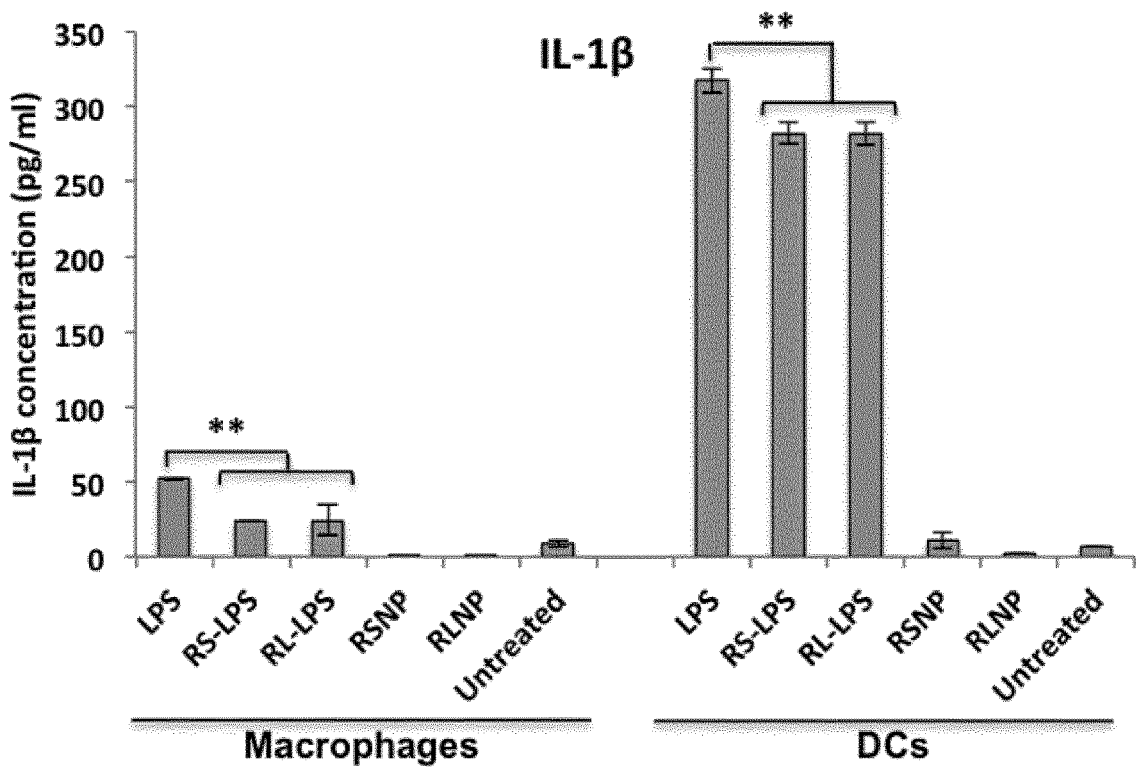
Fig. 25-D
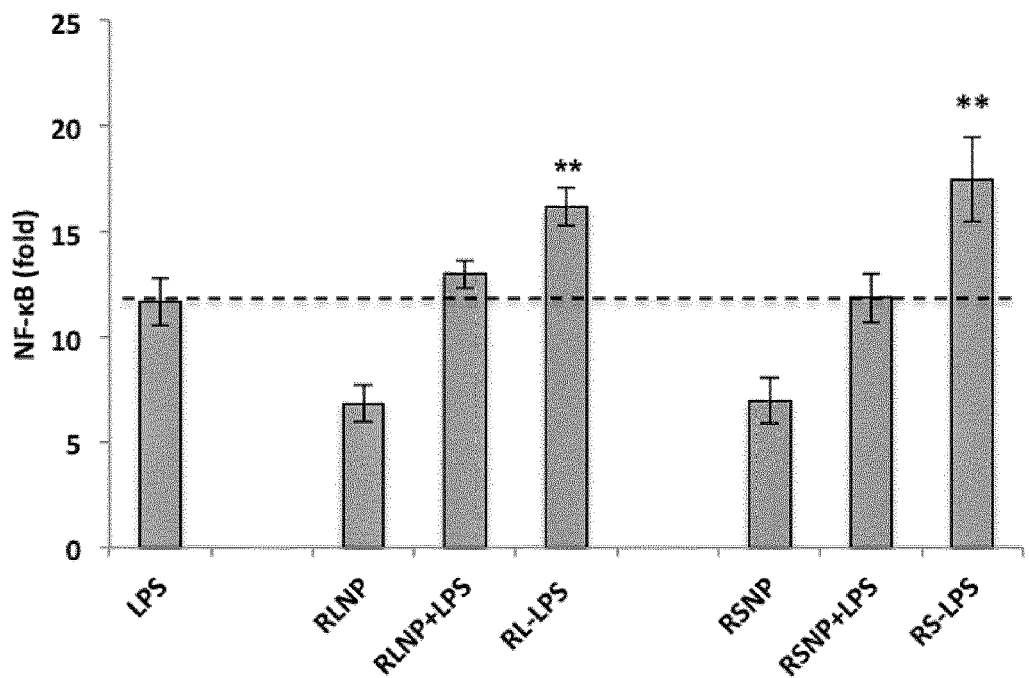
Fig. 26

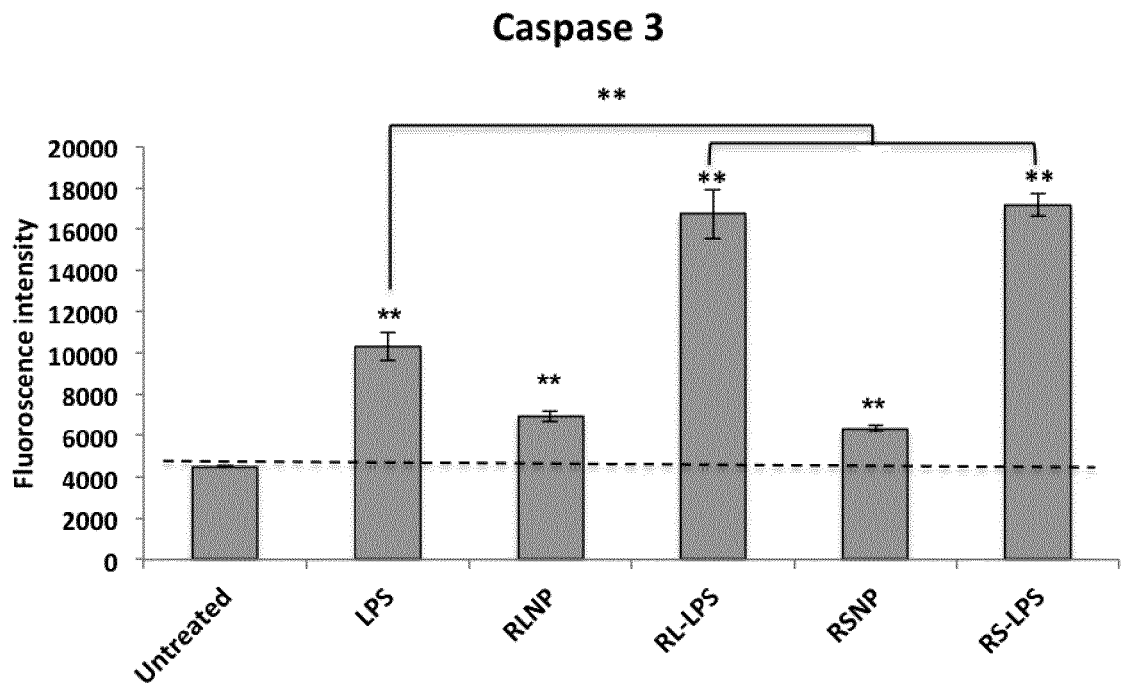
Fig. 27
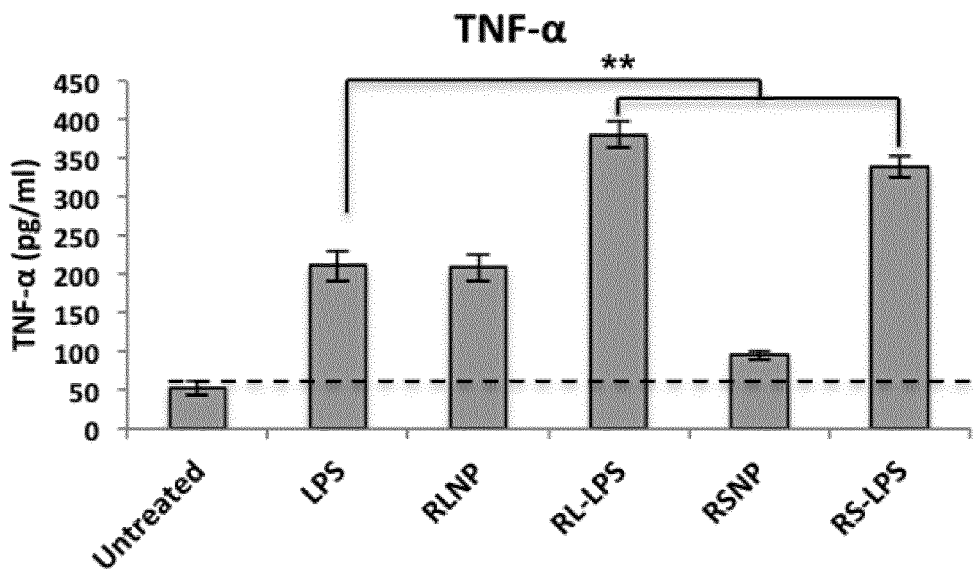
Fig. 28-A

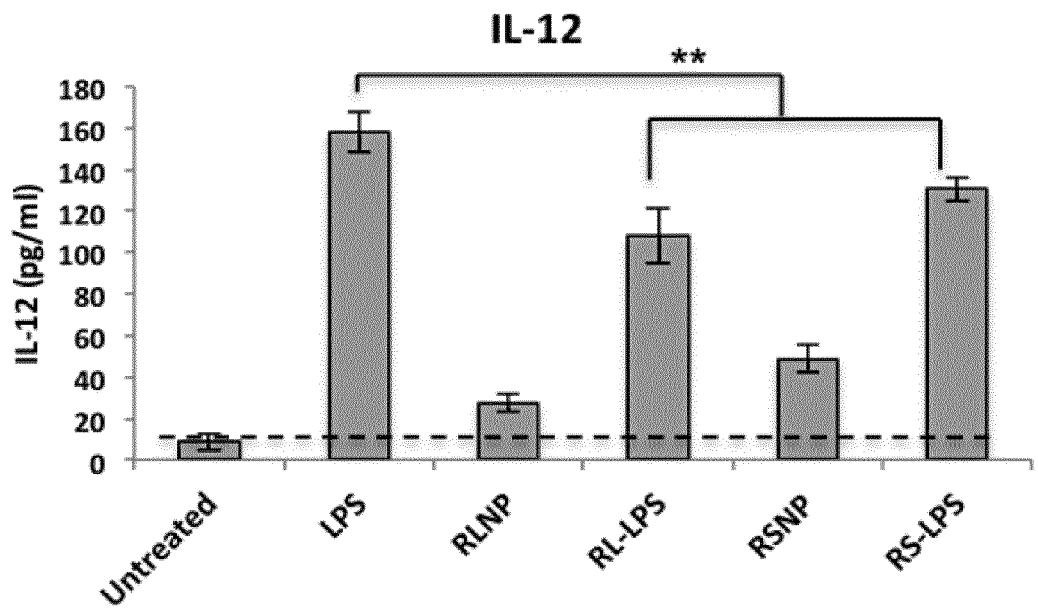
Fig. 28-B
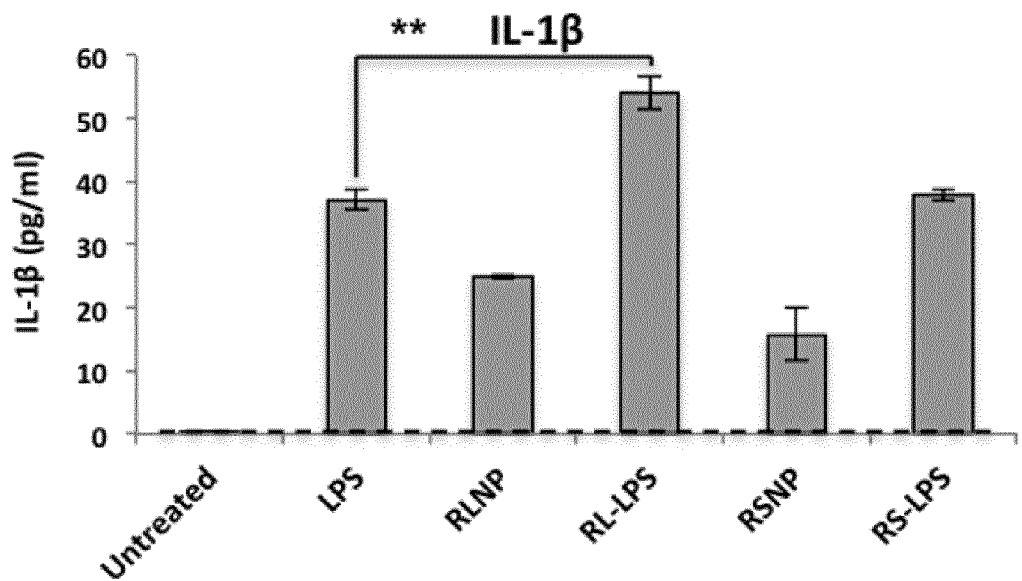
Fig. 28-C

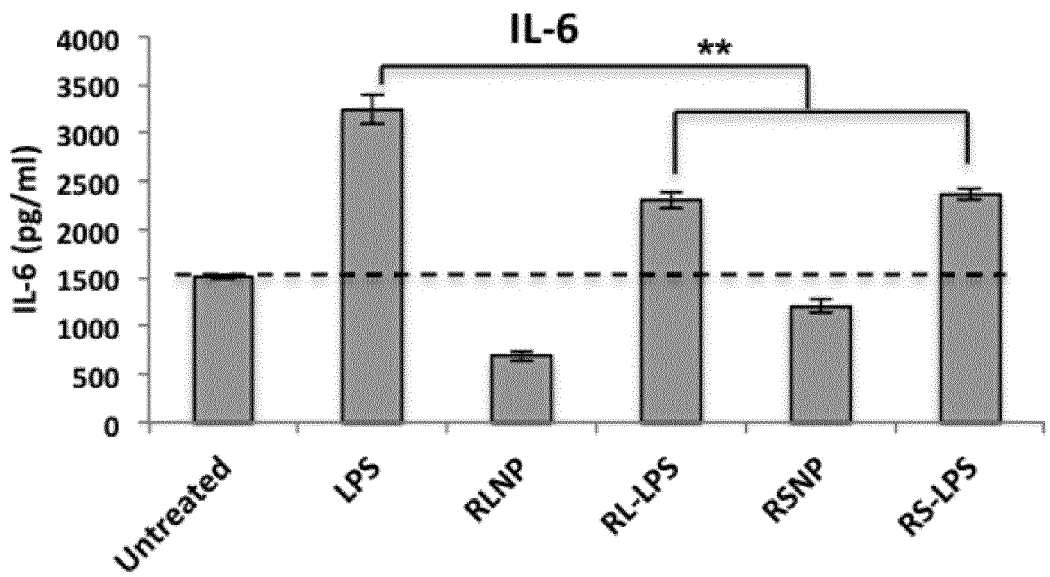
Fig. 28-D
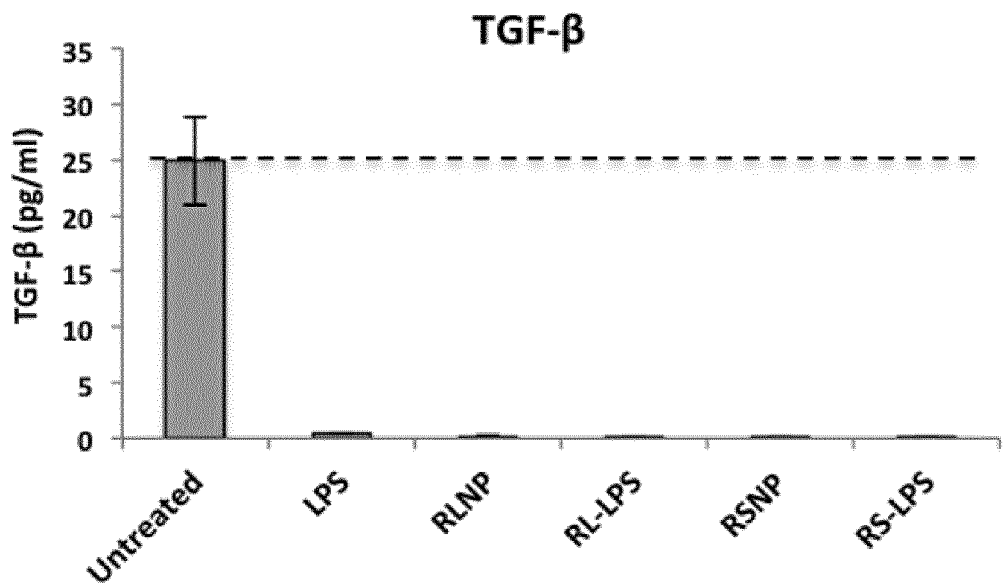
Fig. 28-E

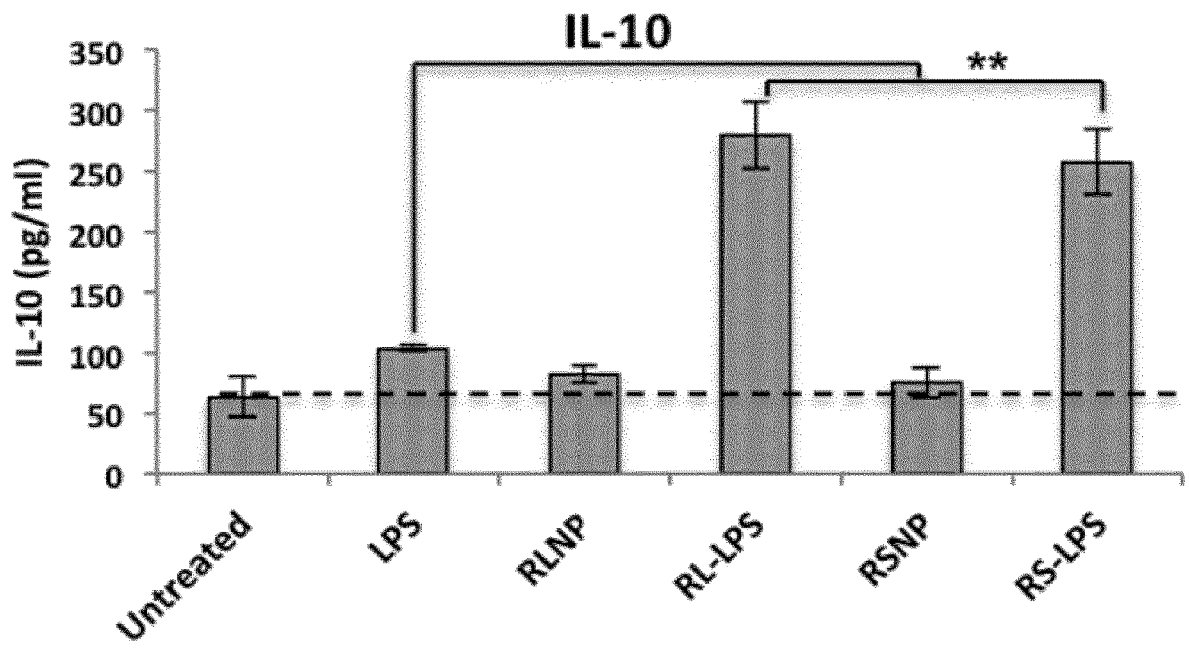
Fig. 28-F
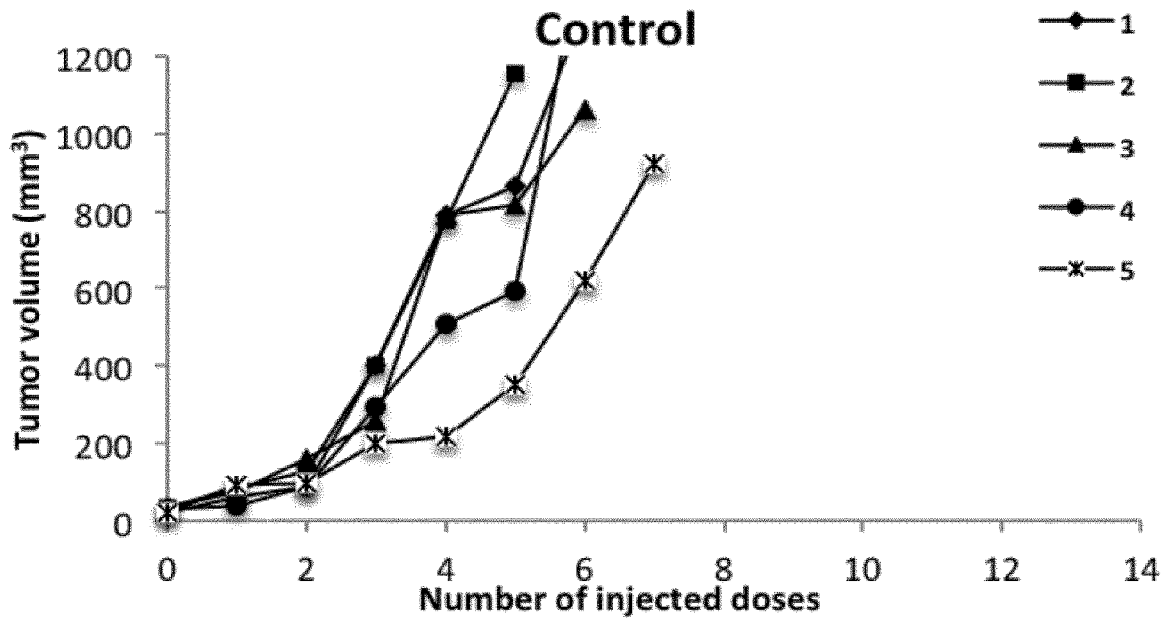
Fig. 29-A

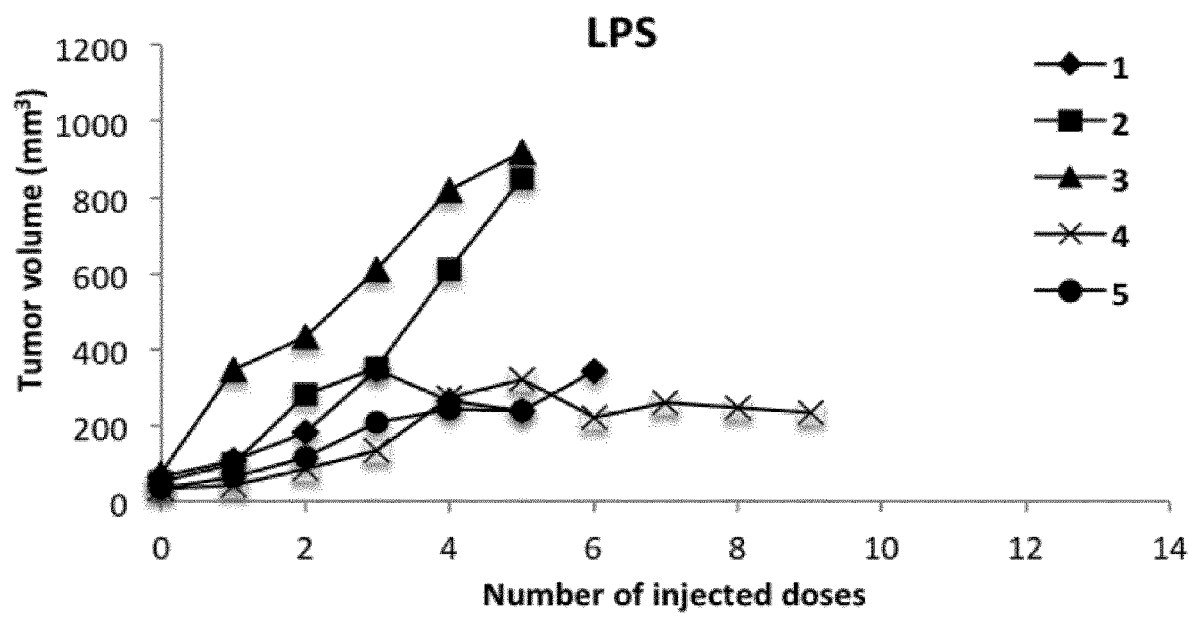
Fig. 29-B
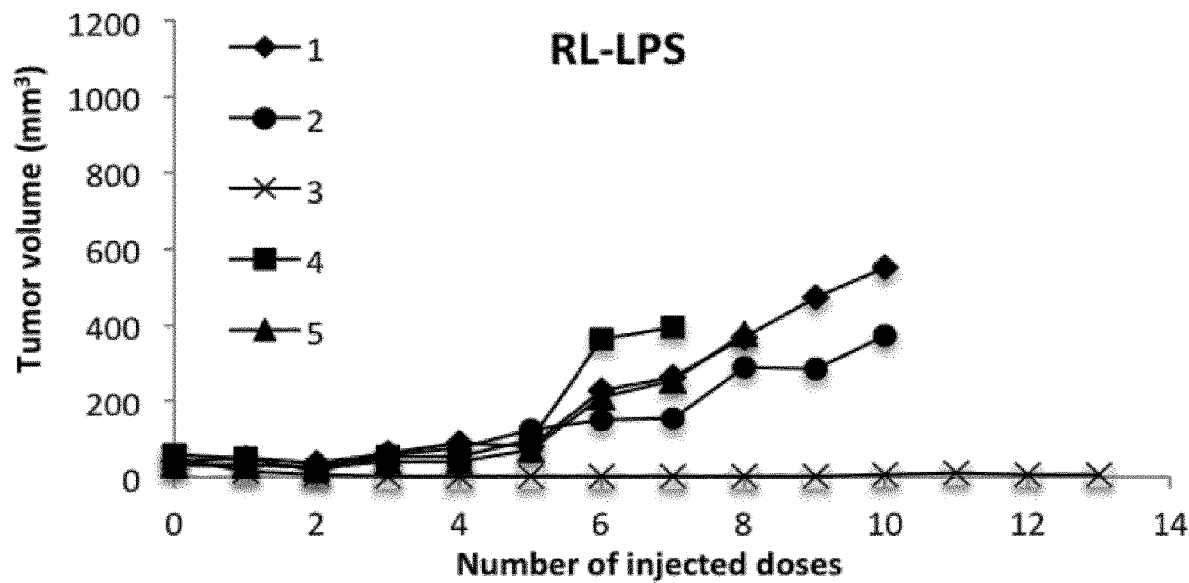
Fig. 29-C

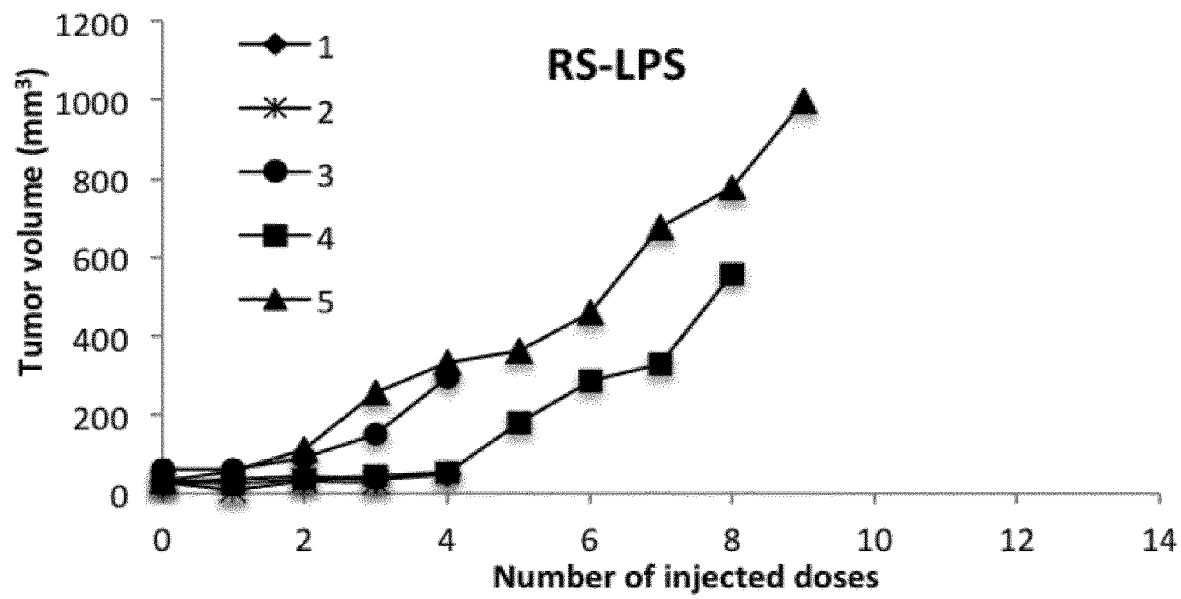
Fig. 29-D
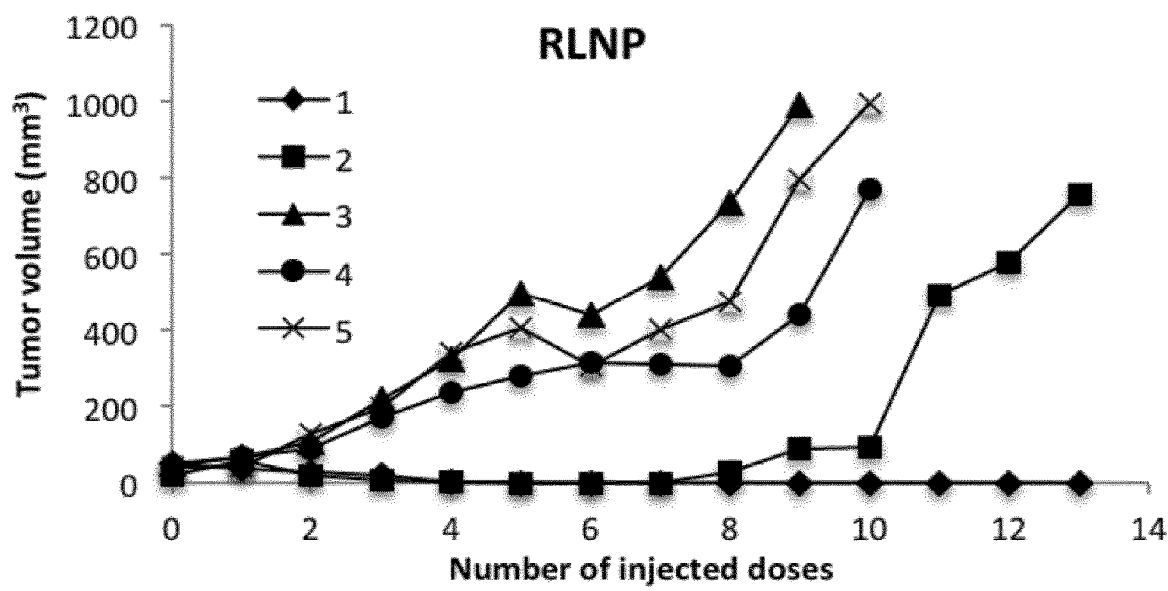
Fig. 29-E

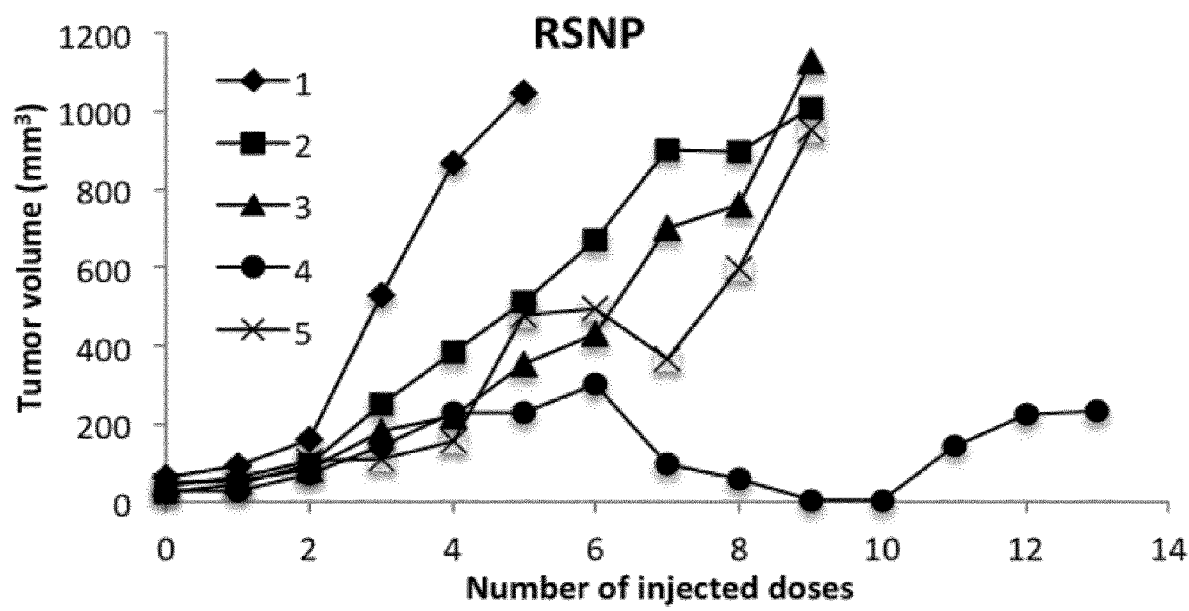
Fig. 29-F
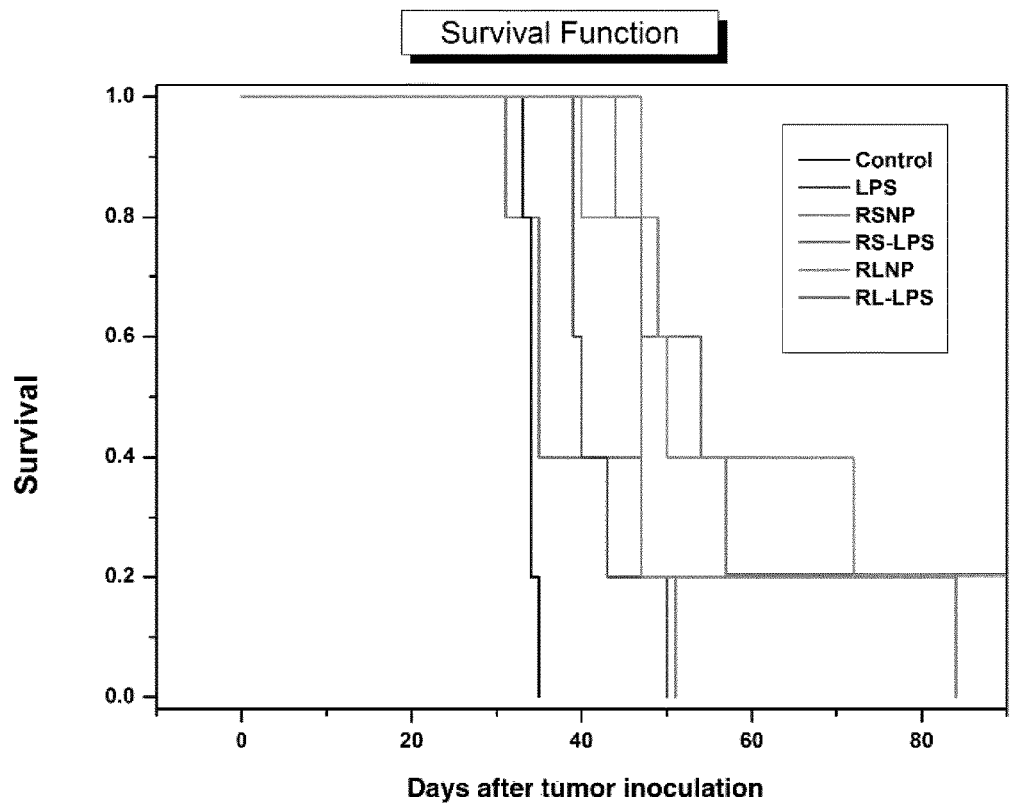
Fig. 30

USE OF NANOPARTICLES FOR IMMUNOTHERAPY

This application is a. National Stage entry under § 371 of International Application No. PCT/EP2018/052433, filed on Jan. 31, 2018, and which claims the benefit of European Application No, 17154040.4, filed on Jan. 31, 2017.

BACKGROUND OF THE INVENTION

Field of the Invention

The present disclosure relates to a composition for use as a medicament, the use of the composition for the treatment of cancer, as well as to a composition.

BACKGROUND OF THE INVENTION

A leading cause of mortality and morbidity worldwide, cancer remains to this day one of the most devastating disorders afflicting the humans. Even today, the main cancer treatment strategies include surgical intervention, radiation and chemotherapy. Still, alleviation of the disease severity comes at the cost of significant undesirable side effects, and the metastatic nature of the disorder renders the absolute recovery elusive. Many of the recent cancer treatment strategies seek to reinforce the immune system's potential to combat cancer. This approach, often referred to as immunotherapy, offers numerous advantages over the conventional therapeutic approaches which are painful, invasive, indiscriminate for healthy and diseased cells, and are associated with remarkable side effects. The benefits of immunotherapy include higher access of the activated immune cells to cancerous areas, ability to target both quiescent and proliferative cancer cells, lower levels of resistance to or evasion from the therapeutic strategy, higher specification for tumor cells, and reduction of the recurrence risk through the induction of the immunological memory.

Within the recent decades, active immunotherapeutic research has benefited from the activation of a variety of endogenous receptors to stimulate the immune response. These receptors, scientifically known as pattern recognition receptors (PRRs), are essentially responsible to alert the body to the presence of certain bacterial or viral components, namely pathogen associated molecular patterns (PAMPs). Of the four different PRR super families hitherto identified, Toll-like receptors (TLRs) have been most extensively explored for cancer immunotherapy. Amongst the agonists of different TLRs, Toll-like receptor 4 (TLR4) ligands (in particular lipopolysaccharide or LPS) have been long since exploited for cancer eradication.

It is therefore rational to exploit the strong pro-inflammatory response induced through the activation of the TLRs for breaking the tumor-associated immune tolerance, and to benefit from the resulted tumor regressive effects. Further investigation of natural and synthetic ligands of these receptors for the improvement of active immunotherapy in cancer is thereby highly relevant.

The prime natural ligand of TLR4, LPS is a predominant glycolipid found in the outer membrane of Gram-negative bacteria. It is composed of three distinct parts including a repetitive glycan polymer scientifically referred to as O-antigen, O-polysaccharide, or O-side chain, a core oligosaccharide, and a lipid A, which is a phosphorylated glucosamine disaccharide decorated with multiple fatty acids. However, LPS administered intravenously has severe systemic side effects (such as Shwartsman phenomenon and systemic inflammatory response syndrome (SIRS)) restricting the maximum administrable dosage particularly in case of LPS.

Of all TLRs, TLR4 is the only receptor with the ability to induce two different signaling pathways. The first pathway is the MyD88-dependent pathway, which, through the activation of NF-κB, results in the production of pro-inflammatory cytokines and chemokines. The second pathway, however, known as the TRIF-dependent or MyD88-independent pathway mediates the activation of type 1 IFNs. Research has revealed that TLR4 ability to activate both pathways is necessary to maximize the immunostimulatory potential of the dendritic cells (DCs).

Following the stimulation of TLR4 expressed by antigen presenting cells (APCs) such as macrophages and DCs, a wide range of pro-inflammatory substances, cytokines, chemokines and their receptors are produced via both of these pathways. These include iNOS, TNF-α, IL-1α, IL-1β, IL-1ra, IL-6, IL-8, IL-10, IL-12p40, IL-15, IL-23, macrophage inflammatory protein (MIP)-1α, and MIP-1β, gamma-induced protein 10 (IP-10) and IFN-β[58]. Amongst these, IL-1β and TNF-α are necessary for the coordination of local and systemic inflammatory responses. Moreover, TNF-α plays a prominent role in TLR4 anticancer effect, given its ability to induce DC maturation and migration, which can in turn result in the lineage proliferation of T helper 1 (Th1) lymphocytes. DC maturation is crucial for cross-presentation of tumor antigens to CD8$^+$ T cells. TNF-α is also a crucial effector molecule in CD8$^+$ T cells and natural killer cells (NKs). Th1 lymphocytes and cytotoxic CD8$^+$ T cell responses are essential for the antitumor effects. In addition, the resulted enrichment of the tumor microenvironment with IFN-α and IL-12 leads to the attraction of the T cells to the area, whereas other cytokines activate the CD4$^+$ Th1 and consequently cytotoxic CD8$^+$ antitumor responses. IL-12 also establishes an essential part of the anticancer effect, mostly due to its ability to enhance the cytotoxicity of NKs and CD8$^+$ T cells. Furthermore, TLR4 activation enhances the antigen processing and presentation by impacting the expression of costimulatory molecules on the surface of the APCs and controlling the antigen uptake, which is a key factor for the initiation and regulation of the adaptive immunity. TLR4 agonists have thus been, and are still being, wildly explored as highly potential immunotherapeutics for the treatment of cancer.

SUMMARY OF THE INVENTION

In a first aspect, the present disclosure relates to a composition for use as a medicament, the composition comprising nanoparticles, wherein the nanoparticles comprise a polymer selected from the group consisting of PLGA, PLA, PGA, PCL and poly(meth)acrylates, or a lipid.

A preferred embodiment relates to the composition of the first aspect, wherein the nanoparticles comprise a polymer selected from the group consisting of PLGAs, amino alkyl methacrylate copolymers, methacrylic acid copolymers, methacrylic ester copolymers, and ammonioalkyl methacrylate copolymers, and preferably wherein the polymer is selected from the group consisting of PLGAs and amino alkyl methacrylate copolymers.

A preferred embodiment relates to the composition of the first aspect, wherein the polymer of the nanoparticles is an ammonio methacrylate copolymer, preferably selected from Eudragit RS and/or Eudragit RL.

A preferred embodiment relates to the composition of the first aspect, wherein the composition further comprises at least an adjuvant selected from the group consisting of an anti-inflammatory agent, an immuno-stimulating agent, a CpG oligodeoxynucleotide, and a lipopolysaccharide (LPS).

A preferred embodiment relates to the composition of the first aspect, wherein the composition further comprises at least an adjuvant, and wherein the adjuvant is an anti-inflammatory agent, preferably wherein the anti-inflammatory agent is an NSAID; further preferably wherein the NSAID is a COX-1 and/or COX-2 inhibitor; still further preferably wherein the NSAID is selected from the group consisting of aspirin, choline and magnesium salicylates, choline salicylate, celecoxib, diclofenac potassium, diclofenac sodium, diclofenac sodium with misoprostol, diflunisal, etodolac, fenoprofen calcium, flurbiprofen, ibuprofen, indomethacin, ketoprofen, magnesium salicylate, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib, and combinations thereof; and still further preferably, wherein the NSAID is selected from the group consisting of aspirin, ibuprofen, celecoxib, and combinations thereof. With the use of an anti-inflammatory agent, preferably an NSAID, adverse effects, such as anaphylactic reactions, tissue necrosis, and the Shwartsman reaction, can be reduced or even suppressed. This, in turn, may allow for applying an increased dose of the composition of the present disclosure.

A preferred embodiment relates to the composition of the first aspect, wherein the composition further comprises at least an adjuvant, and wherein the adjuvant is an immuno-stimulating agent, preferably wherein the immuno-stimulating agent is selected from the group consisting of surface active compounds and/or their respective oil-in-water emulsions, e.g. saponins, polysorbates, monophosphoryl-lipid A, or lipids containing at least one quaternary ammonium group.

A preferred embodiment relates to the composition of the first aspect, wherein the composition further comprises at least an adjuvant, and wherein the adjuvant is a CpG oligodeoxynucleotide, wherein the CpG oligodeoxynucleotide has a sequence which is at least 90% identical to SEQ ID NO: 1, more preferably wherein the CpG oligodeoxynucleotide has a sequence selected from the group SEQ ID NO: 1.

A preferred embodiment relates to the composition of the first aspect, wherein the composition further comprises at least an adjuvant, and wherein the adjuvant is a lipopolysaccharide (LPS).

A preferred embodiment relates to the composition of the first aspect, wherein the composition is used for the treatment of cancer, preferably wherein the cancer is selected from the group consisting of breast cancer, gastric carcinoma, bladder cancer, colorectal cancer, pancreatic cancer, colon cancer, lung cancer, prostate cancer, gliomas and melanomas, still further preferably wherein the cancer is selected from the group consisting of breast cancer, colon cancer, lung cancer, prostate cancer, gliomas and melanomas, still further preferably wherein the cancer is colon cancer.

In a second aspect, the present disclosure relates to a composition as defined above in relation to the first aspect.

BRIEF DESCRIPTION OF THE DRAWINGS

FIG. 2. LPS release from the nanoparticles. Results are presented as mean±SD of three independent experiments.

FIG. 3. Dose-response curves for LPS vs. LPS-NP in macrophages (A) and DCs (B) along with the calculated LC50 values (C). Data are shown as the mean±SD of three independent experiments.

FIG. 5. A) Complete tumor remission after the administration of four doses of LPS/LPS-NP, B) investigation of cross-immunity through the injection of GL261 cells in the left flank of the mice previously recovered from synegeneic colorectal cancer, D) tumor growth following the inoculation of C26 cells in the right flank and biweekly injection of LPS-NP in the left flank of the mice. The results are presented as the mean±SD of the experiments on five different animals per each group.

FIG. 6. Serum cytokine levels at different time intervals following the peritumoral injection of the first dose of LPS/LPS-NP. Results are presented as mean±SD of three independent experiments.

FIG. 9. Dose-response curves for $4 \times 10^5$ macrophages (A) and DCs (B) treated with LPS-decorated nanostructures along with the calculated LC50 values (C). (E) LC50 values based on matrix concentration for the LPS-free and LPS-based nanostructures. Results are presented as mean±SD of three independent experiments.

FIG. 10. (A) Uptake and binding levels of LPS-decorated nanostructures by macrophages and DCs, (B) mechanism of the internalization of LPS-free and LPS-decorated nanostrcutures by RAW 264.7 macrophages. Results are presented as mean±SD of five independent experiments.

FIG. 11. Caspase 3 levels within the cell debris following the overnight incubation of the C26 tumor-splenocyte co-culture with 30 μg/mL of LPS, LPS-NP (100 nm), LPS-NP (700 nm), LPS-NE, or the corresponding concentrations of PLGA (LPS-free) and NE (LPS-free). The results are presented as the mean±SD of three independent experiments.

FIG. 12. Survival analysis (left) and tumor volume (right) in C26 tumor-bearing mice (n=5) treated with biweekly peritumoral injections of PBS (control), LPS-decorated nanostructures and LPS-free control nanostructures. Compared to the LPS-treated group, a significant increase of animals' survival was observed in case of LPS-NE.

FIG. 13. Tumor volume following the biweekly treatment of C26 tumor-bearing mice with peritumoral injections of different LPS-decorated and LPS-free control nanostructures.

FIG. 15. Toxicity of AMCNPs for the macrophages (A) and DCs (B) along with the calculated LC50 values (C). Results are presented as the mean±SD of three independent experiments.

FIG. 16. Induction of different pro-inflammatory cytokines including TNF-α (A), IL-6 (B), IL-1β (C), IL-12p40 (D) and IFN-γ (E) following the overnight incubation of $4 \times 10^6$ RAW 264.7 and JAWS II DCs with various concentrations of AMCNPs. (F) Significant decrease of TNF-α induction following the inhibition of endocytosis and active uptake in RAW 264.7 macrophages. Results are shown as the mean±SD of three independent experiments.

FIG. 17. Cellular NF-κB levels following overnight incubation of RAW Blue cells with 100 μg/mL of different AMCNPs. PMB (10 μg/mL) or CLI-095 (3 μg/mL) were used in analogous parallel experiments to neutralize the potential endotoxin contamination and to block the TLR4 signaling, respectively. Results are presented as the mean±SD of five independent experiments.

FIG. 18. (A) Concentrations of the pro-inflammatory and immunosuppressive cytokines and chemokines within the supernatant of C26-splenocyte co-culture incubated overnight with 30 μg/mL of AMCNPs. (B) Cellular Caspase 3 levels in C26-splenocyte co-culture incubated overnight with 30 μg/mL of AMCNPs. Results are presented as mean±SD of three independent experiments.

FIG. 19. Tumor size and survival analysis of the C26 tumor-bearing mice (n=5) treated with peritumoral injections of 10 mg/mL AMCNPs. Survival of the animals was investigated based on the time required for the tumor to reach a volume of 1000 mm$^3$ (A), where a significant increase was observed for all groups compared to the control. In one case, the animal in RLNP-700 nm group was euthanized due to the occurrence of severe necrosis in the tumor site (D). Additionally, tumor volume versus number of injected doses both as average values (B) and as single values for the individual mice in each group is depicted (C-1 to C-5).

FIG. 20. Tumor size and survival analysis of the C26 tumor bearing mice (n=5) treated with peritumoral injections of 100 mg/mL AMCNPs. Survival of the animals was investigated based on the time required for the tumor to reach a volume of 1000 mm$^3$ (A), where a significant increase was observed for all groups compared to the control. Throughout the treatment, internal or external necrosis at the tumor site was only observed in three animals, two in the RSNP-100 nm group (D-1 and D-2) and one in RLNP-700 nm group (D-3).

FIG. 21. Cellular Caspase 3 levels in C26 (A) and GL261 (B) cells incubated overnight with the splenocytes isolated from the mice treated with PBS (control group) or different types of AMCNPs. Results are presented as mean±SD of three independent experiments for the splenocytes isolated from two different mice in each group.

FIG. 22. Semi-quantitative determination of apoptosis within the TUNEL-stained tumor cross sections presented as the average percentage of the stained surface area in 10 fields captured from various areas of three tumor cross sections.

FIG. 23. A) Due to the interaction of the free LPS with the AMC matrix, LPS release from the nanoparticles was not distiguishable. Instead, a decrease in free LPS concentration was observed overtime. B) The intraction between the free LPS and the remaining polymeric matrix resulted in the formation of aggregate-like structures becoming visible 48 h after the initiation of the release experiments. Such aggregates were of course not present when LPS-free AMCNPs were incubated in PBS under the same conditions and for the same duration (C).

FIG. 24. Toxicity of LPS, RL-LPS, and RS-LPS for macrophages (A) and DCs (B) along with the calculated LC50 values (C). Results are presented as the mean±SD of three independent experiments.

FIG. 25. Cytokine induction profiles following the overnight incubation of RAW 264.7 macrophages and JAWS II DCs with LPS, RS-LPS, RL-LPS, RSNP, and RLNP (LPS concentration 30 μg/mL, AMCNP concentration 150 μg/mL).

FIG. 26. NF-κB induction in RAW Blue cells treated with LPS, RS-LPS, RL-LPS, RLNP, RSNP, and the mixtures of LPS with RLNP or RSNP for 6 h. The concentration of LPS and AMCNPs were set at 30 and 150 μg/mL, respectively. Results are presented as fold compared to control and as the mean±SD of five independent experiments.

FIG. 27. Caspase 3 levels in C26-splenocyte co-culture treated overnight with LPS, RL-LPS, RS-LPS, RLNP and RSNP. Results are presented as the mean±SD of three independent experiments.

FIG. 28. Concentrations of the pro-inflammatory and immunosuppressive cytokines and chemokines within the supernatant of C26-splenocyte co-culture incubated overnight LPS, RL-LPS, RS-LPS, RLNP and RSNP. Results are presented as mean±SD of three independent experiments.

FIG. 29. Tumor volume in C26 tumor-bearing mice (n=5) receiving biweekly injections of PBS (control), LPS (100 μg/mL), RL-LPS (100 μg/mL and 10 mg/mL of LPS and type A AMC, respectively), RS-LPS (100 μg/mL and 10 mg/mL of LPS and type B AMC, respectively), RLNP (10 mg/mL), and RSNP (10 mg/mL).

FIG. 30. Survival analysis of the C26 tumor-bearing mice (n=5) treated with PBS (control), LPS (100 μg/mL), RL-LPS (100 μg/mL and 10 mg/mL of LPS and type A AMC, respectively), RS-LPS (100 μg/mL and 10 mg/mL of LPS and type B AMC, respectively), RLNP (10 mg/mL), and RSNP (10 mg/mL). Compared to the LPS-treated group, a significant increase of the animals' survival was observed in case of RL-LPS, RLNP and RSNP.

DETAILED DESCRIPTION OF THE INVENTION

Figure 1:
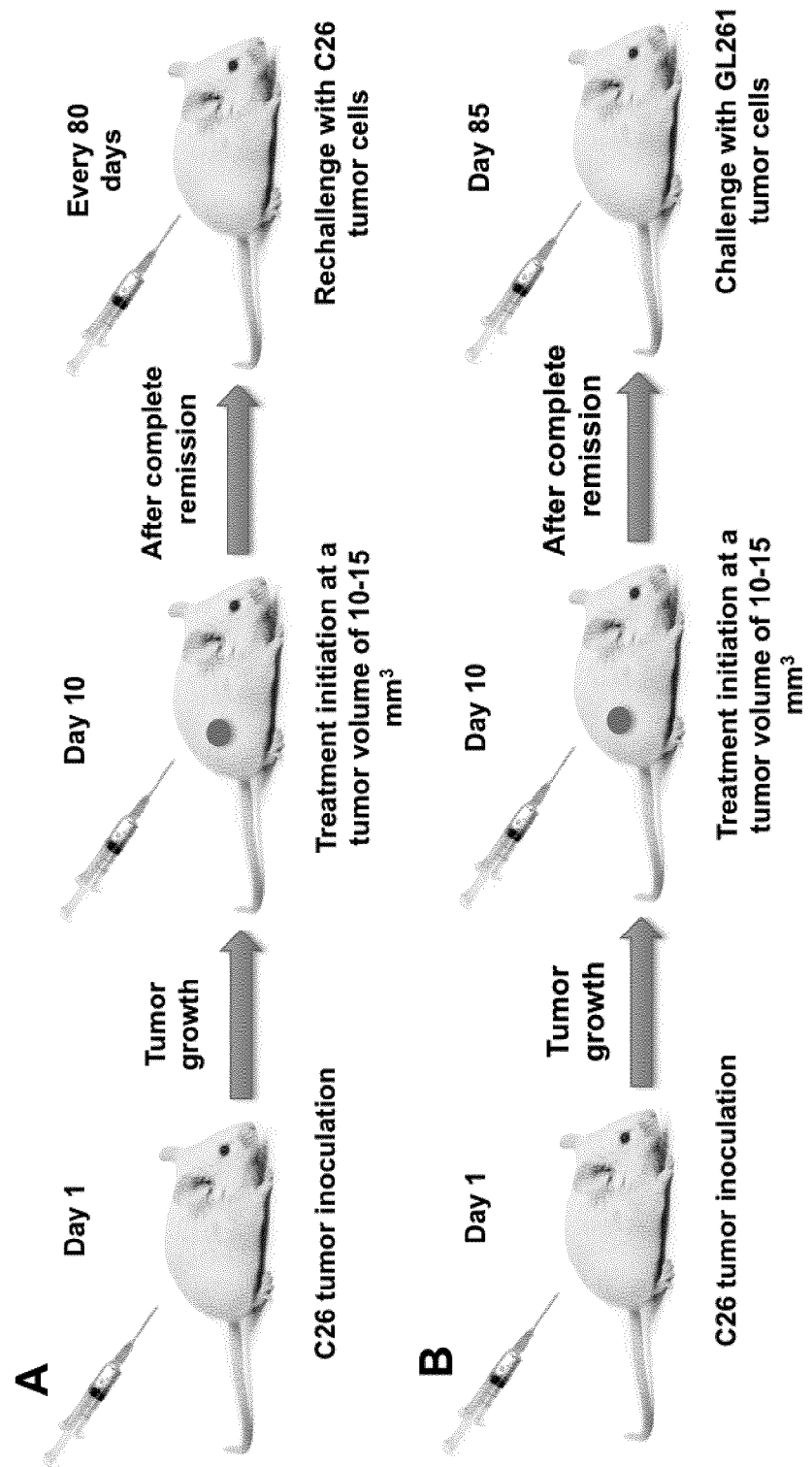
FIG. 1. Schematic of the animal trials. Surviving mice were either rechallenged with three further injections of C26 cells (A), or with a single injection of GL261 cells to which they had had no previous encounter.

The present invention as illustratively described in the following may suitably be practiced in the absence of any element or elements, limitation or limitations not specifically disclosed herein. The present invention will be described with respect to particular embodiments and with reference to certain figures but the invention is not limited thereto but only by the claims. Terms as set forth hereinafter are generally to be understood in their common sense unless indicated otherwise.

Definitions

As used herein, "nano-particles" or "nanoparticles", also termed as "NP" or "NPs", are particles having a particle size of below 1000 nm, preferably below 800 nm. The nanoparticles may have a size of at least 10 nm, preferably at least 50 nm, or at least 80 nm. The nano-particles in a solvent may be primary particles, or agglomerated particles composed of smaller particles. To determine the particle size, photon correlation spectroscopy and electrophoretic laser doppler anemometry may be used, respectively. Particle size may be measured in terms of effective diameter and polydispersity index (PDI) using particle size/zeta analyzer (Brookhaven Instruments, NY, USA) at a fixed angle of 90° at 25° C. Alternatively, the particle size in the nanosuspension may be measured with a laser diffraction analyzer (e.g. Horiba SZ-100).

The terms "(meth)acrylate" or "(meth)acrylic" are meant to designate in the present application both acrylate and methacrylate as well as derivatives thereof or mixtures thereof. Thus, the term may refer to acrylate or methacrylate, or both. Preferred acrylates or methacrylates are the methyl, ethyl, n-propyl, iso-propyl, n-butyl, iso-butyl, tert-butyl, and dimethylaminomethly esters of acrylic or methacrylic acid, respectively.

The terms "(meth)acrylic acid" is thus meant to designate in the present application both acrylic acid and methacrylic acid, as well as derivatives thereof or mixtures thereof.

The term "poly(meth)acrylate" refers to homo- or co-polymers comprising at least one (meth)acrylate. In a preferred embodiment, the poly(meth)acrylate is a co-polymer of at least one (meth)acrylate and (meth)acrylic acid. Particularly preferred poly(meth)acrylates are polymethacrylates as outlined in the Handbook of Pharmaceutical Excipients, 5$^{th}$ edition, Pharmaceutical Press, 2006, pages 553-560, which is incorporated herein in its entirety. Also preferred are the different Eudragit® grades, in particular Eudragit RL and Eudragit RS.

"$(C_1-C_6)$alkyl" means a straight chain or branched non-cyclic hydrocarbon having from 1 to 6 carbon atoms. Representative straight chain $(C_1-C_6)$alkyls include methyl, ethyl, n-propyl, n-butyl, n-pentyl, and n-hexyl. Representative branched $(C_1-C_6)$alkyls include iso-propyl, sec-butyl, iso-butyl, tert-butyl, iso-pentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethtylbutyl, 1,2-dimethylbutyl, 1,3-dimethylbutyl, 2,2-dimethylbutyl, 2,3-dimethylbutyl, and 3,3-dimethylbutyl.

"$(C_1-C_4)$alkyl" means a straight chain or branched non-cyclic hydrocarbon having from 1 to 4 carbon atoms. Representative straight chain $(C_1-C_4)$alkyls include methyl, ethyl, n-propyl, and n-butyl. Representative branched $(C_1-C_4)$alkyls include iso-propyl, sec-butyl, iso-butyl, and tert-butyl.

"$(C_1-C_3)$alkyl" means a straight chain or branched non-cyclic hydrocarbon having from 1 to 3 carbon atoms. Representative straight chain $(C_1-C_3)$alkyls include methyl, ethyl, and n-propyl. Representative branched $(C_1-C_3)$alkyls include iso-propyl.

"$(C_1-C_2)$alkyl" means a straight chain non-cyclic hydrocarbon having 1 or 2 carbon atoms. Representative straight chain $(C_1-C_2)$alkyls include methyl and ethyl.

The term "alkyl" when used without any further indication of the number of carbon atoms refers to a $(C_1-C_6)$alkyl, preferably a $(C_1-C_4)$alkyl, further preferably a $(C_1-C_3)$alkyl, still further preferably a $(C_1-C_2)$alkyl.

The term "amino alkyl" means any of the above defined alkyls, wherein one hydrogen atom is replaced by amino ($-NR^xR^y$) group, $R^x$, and $R^y$ are, independently of each other, selected as hydrogen or alkyl. In other words, amino alkyl refers to -alkyl-$NR^xR^y$. In a preferred embodiment, $R^x$ and $R^y$ are each selected as hydrogen or methyl.

The term "ammonio alkyl" refers to an alkyl group as defined above, wherein one hydrogen atom is replaced by an ammonio group, i.e., the alkyl contains a quaternary ammonium group ($-NR^aR^bR^{c+}A^-$). $R^a$, $R^b$, and $R^c$ are, independently of each other, selected as alkyl. In a preferred embodiment, $R^a$, $R^b$, and $R^c$ are each methyl. A is selected form the group consisting of phosphate, sulfate, F, Cl, Br, and I, and preferably is Cl. In a particularly preferred embodiment, ammonio alkyl is $-CH_2CH_2N(CH_3)_3Cl$.

The term "AMCs" refers to ammonio alkyl methacrylate copolymers.

The term "AMCNPs" refers to nano-particles wherein the polymer comprises or consists of at least one ammonio alkyl methacrylate copolymer (AMC).

The term "RSNP" refers to nano-particles prepared from an Eudragit® RS grade.

The term "RLNP" refers to nano-particles prepared from an Eudragit® RL grade.

"Poly Lactic Acid (PLA)" is a polymer of lactic acid, which may be produced, e.g., from the polymerization of lactic acid, and the cyclic di-ester, lactide.

"Polycaprolactone (PCL)" is a polymer which may, e.g., be prepared by ring opening polymerization of ε-caprolactone using a catalyst such as stannous octoate.

"Polyglycolic acid (PGA)", also termed polyglycolide, is a polymer prepared from glycolic acid.

"Poly Lactic-co-Glycolic Acid (PLGA)" is a copolymer of poly lactic acid (PLA) and poly glycolic acid (PGA), also comprising their PEG containing block copolymers. PLGA is synthesized by means of ring-opening co-polymerization of two different monomers, the cyclic dimers (1,4-dioxane-2,5-diones) of glycolic acid and lactic acid. Polymers can be synthesized as either random or block copolymers thereby imparting additional polymer properties. It is the best defined biomaterial available for drug delivery with respect to design and performance. Poly lactic acid contains an asymmetric α-carbon which is typically described as the D or L form in classical stereochemical terms and sometimes as R and S form, respectively. The enantiomeric forms of the polymer PLA are poly D-lactic acid (PDLA) and poly L-lactic acid (PLLA). PLGA is generally an acronym for poly D,L-lactic-coglycolic acid where D- and L-lactic acid forms are in equal ratio. Further reference may be made to Polymers (Basel). 2011 Sep. 1; 3(3): 1377-1397, which is herein incorporated in its entirety by reference.

As used herein, the term "lipopolysaccharide", also termed as "LPS", also known as lipoglycans and endotoxins, refers to large molecules consisting of a lipid and a polysaccharide composed of O-antigen, outer core and inner core joined by a covalent bond; they are found in the outer membrane of Gram-negative bacteria. LPS thus refers to a native, i.e., isolated from natural material or synthetically produced having a native structure, or a modified lipopolysaccharide of a bacterial cell wall. LPS may thus have different origin, however, preferably the LPS is of microbial origin, e.g., from *Escherichia coli, Salmonella enterica* or *Pseudomonas aeruginosa*. Other types of LPS may also be used for the purposes of the present disclosure.

As used herein, the term "cancer" refers to a group of diseases involving abnormal cell growth with the potential to invade or spread to other parts of the body. This includes cancers derived from epithelial cells (carcinomas), including many of the most common cancers, such as cancers in the breast, prostate, lung, pancreas and colon. Also included by the term cancer is a sarcoma, i.e., cancers arising from connective tissue (bone, cartilage, fat, nerve), each of which develops from cells originating in mesenchymal cells outside the bone marrow, and lymphoma and leukemia, i.e., cancers arising from hematopoietic (blood-forming) cells that leave the marrow and tend to mature in the lymph nodes and blood, respectively.

The term "treatment" as used herein in connection with cancer, in particular with carcinomas, relates to a reduction or stop of the tumor growth, or, in more general terms, reduction or stop of the progression of the disease cancer. This includes the reduction of the primary tumor and/or any secondary tumor (metastasis), up to complete remission of the tumor.

The term "controlled" or "sustained" release relates to a controlled- or sustained-release pharmaceutical compositions wherein the active agent, such as an adjuvant as described herein, in particular LPS, from the nanoparticles. A controlled or sustained release can have a common goal of improving drug therapy over that achieved by their non-controlled or non-sustained-release counterparts. In one embodiment, a controlled- or sustained-release composition comprises a minimal amount of an adjuvant to treat or prevent the Disease or a symptom thereof in a minimum amount of time. Advantages of controlled- or sustained-release compositions include extended activity of the adjuvant, reduced dosage frequency, and increased compliance. In addition, controlled- or sustained-release compositions can favorably affect the time of onset of action or other characteristics, such as blood levels of the adjuvant, and can thus reduce the occurrence of adverse side effects. Controlled- or sustained-release compositions can initially release an amount of an adjuvant that promptly produces the desired therapeutic or prophylactic effect, and gradually and continually release other amounts of the adjuvant to maintain this level of therapeutic or prophylactic effect over an extended period of time. To maintain a constant level of the adjuvant, such as LPS, in the body, the adjuvant can be released from the nanoparticle at a rate that will replace the amount of adjuvant being metabolized and excreted from the body. The controlled- or sutained-release compositions comprising an adjuvant may also have reduced side effects compared to the free adjuvant.

As used herein, the terms "comprise/comprising" and "e.g./for example" are not to be construed in a limiting manner. However, according to a preferred embodiment, the terms "comprise/comprising" are to be understood as limiting, i.e., they may be replaced by "consist of/consisting of".

The term "about" as used herein refers to a range around the given value of ±10%, preferably ±5%, further preferably ±2%, and still further preferably ±1%.

The use of the singular terms "a", "an" and "the"—in general—also comprise the plural. However, in a preferred embodiment, these terms are used as limiting to the singular.

The term "therapeutic agent" as used herein refers to an agent or drug which shows activity in a mammal for the treatment, preferably therapeutic treatment, in a mammal, such as a human. Exemplary therapeutic agents may include, but are not limited to, small molecules (e.g., cytotoxic agents or anti-inflammatory agents), nucleic acids (e.g., siRNA, RNAi, and mircoRNA agents), proteins (e. g. antibodies), peptides, lipids, carbohydrates, hormones, metals, radioactive elements and compounds, drugs, vaccines, immunological agents, etc., and/or combinations thereof. In the context of the present application, LPS is not considered as a therapeutic agent.

Nanoparticles

The composition for use as a medicament as disclosed herein comprise nanoparticles, also termed as NPs, wherein the nanoparticles comprise a polymer selected from the group consisting of PLGA and poly(meth)acrylates. In other words, the nanoparticles comprise or consist of at least one polymer, preferably one polymer, which is selected from a PLGA and a poly(meth)acrylate. In a preferred embodiment of the present disclosure, the nanoparticles comprise one polymer selected from PLGA and a poly(meth)acrylate.

PLGA Nanoparticles

In one embodiment, the nanoparticles of the present disclosure comprise or consist of one polymer, wherein the polymer is a PLGA. Apart from the polymer in the nanoparticle, the nanoparticle may comprise other components, in particular at least one adjuvant.

For the purposes of the present disclosure, nanoparticles of PLGA may be prepared by techniques known to the skilled person. This includes, e.g., a solvent displacement method, comprising the dissolution of PLGA in a solvent, such as polyethylene glycol 400, to form a solution of PLGA, and the subsequent addition of this PLGA solvent solution to deionized water under constant stirring. The resulting PLGA particles may then be washed with water to dispose the initial solvent.

Corresponding LPS containing PLGA nanoparticles may be prepared, e.g., by oil in water emulsification/solvent evaporation technique. After dissolving PLGA in a solvent, such as ethyl acetate, the resulting PLGA solution may be poured into an aqueous LPS solution. Additionally, the emulsion may be subjected to high sheer forces, such as in an ultrasonic cell disruptor. After removal of the organic solvent, such as ethyl acetate, a suspension of LPS containing PLGA nanoparticles is obtained.

Poly(meth)acrylate Nanoparticles

In one embodiment, the nanoparticles of the present disclosure comprise or consist of one polymer, wherein the polymer is a poly(meth)acrylate. Apart from the polymer in the nanoparticle, the nanoparticle may comprise other components, in particular at least one adjuvant.

The poly(meth)acrylate is a homo- or co-polymer of at least one (meth)acrylate. If the polymer is a homopolymer, a single (meth)acrylate is used to prepare the poly(meth)acrylate. If the polymer is a co-polymer, at least two different (meth)acrylates, or at least one (meth)acrylate and (meth)acrylic acid are used to prepare the co-polymeric poly(meth)acrylate. Preferred acrylates or methacrylates used in the poly(meth)acrylate are the alkyl, amino alkyl, or ammonio alkyl (meth)acrylates. The term "alkyl" in this connection relates to methyl, ethyl, n-propyl, iso-propyl, n-butyl, iso-butyl, and tert-butyl, and dimethylaminomethly esters of acrylic or methacrylic acid, respectively.

In a preferred embodiment, the poly(meth)acrylate is a polymer of the following structure:

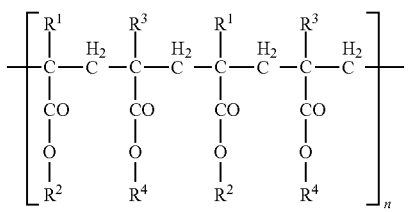

wherein:

$R^1$, $R^1$, $R^3$ and $R^4$ are, independently of each other, selected from the group consisting of hydrogen, $(C_1-C_6)$ alkyl, amino alkyl and ammonioalkyl.

In a further preferred embodiment, $R^1$ is selected from hydrogen and methyl, and $R^3$ is methyl, $R^2$ is selected from hydrogen and $(C_1-C_4)$alkyl, and $R^4$ is selected from hydrogen, methyl, ethyl, butyl, —$CH_2CH_2N(CH_3)_2$ and —$CH_2CH_2N(CH_3)_3{}^+Cl^-$.

In a preferred embodiment, the poly(meth)acrylate is a polymethacrylate, i.e., a polymer of at least one methacrylate. In a further preferred embodiment, the poly(meth)acrylate is selected from the group consisting of amino alkyl methacrylate copolymers, methacrylic acid copolymers, methacrylic ester copolymers, and ammonio alkyl methacrylate copolymers (AMCs), wherein alkyl is a $(C_1-C_6)$alkyl, preferably a $(C_1-C_4)$alkyl, further preferably a $(C_1-C_2)$alkyl.

In a preferred embodiment the poly(meth)acrylate is an ammonio alkyl methacrylate co-polymer of ethyl acrylate, methyl methacrylate, and trimethylammonioethyl methacrylate chloride in the molar ratio of 1:2:0.2, or in the molar ratio of 1:2:0.1.

Particularly preferred poly(meth)acrylates are polymethacrylates as outlined in the Handbook of Pharmaceutical Excipients, 5$^{th}$ edition, Pharmaceutical Press, 2006, pages 553-560, which is incorporated herein in its entirety. Also preferred are the different Eudragit® grades, in particular Eudragit RL and Eudragit RS.

Nano-particles of poly(meth)acrylates may be prepared by methods known to the skilled person. As an example, the poly(meth)acrylate powder may be dissolved in a solvent, such as ethyl acetate, acetone, or a mixture thereof. The resulting organic phase may then be subjected to high sheer and the addition of water. Subsequently, the organic solvents are removed to result in an aqueous suspension of nanoparticles.

Nano-particles of ammonio alkyl methacrylate copolymers (AMCs) are termed herein as AMCNPs.

Lipid Nanoparticles

In one embodiment, the nanoparticles of the present disclosure comprise or consist of one lipid, such as fats, waxes, sterols, fat-soluble vitamins (such as vitamins A, D, E, and K), monoglycerides, diglycerides, triglycerides, and phospholipids. Apart from the lipid in the nanoparticle, the nanoparticle may comprise other components, in particular at least one adjuvant. The lipid is considered as a polymer in relation to this disclosure.

In a preferred embodiment, the lipid may be selected from the group consisting of fatty acids, glycerolipids, glycerophospholipids, sphingolipids, sterol lipids, prenol lipids, saccharolipids, and polyketides. Further preferred, the lipid is a glycero lipid, still further preferred a monoglyceride, diglyceride, or triglyceride, in particular triglycerides, preferably medium-chain triglycerides.

Characterization

Without being bound to a theory, it is assumed that the size, and possibly also the size distribution, of the nanoparticles has an influence on the distribution in an organism, and also, if present, the release of an associated adjuvant. As such, the nanoparticles may be used to influence the release of the adjuvant, and the adjuvant may be released in a controlled or sustained manner.

The methods given in the following for determining the size of the particles may be applied to all particles mentioned herein, in particular for the nanoparticulate compositions. The size determination may be achieve, inter alia, by photon correlation spectroscopy, determining the hydrodynamic diameter of the particles via the diffusion speed of the particles (Brownian motion). A further method is the laser diffraction.

Since usually not all particles of a sample have the exactly same size, the results are given, e.g., in the form of a volumetric diameter or size of particles. The $d_{50}$ refers to the mean particle size where 50% of the particles are smaller than the given value. If not indicated differently, the particle sizes of the present disclosure refer to the $d_{50}$.

The polydispersity index (PDI), which may also be determined via laser diffraction methods, relates to the size distribution of the particles. For the purposes of the present disclosure, the PDI may be determined on a particle size/zeta analyzer (Brookhaven Instruments, NY, USA) at a fixed angle of 90° at 25° C.

Adjuvants

In a preferred embodiment of the present disclosure, the composition further comprises at least an adjuvant selected from the group consisting of an anti-inflammatory agent, an immuno-stimulating agent, a CpG oligodeoxynucleotide, and a lipopolysaccharide (LPS).

The inventors surprisingly found that the combination of the nanoparticles as disclosed herein with an adjuvant may advantageously influence the TLR activation of the nanoparticles. In particular advantageous appears to be the use of an anti-inflammatory agent, an immune-stimulating agent, a CpG oligodeoxynucleotide, or a lipopolysaccharide. Also advantageous are adjuvants reducing the necrotic or inflammatory side effects of the nanoparticles, further preferably without affecting the TLR activity of the nanoparticles. It is also preferred to use at least two different adjuvants, in particular at least an anti-inflammatory agent and a lipopolysaccharide in combination.

In a preferred embodiment, the adjuvant is released from the nanoparticles in a controlled manner allowing for the adjustment of the adjuvant concentration over a prolonged period of time. In a particular preferred embodiment, the adjuvant is LPS, and further preferably, the LPS is released in a controlled manner over a period of at least 5 hours, further preferably over at least 8 hours, still further preferably over at least 10 hours, and still further preferably over at least 15 hours. It is still further preferred that, in addition to the adjuvant LPS, a further adjuvant selected from an anti-inflammatory agent is present in the composition.

In another preferred embodiment, the adjuvant is released from the nanoparticles in a controlled manner, wherein the adjuvant is released in-vitro in an amount of about 10% to about 60% after 1 hour, in an amount of about 20% to about 80% after 2 hours, and in an amount of about 30% to about 90% after 4 hours.

In another preferred embodiment, the nanoparticle is PLGA and the adjuvant is LPS, and the adjuvant is released from the nanoparticles in a controlled manner, wherein the adjuvant is released in-vitro in an amount of about 10% to about 60% after 1 hour, in an amount of about 20% to about 80% after 2 hours, and in an amount of about 30% to about 90% after 4 hours.

Method of Treatment

The compositions of the present disclosure are useful in the treatment of cancer. The present disclosure thus relates to compositions for the use in the manufacture of a medicament. In particular, the present disclosure relates to compositions for the use in the treatment or prevention of cancer.

Furthermore, the present disclosure relates to a method of treatment or prevention of a disease, comprising administering a composition or nanoparticle of the present disclosure to a patient in need thereof. In a preferred embodiment, the disease is a cancer.

The present disclosure also relates to the use of the compositions disclosed herein for the manufacture of a medicament. In a preferred embodiment, the present disclosure relates to the use of a composition as disclosed herein for the treatment or prevention of cancer.

In a preferred embodiment of all aspects described above, the cancer is selected from the group consisting of breast cancer, gastric carcinoma, bladder cancer, colorectal cancer, pancreatic cancer, colon cancer, lung cancer, prostate cancer, gliomas and melanomas; still further preferably the cancer is selected from the group consisting of breast cancer, colon cancer, lung cancer, prostate cancer, gliomas and melanomas; and still further preferably the cancer is colon cancer.

The compositions of the present disclosure may be applied in any pharmaceutically feasible way known to the person skilled in the art. As such, the composition may be applied in an intravenous, subcutaneous, intradermal, intramuscular, intraperitoneal, parenteral, oral nasal buccal, rectal, vaginal or topical manner. Preferred is an injection in or around the tumor, i.e., an intratumoral or peri-tumoral injection, such as in the regional vessel or lymph system, or in the former tumor bed. Another preferred route of administration is the intravenous (IV) injection of the compositions of the present disclosure.

The composition of the present disclosure may be release in different ways according to its formulation. In particular for adjuvants associated to nanoparticles, an immediate or controlled release of the adjuvant is intended.

In a preferred embodiment of the present disclosure, different application schemes may be used. The cancer, such as a tumor, may, e.g., be treated on a weekly or monthly basis. Preferably, the treatment is applied once or twice a week, and it may comprise different concentrations of the composition. Different concentrations of the composition may comprise different concentrations of nanoparticles and/or adjuvants in the composition. In a preferred embodiment, the treatment comprises 100 µg to 100 mg of nanoparticles/kg body weight per administered dose. The treatment with the compositions of the present disclosure may also be combined with hitherto known conventional methods of cancer treatment, such as surgery, chemotherapy, gene therapy, or radiotherapy as long as the immune response by the body is not compromised. This treatment may be applied simultaneously with the conventional treatment, or separately, i.e., prior or after the conventional treatment, within minutes, hours, days, weeks or months.

Treatment with Nanoparticles

Nanoparticles were shown to be a platform for active immunotherapy in cancer, for in addition to the general immunomostimulatory properties associated with their specific range of particle size, they can be purposefully engineered to modulate the immune system (see Example 3). Though often regarded as well-established inactive ingredients for oral dosage forms, formulation of AMCs as nanoparticles show immunotherapeutic effects. As demonstrated, a purposeful manipulation of the nanoparticle physicochemical characteristics such as size and surface charge allows the optimization of cytokine induction profile as well as the eventual immunotherapeutic outcome. So promising is the AMCNP-triggered pro-inflammatory approach for cancer immunotherapy that treatment with cargo-free nanoparticles is shown to result in a significant retardation of the tumor growth and in several cases complete tumor remission.

It is thus particularly preferred to use a composition comprising or consisting of nanoparticles consisting of ammonio alkyl methacrylate copolymers (AMCs), i.e., AMCNPs, wherein the nanoparticles are free of other materials, such as therapeutic agents, especially for the treatment of cancer. In a preferred embodiment, the composition consists of a solvent for dispersing the nanoparticles, and the AMCNPs, preferably wherein the solvent is a pharmaceutically acceptable aqueous solution, optionally comprising buffering agents and/or isotonic agents. In a particularly preferred embodiment, the AMC is an Eudragit® grade, in particular Eudragit® RL and/or Eudragit® RS.

It is also preferred according to the present disclosure to use a combination of LPS, nanoparticles and at least one further adjuvant selected from an anti-inflammatory agent (preferably an NSAID), an immuno-stimulating agent, and a CpG oligodeoxynucleotide for the treatment of cancer. It is also preferred according to the present disclosure to use a combination of LPS, nanoparticles and an anti-inflammatory agent (preferably an NSAID). It is further preferred that no other therapeutic agent is used during said treatment.

LPS Containing PLGA Nanoparticles

The inventors introduce a novel nanoparticle-based approach for the optimization of the LPS-associated efficiency and adverse effects. Without being bound to any theory, it is hypothesized that the incorporation of an adjuvant, such as LPS molecules, into a nanosized structure can influence their conduct at the cellular and molecular levels, for the size of the system on one hand and the complicated interplay of the molecule with the polymeric matrix and the cellular receptors on the other can impact the ultimate biological response. Rather than regarding the system as a mere means of transportation for the delivery of an adjuvant, such as LPS molecules, the inventors incorporated, e.g., LPS as a structural component of the developed immunotherapeutic system. Also, nanoparticles can serve as reservoirs of adjuvants, such as LPS molecules, decelerating their intracorporeal release (particularly within the subcutaneous setting) and reducing the possibility of severe immunological reactions. Further, the immunostimulatory properties of the nanoparticles can be optimized through the manipulation of particle physicochemical characteristics (e.g. size, surface charge, composition and hydrophobicity).

As an exemplary embodiment, LPS-NPs were formulated with a size of around 150 nm and a negative zeta potential value (related to the combined negative charge of the PLGA particle matrix and the LPS molecules), spherical morphology and acceptably high LPS incorporation (around 70%), as detailed in Example 1. Due to the superficial localization of the LPS molecules, they were released in a controlled manner within the first 8 hours of the in vitro release test.

Compared to pure LPS, nanoparticles were shown to have reduced toxicity for the immune cells in vitro, though as the in vivo experiments demonstrated, the nanoparticle-associated reduction of LPS toxicity is much more significant. Firstly, the particles are directly subjected to an aqueous environment during the cell culture experiments which results in the release of a substantial amount of the superficially bound LPS, whereas in vivo, the subcutaneous injection conditions relatively decelerates the release profile. Second, LPS-induced in vivo toxicity is often a byproduct of the molecules' significant immunostimulatory properties, which results in the dysbalance of pro- and anti-inflammatory forces, and which the in vitro models fail to mirror.

In addition to the toxicity profile, the pattern of in vitro cytokine induction was impacted once LPS was incorporated into the nanoparticulate matrix. In particular, a significant increase of TNF-α and IL-6 was observed under the effect of LPS-NP compared to pure LPS solution. The cellular NF-κB induction was assessed to serve as a measure for the comparison of the overall immunostimulatory response between the two systems LPS-NP and LPS solution. Here, a higher induction of the transcription factor was observed in the cells treated with nanoparticle formulation, signifying higher overall immunostimulatory properties. The in vivo cytokine induction, however, followed a different trend. Within the early hours following the injection, LPS-NP resulted in a higher induction of pro-inflammatory cytokines (except for IL-6). This can be related to the pathogen-mimicking properties of LPS-NP, which result in a faster attraction of the APCs to the site of injection. Nevertheless, given the lower rate of LPS release within the following hours (which restricts the availability of lipid A moiety for interaction with TLR4) LPS was associated with higher cytokine induction henceforth. This modulation of the cytokine induction pattern is essential for a better control of the immunological reactions and the associated undesirable side effects and will be discussed later in detail. On the other hand, with the exception of an early increase, both LPS and LPS-NP brought about a significant reduction of serum IL-6 levels compared to the untreated cancerous control. Although a potent pro-inflammatory cytokine in nature, IL-6 has been shown to be involved in tumor progression and malignant transformation processes and its decrease might correspond to the breakage of tumor-induced immune tolerance.

In vitro investigation of the antitumor efficiency in C26-splenocyte co-culture revealed the nanoparticles to be superior inducers of apoptosis, as evident from the higher induction of caspase 3 levels and the significant increase in the number of early apoptotic tumor cells. While treatment with 1000 μg/mL of LPS-NP accounted for remission in all animals, the same LPS dosage as solution led to severe localized necrosis. The necrosis did not manifest on the day of treatment, but commenced to appear 24-72 h following the first LPS injection. This confirms that it is the incorporation of the LPS in the nanoparticle structure that moderates the localized necrotic side effects.

The inventors also demonstrated that the localized injection at the tumor site is helpful to obtain maximum therapeutic efficiency. This is supported by the fact that subcutaneous injection of the nanoparticles at the opposite flank could merely retard the tumor growth. The localized immune activation offers a number of advantages such as redirecting the immune response toward the tumor site (where a large reservoir of tumor antigens are in hand), breaking the immune tolerance within the tumor site, and alleviating the undesirable systemic side effects. Amongst these, peritumoral injection has been proposed as a superior alternative to intratumoral injection for the administration. The peritumoral administration can ensure the localized activation of the immune response, while maximizing the summons of the immune cells from the surrounding tissues.

Incorporation of LPS in the nanoparticle structure was shown to improve the therapeutic outcome of LPS-based active immunotherapy in cancer. The particles modulated the cytokine induction pattern, increased the attraction of the macrophages toward the tumor site, resulted in a significant reduction of the therapeutic side effects, and offered the possibility of dose escalation.

LPS Containing AMC Nanoparticles

The inventors demonstrated an enhanced tolerability and immunotherapeutic potential of the TLR4 agonist LPS when incorporated within the structure of AMC-based nanoparticles with inherent TLR4 stimulatory properties. Formulation of the nanoparticles allows for the administration of LPS and AMC as a single immunotherapeutic entity, while enhancing the immunotherapeutic potentials and reducing the LPS-induced systemic side effects. Thus, the system with double TLR4 agonists can significantly improve the outcome of cancer active immunotherapy. Without being bound to any theory it is believed that a controlled release of LPS from the nanoparticle reduces the side effects of LPS.

It is thus particularly preferred to use a composition comprising or consisting of nanoparticles consisting of ammonio alkyl methacrylate copolymers (AMCs), i.e., AMCNPs, in combination with LPS, however, wherein the nanoparticles are free of other materials, such as therapeutic agents, especially for the treatment of cancer. In the context of the present application, LPS is not considered as a therapeutic agent. In a preferred embodiment, the composition consists of a solvent for dispersing the nanoparticles, LPS and the nanoparticles, preferably wherein the solvent is a pharmaceutically acceptable aqueous solution, optionally comprising buffering agents and/or isotonic agents.

In a further preferred embodiment, the composition for use in the treatment of cancer comprises or consists of nanoparticles consisting of ammonio alkyl methacrylate copolymers (AMCs), i.e., AMCNPs, in combination with LPS, and in combination with an anti-inflammatory agent, preferably an NSAID, as further adjuvant. In a preferred embodiment, the composition consists of a solvent for dispersing the nanoparticles, LPS, an anti-inflammatory agent (such as NSAID) and the nanoparticles, preferably wherein the solvent is a pharmaceutically acceptable aqueous solution, optionally comprising buffering agents and/or isotonic agents.

CpG Containing AMC Nanoparticles

The inventors demonstrated an enhanced immunotherapeutic potential of the TLR4 agonist CpG when associating to the structure of AMC-based nanoparticles with inherent TLR4 stimulatory properties. Formulation of the nanoparticles allows for the administration of CpG and AMC as a single immunotherapeutic entity, while enhancing the immunotherapeutic potentials. Thus, the system with double TLR4 agonists can significantly improve the outcome of cancer active immunotherapy.

Co-Administration of Nanoparticles and Adjuvants

In another preferred embodiment, the composition of the present disclosure is administered in combination with at least one adjuvant. The adjuvant may be administered in admixture with the composition, or in a separate administrative step, either before, concomitantly, or after the administration of the composition of the present disclosure.

Separate administration may be beneficial in cases where the solvent used for administering the at least one adjuvant would have disadvantageous effects on the nanoparticles of the present disclosure, such as dissolving the nanoparticles.

Side Effects

In one embodiment, the administration of the at least one adjuvant reduces or suppresses side effects associated with the administration of the composition of the disclosure, such as necrosis, inflammation or the like.

EXPERIMENTAL SECTION

In the following, the present invention is illustrated in more detail by way of Examples. However, it is understood that the scope of protection is only determined by the attached claims, not being restricted to any of the following Examples. The following Examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

Example 1: LPS-PLGA Nanoparticles of about 150 nm Size with LPS

Materials

Bacterial LPS from *Salmonella enterica abortus equi* was purchased from Sigma-Aldrich (Stammheim, Germany). Poly-lactide-co-glycolide (PLGA) Resomer® RG 502 H was obtained from Evonik Rohm GmbH (Darmstadt, Germany). Thiazolyl blue tetrazolium boromide (MTT) and Nile Red were supplied by Sigma-Aldrich. Ethyl acetate and polyethylene glycol 400 were obtained from Fischer Scientific (Loughborough, United Kingdom) and Caesar & Loretz GmbH (Hilden, Germany). All other chemicals were of analytical grade.

Cell Lines

Murine colon adenocarcinoma C26 and glioma GL261 cell lines were obtained from NCI, (Frederick, Md., USA). Murine macrophage RAW264.7 (ATCC® TIB-71™) and JAWS II (ATCC® CRL-11904™) dendritic cell lines were purchased from American Type Culture Collection (ATCC, Middlesex, United Kingdom). RAW264.7 and C26 cells were grown in RPMI-1640 medium supplemented with 10% FBS, 50 µg/mL streptomycin, 50 U/mL penicillin G, and 2 mM L-glutamine. A medium with similar composition but containing 4 mM L-glutamine was used for the growth of GL261 cells. JAWS II cells were kept in alpha minimum essential medium (α-MEM) with ribonucleosides and deoxyribonucleosides supplemented with 20% FBS, 50 µg/mL streptomycin, 50 U/mL penicillin G, 4 mM L-glutamine, 1 mM sodium pyruvate and 2.5 µg/mL granulocyte macrophage colony stimulating factor (GM-CSF). All the cell lines were cultivated in a 37° C. incubator with 5% $CO_2$ and 95% humidified air.

Splenocytes were isolated from 6-week-old male BALB/c mice and kept in α-MEM with ribonucleosides and deoxyribonucleosides supplemented with 50 µg/mL streptomycin, 50 U/mL penicillin G, 4 mM L-glutamine, 1 mM sodium pyruvate and 2.5 µg/mL GM-CSF for experimentation.

Animals 6-week-old male BALB/c mice were obtained from Janvier Labs (Roubaix, France). The animals were kept at room temperature (25±2° C.) and relative humidity (40-60%) under a 12 h light/dark cycle. Food and water were provided ad libitum. All studies were approved by the Institutional Animal Care and Use Committee of the University of Franche-Comte and were carried out in accordance with the recommendations in the Guide for the Care and Use of Laboratory Animals in France.

Particle Preparation and Characterization

LPS containing PLGA nanoparticles (LPS-NPs) were prepared through oil in water emulsification/solvent evaporation technique. Briefly, 10 mg PLGA dissolved in 1 mL ethyl acetate was poured into 2 mL of 1 mg/mL aqueous LPS solution. The obtained coarse emulsion was then subjected to high sheer using ultrasonic cell disruptor (Bandelin sonopuls, Berlin, Germany) with 50% power for 1 min, followed by the removal of ethyl acetate under reduced pressure. Labeled nanoparticles for confocal studies were either prepared with Nile Red alone by adding 50 µL of 1 mg/mL Nile Red stock solution in ethyl acetate, or both with Nile Red and FITC (fluorescein isothiocyanate) conjugated LPS (Sigma-Aldrich).

LPS-free PLGA nanoparticles were prepared through a modified solvent displacement method. Briefly, 150 mg PLGA dissolved in 3 mL polyethylene glycol 400 was added dropwise to 30 mL of deionized water at 37° C. and under constant stirring at 400 rpm. The diffusion of polyethylene glycol into the water phase resulted in the formation of surfactant free PLGA nanoparticles. The particles were subsequently washed to dispose of excess polyethylene glycol. All prepared particles were subsequently subjected to further characterization procedures.

To determine the particle size and zeta potential, photon correlation spectroscopy and electrophoretic laser doppler anemometry were applied, respectively. Particle size was measured in terms of effective diameter and polydispersity index (PDI) using particle size/zeta analyzer (Brookhaven Instruments, NY, USA) at a fixed angle of 90° at 25° C. For the measurement of zeta potential, nanoparticle suspension was diluted with $10^5$ M sodium chloride solution to adjust the conductivity at 50 µLS/cm. Zeta potential was measured at 25° C., and the error was calculated as the standard deviation (SD) of three independent measurements.

Determination of LPS Incorporation

LPS incorporation within the particle structure was indirectly ascertained through the quantification of the free LPS within the supernatant following the centrifugal isolation of the nanoparticles from the suspension (10000 rpm at 4° C. for 30 min). The measurement of LPS concentration was conducted by means of Pierce LAL chromogenic endotoxin quantification kit (Life Technologies) and according to the manufacturer instructions.

Scanning Electron Microscopy (SEM)

The shape and morphological characteristics of the prepared nanoparticles was studied using SEM. To fulfill this goal, a fine droplet of the diluted nanoparticle suspension was neatly spread over a cover slip, and was left to completely dry in a desiccator. Having coated the dried sample with a fine layer of gold using a gold sputter module, the particles were observed and photographed by SEM (Hitachi S-2460N, Hitachi Ltd. Corporation, Tokyo, Japan).

In Vitro Release of LPS from the Nanoparticles

To investigate the release of the LPS from the particle structure, an in vitro release study was conducted in phosphate buffered saline (PBS; pH=7.4) at 37° C. Briefly, 1 mL of nanoparticle suspension was centrifuged at 10000 rpm at 4° C. for 30 minutes, and the supernatant was removed. The nanoparticle pellet was then resuspended in 10 mL of release medium, kept in a shaking water bath (70 rpm) where samples were drawn at specific intervals. The samples were then centrifuged at 10000 rpm for 30 minutes (at 4° C.), and the concentration of the free LPS was determined in the supernatant using Pierce LAL chromogenic endotoxin quantification kit (Life Technologies).

Toxicity for the Immune Cells $4 \times 10^5$ RAW 264.7 macrophages or JAWS II DCs were separately seeded in 24-well plates and left to adhere. The cells were subsequently incubated overnight with different concentrations of either LPS solution or corresponding amounts of LPS-NP suspension. The resulted supernatant was collected for further investigations. Toxicity of the LPS/LPS-NP for the macrophages/DCs was assessed by means of the MTT assay. The toxicity of LPS-free control particles was assessed analogously by incubating the cells with the corresponding concentrations of the PLGA matrix formulated as nanoparticles.

In Vitro Cytokine Induction

Following the overnight treatment of the immune cells with LPS/LPS-NP (as described above), concentration of different cytokines (TNF-α, IL-12, IL-1β, and IL-6) in the supernatant was measured using enzyme-linked immunosorbent assay (ELISA) (eBioscience and BD Bioscience) according to the manufacturer instructions. Additionally, a control set of experiments with LPS-free PLGA nanoparticles was conducted to determine the share of PLGA matrix in the cytokine induction.

TLR4 Activation Efficiency

To assess the efficiency of TLR4 activation, the cellular concentration of NF-κBp65 was determined in cell lysates 6 h after the activation of RAW 264.7 macrophages with LPS or LPS-NP by ELISA (Life Technologies) and according to the manufacturer instructions. Briefly, $10^7$ cells were seeded in 25 cm² culture flasks and treated with two different concentrations of LPS solution or LPS-NP suspension (10 and 30 μg/mL). After 6 hours of incubation, the supernatant was removed, the cells were washed twice with cold PBS, and $5 \times 10^6$ cells were harvested for cellular extraction. To this end, cells were lysed in cell extraction buffer (Life Technologies) supplemented with 1 mM PMSF (Life Technologies), and protease inhibitor cocktail (Sigma-Aldrich) for 30 min on ice with vortexing at high speed at 10-min intervals. Concentration of NF-κBp65 was thereafter measured within the cellular extract using ELISA. To determine the impact of TLR4 independent NF-κB activation, a control set of experiments was analogously conducted on the macrophages whose TLR4 signaling pathway had been blocked prior to the treatment with LPS/LPS-NP. The blockage of TLR4 signaling was achieved through 6 h pre-incubation with CLI-095 (Invivogen). This enabled the investigation of the impact of impurities (e.g. nucleic acid impurities) as well as the TLR4 independent pro-inflammatory properties of the polymer matrix.

Confocal Laser Scanning Microscopy (CLSM)

The interplay of the immune cells, LPS and nanoparticles was visually examined using CSLM. To this end, $2 \times 10^5$ RAW264.7 cells were seeded in monolayer on coverslips and were incubated overnight for adherence. The cells were then treated overnight with either Nile Red loaded LPS-NPs, or those prepared with FITC conjugated LPS and Nile Red (final LPS concentration 10 μg/mL).

Membrane staining was fulfilled with FITC-labeled Lectin from Teriticum vulgaris (Sigma-Aldrich) for the cells treated with Nile Red-loaded LPS-NP, while no staining was conducted for those treated with FITC labeled, Nile Red loaded LPS-NP. The cells were then fixed with 4% paraformaldehyde, and the nuclei were stained with 300 nM DAPI (Sigma-Aldrich). The samples were mounted on slides and examined using Nikon Eclipse Ti CLSM (Nikon Cooperation Inc, Tokyo, Japan). Colocalization of FITC conjugated LPS and Nile Red loaded nanoparticles was determined in terms of Pearson correlation and Mandel's overlap (for 50 cells) using Nikon NIS Elements Advanced Research software.

Co-Culture Experiments $2 \times 10^5$ C26 cells were cultured together with $5 \times 10^6$ freshly isolated splenocytes, followed by overnight incubation with two different concentrations of LPS/LPS-NP (30 μg/mL and 10 μg/mL). The next day, the immunogenic cell death was evaluated through the quantification of caspase 3 levels within the cell debris using EnzChek® Caspase-3 Assay Kit #2, Z-DEVD-R110 substrate (Life Technologies). Additionally, the induction of apoptosis within the tumor-splenocyte co-culture was further confirmed by flow cytometry. Briefly, the supernatant was removed, the cells were washed twice with PBS, and the tumor cells were isolated from splenocytes by Percoll (GE healthcare) gradient centrifugation according to a protocol described elsewhere (Liu Y, Chen K, Wang C, et al. Isolation of mice tumor-infiltrating leukocytes by percoll gradient centrifugation. *Bio-Protoc.* 2013;3(17): e892-896). Tumor cells were subsequently resuspended in 1 mL of Annexin V binding buffer (BD Bioscience), labeled with FITC-conjugated Annexin V and PI (BD Bioscience) according to the manufacturer instruction, and examined by flow cytometery (FACSCalibur™, BD Bioscience, Germany). The results were analyzed using FlowJo (version v10.1r7), and the quadrants were set based on untreated C26 cells. The induction of early apoptosis was ascertained based on the calculation of the number of Annexin V positive/PI negative cells in three independent experiments.

In Vivo Therapeutic Efficiency

In vivo therapeutic efficiency was assessed in tumor bearing mice. Briefly, $3 \times 10^5$ C26 cells were subcutaneously injected into the lower right flank of 6-week-old male BALB/c mice. Treatment was initialized on the tenth post-injection day. LPS was injected biweekly in two different doses (100 μg/mL and 1000 μg/mL) either as solution or as LPS-NP (freshly prepared) in three corners around the tumor. Tumor volume was measured as an indicator of the therapeutic response (volume=(width)²×length/2). The animals were sacrificed once the tumor surpassed a volume of 1000 mm³. The weight of the animals was also biweekly controlled. Surviving animals were thrice (every 80 days) rechallenged with an injection of C26 cells in their left flank. Tumor growth was periodically monitored, and when necessary, tumor volume was calculated.

To check the possibility of cross-immunity, the experiments were repeated on a new set of animals, where a complete remission of the syngeneic colorectal cancer was observed. On the day 85 after the initial inoculation of the C26 cells, the animals were challenged with the injection of 5×10⁵ GL261 cells in their left flank. Tumor inoculation was analogously conducted in an untreated control group, which had not been involved within the initial challenge. Tumor growth was periodically monitored and tumor volume was calculated. The schematic of the animal trials are shown in FIG. 1.

In order to demonstrate that the higher tolerability of the LPS-NP is in fact due to the incorporation of the LPS molecules within the nanoparticle structure, tumor-bearing animals were injected with the LPS-NP suspension (1000 µg/mL) prepared three days prior to the treatment, where a significant amount of the LPS had been released from the particle surface. The animals were controlled in terms of the occurrence of internal or external necrosis at or around the site of injection. The results were compared to those obtained for the animals treated with LPS solution and fresh nanoparticle suspension (1000 µg/mL).

To compare the impact of the localized and none-localized induction of the immune response, the animals inoculated with C26 cells in their right flank were injected with three concentrations of LPS-NP (10 µg/mL, 100 µg/mL and 1000 µg/mL) in their left flank. The injections were carried out in a biweekly manner, and the animals were sacrificed once the tumor volume exceeded 1000 mm³.

In Vivo Induction of Pro-Inflammatory Cytokines

The induction of pro-inflammatory cytokines was fulfilled based on the measurement of serum cytokine levels following the peritumoral injection of LPS/LPS-NP (100 µg/mL and 1000 µg/mL). Blood samples were collected 2, 6, 24 and 48 h after the injection of the first dose. Serum concentration of the pro-inflammatory cytokines (TNF-α, IL-12, IL-6 and IFN-γ) was measured using ELISA (eBioscience) and according to the manufacturer instructions.

Intratumoral LPS Penetration

For tracking the LPS penetration (both free or nanoparticle bound) into the tumor after injection, FITC labeled LPS was utilized in the preparation of both the solution and NPs, which were injected in three corners around the tumor. Animals were sacrificed either 1 or 24 h after administration and the tumor was taken for microscopic examination directly using inverted Nikon Eclipse Ti CLSM (Nikon Cooperation Inc, Tokyo, Japan). The green fluorescence of FITC was detected following excitation with an argon laser (excitation wavelength at 488 nm), and by subsequent collection of the fluorescence signals using bandpass filters of 525 nm. The samples were examined either for 2D surface view or optically sectioned into the Z axis to get a 3D reconstruction of the tissue section. Laser power (5%), pinhole size (0.1) and scanning speed (one frame per second) were kept constant for all experiments.

Assessment of Intratumoral Macrophage Infiltration

The decoration of the LPS molecules on the nanoparticle structure was to increase their visibility and uptake for phagocytic cells especially macrophages. This was believed to result in an increased infiltration of the macrophages within the tumor due to the peritumoral injection paradigm. To investigate whether this hypothesis was true, tumors were isolated from the control mice as well as those treated with multiple doses of 100 µg/mL LPS or LPS-NP. The tumor was fixed in 4% paraformaldehyde for 24 hours, embedded in paraffin, and vertically cut in 4 µm cross sections, which were subsequently stained with 10 µg/mL FITC labeled anti-mouse CD14 (eBioscience) and 300 nM DAPI (Sigma-Aldrich) in permeablization solution (TBS+0.1% Triton-X+5% normal goat serum+1% bovine serum albumin) over night in a humidified chamber and at 4° C. The cross sections were mounted on slides and examined using inverted Nikon Eclipse Ti CLSM as previously described. The extent of intratumoral macrophage infiltration was semi-quantitatively assessed through the measurement of the average percentage of the stained surface area in 10 different fields obtained from various areas of three tumor cross sections using Image J® software.

Statistical Analysis

Statistical analysis of the in vitro experiments was performed with Graphpad InStat3. The comparison of data points with the control was conducted using One-way Analysis of Variance (ANOVA) followed by Dunnett Multiple Comparison test. Unpaired t test with Welch correction was used to compare the cytokine induction profiles. Significance levels included $P<0.05$ (*), $P<0.01$ (), and $P<0.001$ (*). In vitro dose-response fitting and LC50 calculation was performed using Origin Lab® 8.

Nanoparticle Characterization

The prepared LPS-LP nanoparticles had an effective diameter of 155±20 nm, with an acceptable PDI of 0.123±0.007. The overall zeta potential of the particles was predictably negative (−15.56±1.82), given the negative charge of both the matrix and the LPS molecules. The percent of decorated LPS was equal to 68.5±4.17%.

FIG. 2 shows the time dependent in vitro release of LPS from the nanoparticles. Due to their superficial localization on the particle matrix, LPS molecules were released in a controlled manner within the first 8 h of the experiments.

Toxicity for the Immune Cells

The toxicity of the LPS and LPS-NP was compared through the calculation of LC50 values for RAW 264.7 macrophages and JAWS II DCs (FIG. 3). As observed, compared to LPS solution, LPS-NP exhibits significantly lower toxicity for both cell lines. Blank LPS-free PLGA nanoparticles showed no significant toxicity for either of the cell lines within the used concentration range.

TLR4 Activation Efficiency

Figure 4:
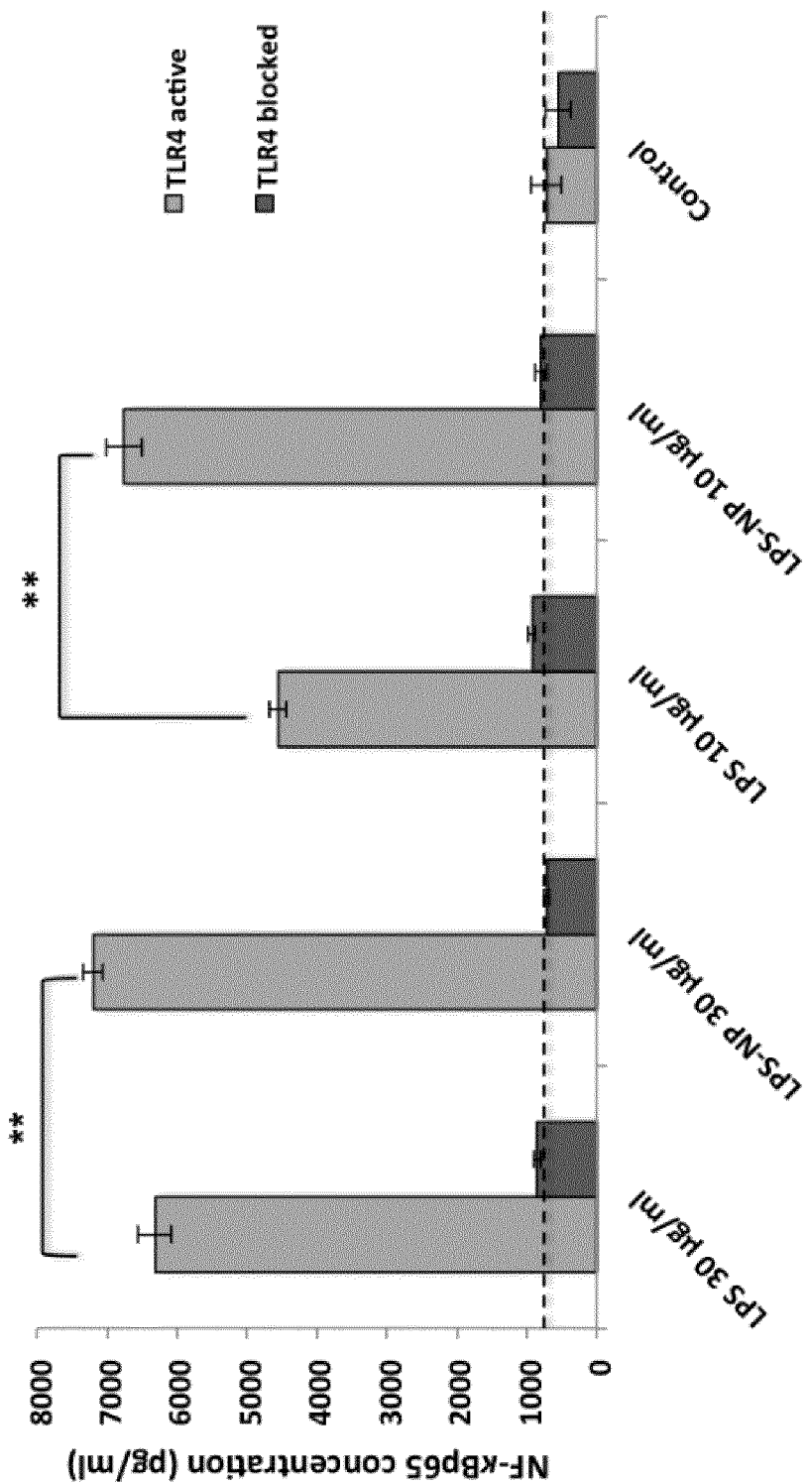
FIG. 4. Induction of NF-κBp65 in $5 \times 10^6$ RAW 264.7 macrophages following 6 h incubation with LPS/LPS-NP. RAW 264.7 cells with TLR4 blocked signaling have been used as control to enable the determination of the TLR4 independent induction of NF-κBp65. Results are presented as the mean±SD of three independent experiments.
Figure 7:
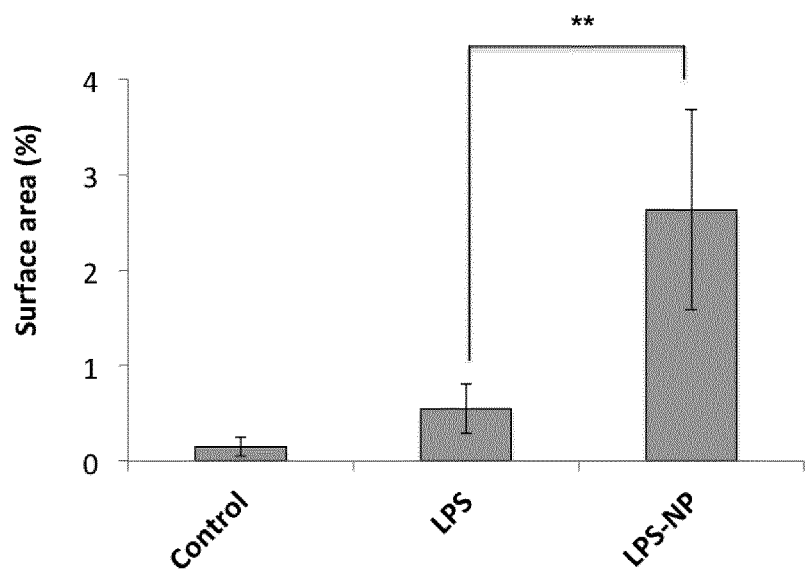
FIG. 7. Analysis of the percentage of the $CD14^+$ stained surface area from 10 independent fields captured from various areas of three tumor cross sections indicated a significantly higher infiltration of the macrophages within the animals treated with LPS-NP compared to the LPS-treated animals and the control group. Scale bars represent 50 μm.

FIG. 4 depicts the cellular concentrations of NF-κBp65 in RAW 264.7 macrophages following 6 h incubation with 10 or 30 µg/mL of either LPS or LPS-NP. TLR4 blocked controls were used to determine the TLR4 independent NF-κB activation (related to the nucleic acid impurities or the particle matrix), which was shown to be relatively negligible. As observed, LPS-NP accounted for higher cellular NF-κB levels at both concentrations, signifying a higher overall TLR4 activation efficiency.

In Vivo Therapeutic Efficiency

Biweekly treatment of the tumor-bearing mice with peritumoral injections of 100 µg/mL LPS, 100 µg/mL LPS-NP and 1000 µg/mL LPS-NP resulted in complete tumor remission after the administration of around four doses (FIG. 2.8-A). Treatment with 1000 µg/mL LPS solution, however, was intolerable for the mice resulting in severe localized necrosis and hampering the continuation of the treatment after the fourth injection. Within the other three groups with full recovery, only one animal per group had recurring tumor. Following tumor remission, surviving animals were rechallanged three times with subcutaneous injections of C26 cells in their left flank (every 80 days). Merely one case of tumor growth was observed within the group treated with 100 µg/mL LPS solution. Additionally, some degrees of cross-immunity were observed, for the growth of GL261 xenograft tumor was significantly retarded in the animals with regressed colorectal tumor compared to the untreated control group. The longest delay was observed in case of the animals treated with 1000 µg/mL LPS-NP (FIG. 2.8-C).

When given on the opposite flank, biweekly treatment with LPS-NP (in particular at 1000 µg/mL) could significantly retard the tumor growth, though the treatment was not as effective as the peritumoral injection of the particles, signifying the essentiality of the localized administration of the immunotherapeutic system (FIG. 2.8-D).

In order to demonstrate that the lower toxicity of LPS-NP indeed pertains to the incorporation of the LPS molecules within the nanoparticle structure (and is not due to the loss of LPS during the preparation process), we explored the impact of nanoparticle age upon the in vivo therapeutic side effects. Given the superficial localization of the LPS, as indicated by the release studies, a considerable number of the LPS molecules tend to release from the nanoparticle surface. Consequently, the majority of the LPS molecules will be released from the nanoparticle surface several days after the preparation. We therefore injected the animals peritumorally with 1000 µg/mL LPS solution, freshly prepared LPS-NP, and the LPS-NP prepared three days prior to the experiments. Interestingly, unlike freshly prepared nanoparticle suspension, both the LPS solution and old nanoparticle suspension resulted in external localized necrosis. Treatment with freshly prepared nanoparticle suspension, however, was very well tolerated.

In Vivo Cytokine Induction

The serum levels of pro-inflammatory cytokines at different time points following the peritumoral injection of the first dose of LPS/LPS-NP are shown in FIG. 2.10. As observed, compared to the untreated cancer control, both LPS and LPS-NP significantly increased the concentration of pro-inflammatory cytokines, with the exception of IL-6 whose secretion (other than a slight increase 2 h after the injection) was significantly suppressed. A higher induction of TNF-α, IL-12 and IFN-γ is observed within the early hours following the treatment with LPS-NP (1000 µg/mL). Within the later hours, however, the LPS-induced serum concentration of these cytokines was significantly more pronounced.

Intratumoral Macrophage Infiltration

As predicted, the results of the immune staining were indeed indicative of a higher tumor infiltration of the macrophages in the animals treated with LPS-NP compared to those treated with LPS solution and of course the control (FIG. 2.12). This is attributable to the higher visibility of the particle-bound LPS to the phagocytic cells in particular macrophages, which enables their higher tumor infiltration due to the peritumoral injection paradigm.

Example 2: Comparison of LPS-PLGA Nanoparticles and LPS Nanoemulsion

Materials

Bacterial LPS from *Salmonella enterica abortus equi* was purchased from Sigma-Aldrich (Stammheim, Germany). Poly-lactide-co-glycolide (PLGA) Resomer® RG 502 H was obtained from Evonik Rohm GmbH (Darmstadt, Germany). Soy lecithin and Miglyol® 812 were supplied by Caesar & Loretz GmbH (Hilden, Germany) and Fagron GmbH (Barbüttel, Germany), respectively. Thiazolyl blue tetrazolium bromide (MTT) and coumarin 6 were purchased from Sigma-Aldrich (Stammheim, Germany). All other chemicals were of analytical grade.

Cell Lines

Murine RAW 264.7 (ATCC® TIB-71™) macrophages and JAWS II (ATCC® CRL-11904™) dendritic cells (DCs) as well as C26 colon adenocarcinoma cell line were obtained from American Type Culture Collection (ATCC, United Kingdom) and National Cancer Institute (NCI, United States), respectively. RAW 264.7 and C26 cells were grown in RPMI-1640 medium supplemented with 10% FBS, 50 µg/mL streptomycin, 50 U/mL penicillin G, and 2 mM L-glutamine. JAWS II cells were cultured in α-MEM with ribonucleosides and deoxyribonucleosides supplemented with 20% FBS, 50 µg/mL streptomycin, 50 U/mL penicillin G, 4 mM L-glutamine, 1 mM sodium pyruvate, and 2.5 µg/mL granulocyte macrophage colony stimulating factor (GM-CSF). All the cell lines were cultivated in a 37° C. incubator with 5% $CO_2$ and 95% humidified air.

Splenocytes were isolated from 6-week-old male BALB/c mice and kept in α-MEM with ribonucleosides and deoxyribonucleosides supplemented with 50 µg/mL streptomycin, 50 U/mL penicillin G, 4 mM L-glutamine, 1 mM sodium pyruvate, and 2.5 µg/mL GM-CSF for experimentation.

Animals 6-week old BALB/c mice were obtained from Charles Rivers Laboratories, Research Models and Services (Sulzfeld, Germany). The animals were kept at room temperature (22±1.5° C.) and relative humidity (50-60%) under a 12 h light/dark cycle. Food and water were provided ad libitum. All animal experiments were carried out in agreement with the European Union and German guidelines, and were approved by the government of North Rhein-Westphalia.

Preparation and Characterization of the LPS-Decorated Nanostructures

Small and large LPS-decorated PLGA nanoparticles (LPS-NP (100 nm) and LPS-NP (700 nm)) were prepared analogously through a simple emulsification/solvent evaporation technique. Briefly, 1 mL of PLGA solution in ethyl acetate was poured in 2 mL of 1 mg/mL aqueous LPS solution. The size of the nanoparticles was adjusted through the optimization of the homogenization step. Small nanoparticles were subjected to ultrasonic cell disruptor (Bandelin sonopuls, Berlin, Germany) with 50% power for 1 minute, whereas large nanoparticles were homogenized by Ultra-Turrax (IKA® Works Inc., Wilmington, N.C., USA) at 10000 rpm. The organic solvent was then removed under reduced pressure.

To examine the impact of matrix, polymeric nanoparticles (LPS-NP) were compared to LPS-decorated nanoemulsion (LPS-NE), which was prepared through high-energy emulsification technique. Briefly, an aqueous solution of LPS and lecithin (both in the concentration of 1 mg/mL) was added stepwise to the lipid phase (Miglyol® 812, final concentration 5 mg/mL). The primary emulsion was attained through subjecting the system to Ultra-Turrax at 22000 rpm for 5 minutes. A second homogenization step using ultrasonic cell disruptor enabled the further reduction of the droplet size (50% power for 35 sec).

Examination of the pro-inflammatory properties of the particle core was achieved through the preparation of the control LPS-free nanostructures. LPS-free nanoemulsion (NE (LPS-free)) was formulated as previously described with the aqueous phase containing lecithin only, and was homogenized primarily using Ultra-Turrax at 26000 rpm for 5 min followed by a further reduction of the droplet size through ultrasonic homogenization (60% power for 1 min). LPS-free PLGA nanoparticles (PLGA (LPS-free)) were prepared through a modified solvent displacement method, where 150 mg PLGA dissolved in 3 mL polyethylene glycol 400 was added dropwise to 30 mL of deionized water at 37° C. and under constant stirring at 400 rpm. Nanoparticles were formed following the diffusion of the polyethylene glycol into the surrounding aqueous medium, which was removed through the addition of a washing step prior to the evaluations. Labeled nanoparticles for uptake and binding studies were prepared in a manner analogous to their unlabeled counterparts, though Coumarin 6 was added to the organic phase during the preparation. All prepared particles were subsequently subjected to further characterization procedures.

The size and surface charge of the nanostructures were determined using photon correlation spectroscopy and electrophoretic laser doppler anemometry, respectively. Size was measured in terms of volumetric mean diameter and polydispersity index (PDI) using particle size/zeta analyzer (Brookhaven Instruments, NY, USA) at a fixed angle of 90° at 25° C. Zeta potential was measured following the dilution of the sample with $10^5$ M sodium chloride solution to adjust the conductivity at 50 μS/cm and at 25° C. All measurements were carried out in triplicates and the results were presented as mean±SD.

Determination of the LPS Incorporation and Release

LPS incorporation and release were determined through a sample and separate method, where the LPS-NP were isolated from the dispersing medium through ultracentrifugation at 10000 rpm for 30 min at 4° C. To separate the free LPS from the nanoemulsion, Nanosep® centrifugal filter units with Omega™ membrane (Pall Corporations) were used. Centrifugation was performed at 10000 rpm for 20 min at 4° C., and the filtrate was collected. Pierce LAL chromogenic endotoxin quantification kit (ThermoFisher Scientific) was used to determine the free LPS concentration within the collected supernatant/filtrate. The free LPS concentration was subsequently used for the calculation of LPS incorporation efficiency.

For the determination of LPS release, 1 mL of nanoparticle suspension/nanoemulsion was added to 9 mL of phosphate buffered saline (PBS, pH 7.4). These were agitated at 300 rpm at 37° C. and samples (100 μL each) were withdrawn at specific intervals and replaced with fresh PBS. Concentration of the free LPS was determined as previously described.

Toxicity for the Immune Cells

RAW 264.7 macrophages or JAWS II DCs were separately seeded in 24-well plates with a density of $4\times10^5$ cells per well. The cells were incubated overnight for adherence and were subsequently incubated with different concentrations of LPS solution, LPS-NP (100 nm), LPS-NP (700 nm), and LPS-NE. Additionally, control sets of experiments were analogously conducted with corresponding concentrations of PLGA (LPS-free) nanoparticles and LPS-free NE. Cell survival was determined afterwards using the MTT assay. The data was then used to calculate the LC50 values.

In Vitro Cytokine Induction

RAW 264.7 and JAWS II cells were seeded in 24-well plates with a density of $4\times10^5$ cells per well. Following adherence, the cells were incubated with either 10 or 30 μg/mL of LPS, LPS-NP (100 nm), LPS-NP (700 nm), and LPS-NE. Control nanostructures were used in corresponding concentrations (50 and 150 μg/mL of PLGA or Miglyol® 812). After overnight incubation, the supernatant was subjected to ELISA to measure the concentration of different pro-inflammatory cytokines (TNF-α, IL-12p40, IL-1β, IL-6; eBioscience, BD Bioscience).

Interaction with the Immune Cells

Nanostructures' interaction with macrophages and DCs was examined to determine the impact of LPS incorporation, size and matrix upon the extent and mechanism of nanostructure uptake and binding. To fulfill this goal, RAW 264.7 and JAWS II cells were seeded in 96-well plates with a density of $10^5$ cells per well. Following adherence, the cells were pre-incubated with the inhibitors of various internalization pathways. These included chlorpromazine hydrochloride—10 μg/mL, nystatin—69 μg/mL, methyl-β-cyclodextrin (MβCD)—10 mmol/L, Cytochalasin D—10 μg/mL, and 5-(N,N-dimethyl) amiloride hydrochloride (DMA)—440 μg/mL (all from Sigma-Aldrich). For the determination of the binding levels, the cells were incubated at 4° C. 30 min prior and for the duration of the experiments. Coumarin 6 loaded nanostructures at a concentration of 10 μg/mL were incubated with the cells for 4 h. Control nanostructures were used in corresponding concentrations (50 μg/mL of PLGA or Miglyol® 812). The cells were thenceforth washed twice with cold PBS and lysed with 100 μL of ethanol. Determination of the uptake and binding levels was achieved based on the flourometric quantification of Coumarin 6 levels.

Apoptosis Induction in Tumor-Splenocyte Co-Culture

A co-culture comprised of $2\times10^5$ C26 cells and $5\times10^6$ freshly extracted splenocytes was incubated overnight with either 30 μg/mL LPS-decorated nanostructures or the corresponding concentration of their control LPS-free counterparts. The supernatant was thereafter removed, the cells were washed twice with PBS, and the immunogenic cell death was investigated through the measurement of cellular caspase 3 levels within the cell debris using EnzChek® Caspase-3 Assay Kit #2, Z-DEVD-R110 substrate (Life Technologies).

In Vivo Antitumor Efficiency

The in vivo antitumor efficiency was determined in a syngeneic colorectal cancer model induced in 6-week-old male BALB/c mice. Briefly, $3\times10^5$ C26 cells suspended in 100 μL PBS were injected in the right flank of the mice. Unlike our previous study where we initiated the treatment quite early (Example 1 above), we set to commence the treatment at later stages of tumor development (initial tumor size of 40-50 mm$^3$) to reduce the chances of early tumor remission. This would help investigate the long-term tolerability and the systemic side effects of the therapies. Animals received biweekly peritumoral injections of LPS solution, LPS-NP (100 nm), LPS-NP (700 nm), and LPS-NE in a concentrations of 1000 μg/mL. Control animals received analogous treatments with PLGA (LPS-free) and NE (LPS-free) in corresponding concentrations (5 mg/mL of PLGA or Miglyol® 812). Nanostructure suspensions/emulsions were prepared fresh prior to each injection. The animals were controlled biweekly in terms of tumor volume (volume=(width)$^2$×length/2), body weight, internal and external necrosis, overall well-being and fatigue. Experiments were terminated on the animals in case the tumor surpassed a volume of 1000 mm$^3$. Other criteria for the termination of the experiments included severe internal or external necrosis, excessive weight loss, extreme fatigue and isolation.

Figure 40A:
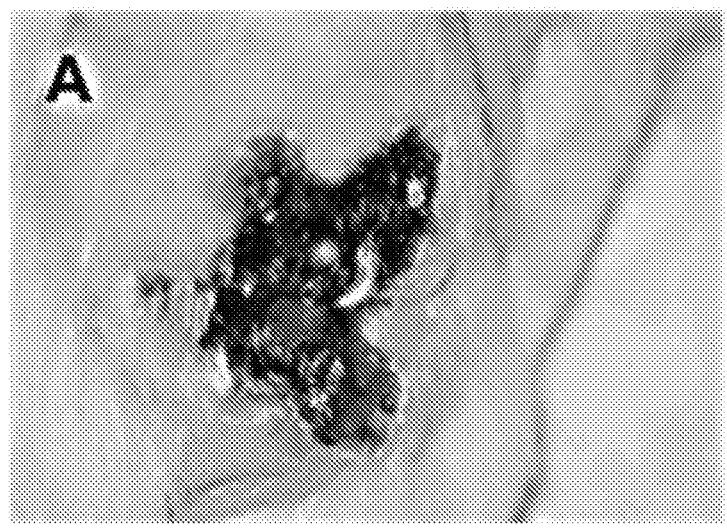
FIG. 40A shows necrosis that was termed as extensive (>6% necrotic surface area
Figure 40B:
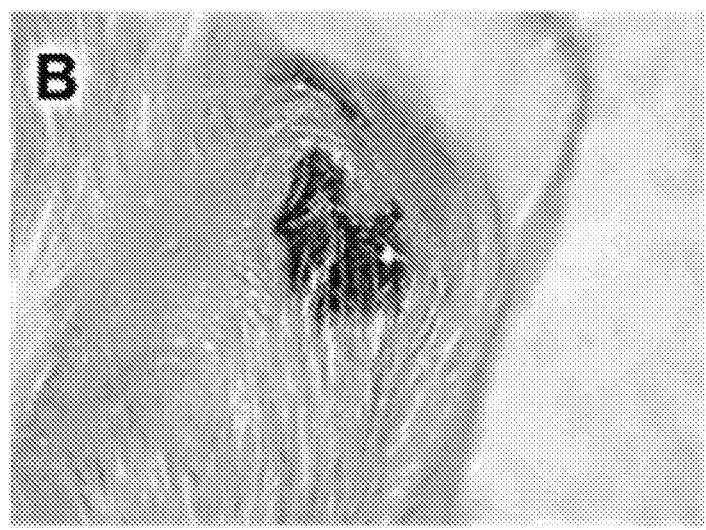
FIG. 40B shows necrosis that was termed as moderate (3-6% necrotic surface area).
Figure 40C:
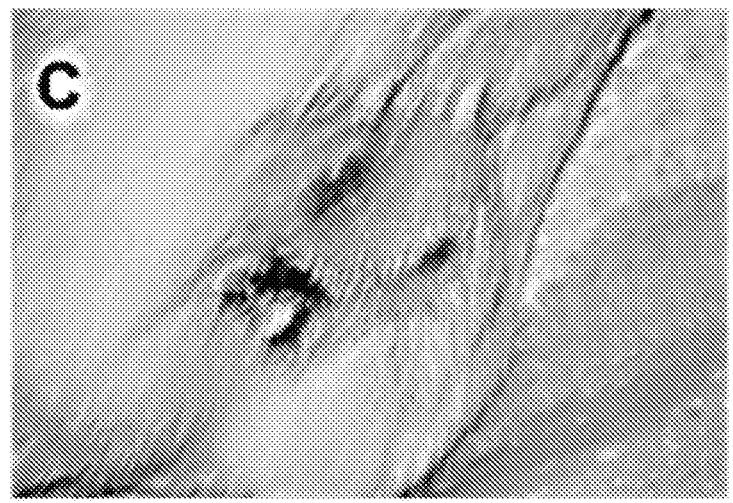
FIG. 40C shows necrosis that was termed as mild (1-3% necrotic surface area).
Figure 40D:
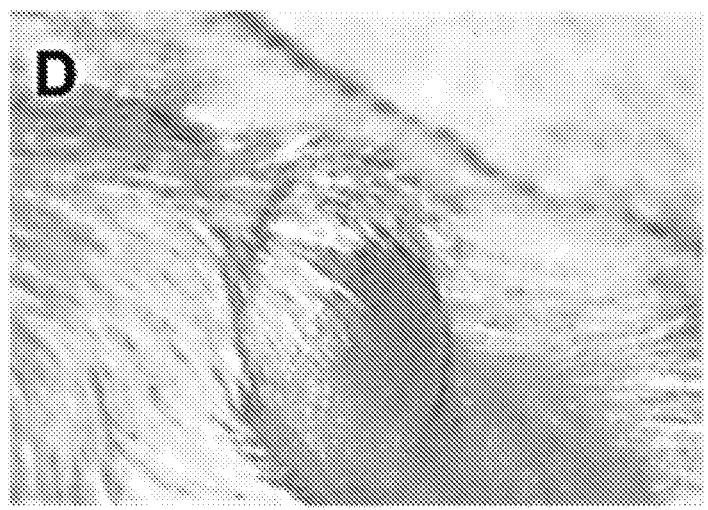
FIG. 40D shows a lack of necrosis.

When observed, the extent of external necrosis was semi-quantitatively assessed through the calculation of the necrotic surface area using Image J® software. The same microscopic settings were used to capture all pictures subjected to analysis. Based on the obtained values, the extent of necrosis was termed as mild (1-3% necrotic surface area), moderate (3-6% necrotic surface area), and extensive 6% necrotic surface area) (Table 2 and FIGS. 40A, 40B. 40C, and 40D).

Statistical Analysis

Statistical analysis of the in vitro experiments was conducted with Graphpad InStat3. One-way Analysis of Variance (ANOVA) followed by Dunnett Multiple Comparison Test was used to compare the data points with the control. Significance levels included $P<0.05$ (*), $P<0.01$ (), and $P<0.001$ (*). In vitro dose-response fitting and LC50 calculation as well as in vivo survival analysis was performed using Origin Lab® 8. Log-rank test was used to explore the significance of inter-group survival differences based on the obtained Kaplan-Meier curves.

Physicochemical Characteristics of the Structures

The physicochemical properties of the nanostructures including size, PDI, and zeta potential as well as the LPS incorporation are shown in Table 1. As observed, both LPS-NP (100 nm) and LPS-NE had a volumetric mean diameter of around 100 nm and negative zeta potential values attributable to both the negative charge of the matrix and the decorated LPS molecules. Due to the higher negative charge of the lipid matrix and the negative load of LPS, the zeta potential value of LPS-NE was more negative than that of LPS-NP (100 nm). The surface charge of large nanoparticles (LPS-NP (700 nm)) was similarly negative, although given the higher amount of the polymer and LPS molecules per particle, larger nanoparticles were associated with slightly higher absolute zeta potential values compared to their small counterparts. Both small and large LPS-NP possessed smooth surface and spherical morphology.

Control nanostructures were prepared LPS-free in a size of about 100 nm and with negative zeta potentials, though smaller in absolute values due to the absence of the negatively charged LPS molecules on their surface. For LPS-decorated nanostructures, LPS was shown to have higher levels of incorporation in the structure of small nanostructures with size reversely impacting the incorporation efficiency.

than LPS-NP (100 nm). The toxicity of LPS-NP for the DCs, however, seems not to be size dependent. Moreover, LPS-NE exhibits significantly lower toxicity for the DCs. On the other hand, investigation of the toxicity of control LPS-free nanostructures indicated the PLGA matrix to be associated with low levels of toxicity. The LPS-free NE, however, exhibits high levels of toxicity, which in case of the DCs, is not significantly different from that of its LPS-decorated counterpart (FIG. 9-E).

Interaction with the Immune Cells

Similar to the toxicity profile, nanostructures' interaction with macrophages and DCs was proven to follow different patterns. In fact, different levels of uptake and binding were observed for each type of particle while interacting with the two cell lines. The relative values for nanostructures surface binding and association is shown in FIG. 10-A. As observed, with the exception of LPS-NP (100 nm), nanostructures exhibit lower levels of internalization by DCs. LPS-NP (700 nm) is associated with the highest binding levels, though it might be the byproduct of the sedimentation of larger particles on the surface of the cells. Also, when compared to LPS-NP (100 nm), LPS-NE shows lower internalization by DCs.

To further investigate the interaction of the nanoparticles with the immune cells and to check whether LPS decoration can influence these interactions, we set to explore the internalization mechanism of the LPS-free and LPS-decorated nanostructure by macrophages (FIG. 10-B). The

TABLE 1

Physicochemical properties of the prepared nanostructures

| Nanostructure | Abbreviation | Mean diameter (nm) | PDI | Zeta potential (mV) | LPS loading (incorporation) (%) |
| --- | --- | --- | --- | --- | --- |
| LPS-decorated PLGA nanoparticles - small | LPS-NP (100 nm) | 103 ± 7 | 0.119 ± 0.004 | −15.4 ± 1.76 | 71.2 ± 3.98 |
| LPS-decorated PLGA nanoparticles - large | LPS-NP (700 nm) | 747 ± 12 | 0.232 ± 0.008 | −22.1 ± 2.25 | 56.4 ± 2.12 |
| LPS-decorated nanoemulsion | LPS-NE | 111 ± 7 | 0.172 ± 0.009 | −46.1 ± 3.42 | 69.6 ± 2.89 |
| Control PLGA Nanoparticles | PLGA (LPS-free) | 105 ± 10 | 0.125 ± 0.035 | −7.42 ± 0.02 | — |
| Control nanoemulsion | NE (LPS-free) | 146 ± 25 | 0.133 ± 0.021 | −38.11 ± 1.78 | — |

LPS Release from the Nanostructures

Figure 8:
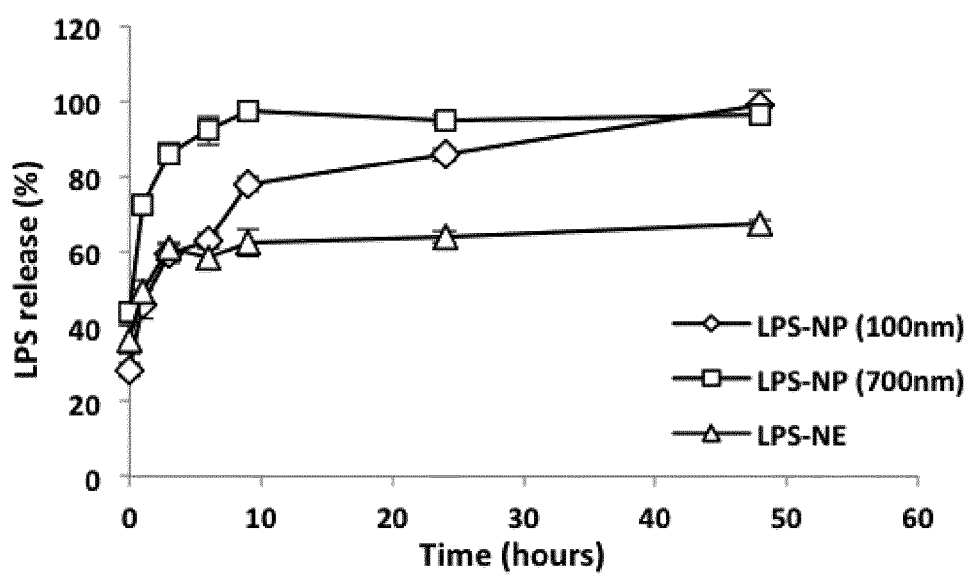
FIG. 8. In vitro LPS release from the nanostructures

The release profile of the LPS from the nanostructures is shown in FIG. 8. As clearly observed, LPS is released in a controlled manner from the surface of the nanostructures, with the extent of the release being dependent upon both the size and matrix. The extent and rate of the controlled LPS release is higher from the larger nanoparticles compared to the small LPS-NP. LPS-NE is associated with the lowest rate and extent of LPS release, which can be attributed to the higher affinity of the lipid A moiety to the triglyceride core of these nanostructures.

Toxicity for the Immune Cells

The dose-response curves of LPS-decorated nanostructures for macrophages and DCs along with the calculated LC50 values are illustrated in FIG. 9. As observed, nanostructures show different toxicity trends for macrophages and DCs, which might be due to their different interaction with these cell lines. In case of macrophages, LPS-NP (100 nm) is associated with the lowest toxicity, with the increase of size negatively influencing the tolerability of the nanoparticles. Additionally, LPS-NE exhibits higher toxicity results demonstrated that pre-incubation with DMA and Nystatin could significantly block the internalization of all LPS-decorated nanostructures, signifying the involvement of macropinocytosis and caveolin-mediated endocytosis. The uptake of LPS-free nanostructures, however, was not as significantly blocked. The internalization of LPS-NP in both sizes as well as the LPS-free PLGA control particles was also reduced following incubation with MβCD, whereas the uptake of the lipid based nanostructures was not significantly affected. Furthermore, unlike LPS-NE whose uptake was proven independent from the clathrin-mediated endocytosis pathway, the internalization of LPS-free NE underwent a significant decrease following pre-incubation with chlorpromazine hydrochloride.

Co-Culture Studies

FIG. 11 depicts the caspase 3 levels measured within the cell debris following the overnight incubation of C26-splenocyte co-culture with 30 μg/mL LPS/LPS-decorated nanostructures, or the corresponding amounts of LPS-free control nanostructures. As observed, treatment with LPS-decorated nanosystems resulted in a significant induction of apoptosis within the tumor cells, both compared to the untreated control and the cells treated with control LPS-free nanostructures.

In Vivo Antitumor Efficiency

Treatment of the animals with 1000 μg/mL of LPS solution resulted in localized necrosis after the administration of the first dosage, which did not develop; but alleviated following further injections. Injection with LPS-NP (700 nm) resulted in moderate levels of localized necrosis in two cases, which further developed after the second injection, but alleviated afterwards. A similar observation was made for LPS-NE, though the degree of necrotic reactions was significantly lower than those caused both by the LPS solution and LPS-NP (700 nm). Unlike the abovementioned, treatment with LPS-NP (100 nm) was not associated with localized necrosis. Detailed information about the post-injection localized necrotic reactions is shown in Table 2 and FIGS. 40A, 40B, 40C, and 40D. In Table 2 and FIGS. 40A, 40B, 40C, and 40D, Necrosis classification has been performed through the calculation of the necrotic surface area using Image J®. The classification system includes extensive necrosis (A: >6% necrotic surface area), moderate necrosis (B: 3-6% necrotic surface area), mild necrosis (C: 1-3% necrotic surface area) and no necrosis (D: <1% necrotic surface area). The same microscopic setting was used to capture all analyzed images. Examples are presented to help visualize the applied classification system (A-D).

The tumor growth profile for individual animals in control and nanostructure-treated groups is shown in FIG. 13.

TABLE 2

Extent of necrosis following the first and second injection.

| | | Animal ID | | | | |
|---|---|---|---|---|---|---|
| | | 1 | 2 | 3 | 4 | 5 |
| Following the first injection | LPS | Extensive | Moderate | Moderate | None | Dead |
| | LPS-NP (100 nm) | None | None | None | None | None |
| | LPS-NP (700 nm) | Moderate | Moderate | None | None | None |
| | LPS-NE | Mild | Mild | None | None | None |
| Following the first injection | LPS | Moderate | Moderate | Mild | None | Dead |
| | LPS-NP (100 nm) | None | None | None | None | None |
| | LPS-NP (700 nm) | Extensive | Moderate | Mild | Mild | None |
| | LPS-NE | Moderate | Mild | None | None | None |

TABLE 3

Reasons for the termination of the trials on individual animals in each group.

| Treatment group | Animal ID | | | | |
|---|---|---|---|---|---|
| | 1 | 2 | 3 | 4 | 5 |
| LPS | Systemic toxicity | Systemic toxicity | Systemic toxicity | Late necrosis | Systemic toxicity |
| LPS-NP (100 nm) | Systemic toxicity | Remission | Systemic toxicity | Late necrosis | Remission |
| LPS-NP (700 nm) | Systemic toxicity | Systemic toxicity | Systemic toxicity | Systemic toxicity | Systemic toxicity |
| LPS-NE | Remission | Tumor size | Tumor size | Systemic toxicity | Tumor size |

In addition to the localized necrosis, animals were monitored for symptoms of systemic toxicity such as anorexia, fatigue, weight loss and isolation. In most of the cases, the systemic adverse effects commenced to appear from the third post-treatment week, shortening the survival of the animals in various cases. LPS-NE was associated with the safest systemic profile, with symptoms of systemic toxicity appearing in case of one animal only. In fact, the survival of the animals was most extended in case of treatment with LPS-NE. Treatment with both sizes of LPS-NP was associated with significantly lower systemic tolerability, very similar to that of LPS solution. Nonetheless, unlike LPS, LPS-NP (100 nm) resulted in two cases of complete remission (FIG. 12). A detailed overview of the reasons for the termination of the trials on individual animals in each group is tabulated in Table 3. The experiments on the animals treated with PBS, PLGA (LPS-free) and NE (LPS-free) were terminated due to the tumor volume surpassing 1000 mm$^3$.

The control experiments conducted with LPS-free nanostructures revealed them to be well tolerated with no localized side effects. Additionally, some degrees of tumor growth retardation were observed in both cases (FIG. 12).

Example 3: AMC Nanoparticles

Materials

Type A and B AMCs, commercially known as Eudragit® RL PO and RS PO, were supplied by Evonik Röhm GmbH (Darmstadt, Germany). Ethyl acetate and acetone were obtained from Fisher Scientific (Loughborough, United Kingdom) and VWR International (Darmstadt, Germany), respectively. Thiazolyl blue tetrazolium bromide (MTT) and Coumarin 6 were purchased from Sigma-Aldrich (Steinheim, Germany). All other reagents were of analytical grade.

Cell Lines

Both murine RAW 264.7 (ATCC® TIB-71™) macrophage and JAWS II (ATCC® CRL-11904™) dendritic cell lines were obtained from American Type Culture Collection (ATCC, United Kingdom). Murine colon adenocarcinoma C26 and glioma GL261 cell lines were purchased from National Cancer Institute (NCI, United States). RAW Blue cells were supplied by Invivogen (France). RAW 264.7 and C26 cells were grown in RPMI-1640 medium supplemented with 10% FBS, 50 μg/mL streptomycin, 50 U/mL penicillin G and 2 mM L-glutamine, while the GL261 cells were kept in a medium with the same composition but containing 4 mM L-glutamine. To ensure the growth of JAWS II cells, α-MEM with ribonucleosides and deoxyribonucleosides supplemented with 20% FBS, 50 μg/mL streptomycin, 50 U/mL penicillin G, 4 mM L-glutamine, 1 mM sodium pyruvate and 2.5 μg/mL granulocyte macrophage colony stimulating factor (GM-CSF) was used. RAW Blue cells were cultured in DMEM supplemented with 10% FBS, 2 mM L-glutamine, 50 μg/mL streptomycin, 50 U/mL penicillin G, 100 μg/mL Normocin and 50 μg/mL Zeocin. All the cell lines were cultivated in a 37° C. incubator with 5% $CO_2$ and 95% humidified air.

Splenocytes were extracted from 6 week old male BALB/c mice and kept in α-MEM with ribonucleosides and deoxyribonucleosides supplemented with 50 μg/mL streptomycin, 50 U/mL penicillin G, 4 mM L-glutamine, 1 mM sodium pyruvate and 2.5 μg/mL GM-CSF for experimentation.

Animals 6-week-old BALB/c mice were obtained from Charles Rivers Laboratories, Research Models and Services (Sulzfeld, Germany). The animals were kept at room temperature (22±1.5° C.) and relative humidity (50-60%) under a 12 h light/dark cycle. Food and water were provided ad libitum. All animal experiments were carried out in agreement with the European Union and German guidelines, and were approved by the government of North Rhein-Westphalia (Az. 84-02.04.2014.A464).

Particle Preparation

Both RSNP and RLNP were prepared surfactant-free through instantaneous emulsification/solvent diffusion method. The particles prepared from each polymer were formulated in two different sizes (about 100 and 700 nm) to investigate the impact of particle size. For all formulations, 200 mg Eudragit® RL or RS powder was dissolved in a mixture of ethyl acetate and acetone (Table 4). The organic phase was then subjected to high sheer (either ultra-turrax (IKA® Works Inc., Wilmington, N.C., USA) at 22000 rpm or ultrasonic cell disruptor (Bandelin sonopuls, Berlin, Germany) with 50% power), while the aqueous phase (water) was added within a one-minute time span using a needled syringe. The organic solvents were subsequently evaporated under reduced pressure. Labeled particles were prepared analogously, though 100 μL of 1 mg/mL Coumarin 6 stock solution in ethyl acetate was added to the organic phase.

Particle Characterization

Particle size and zeta potential were determined using particle size/zeta analyzer (Brookhaven Instruments, NY, USA). Particle size was measured in terms of volumetric mean diameter and polydispersity index (PDI) at a fixed angle of 90° at 25° C. Zeta potential was determined following the dilution of the nanoparticle suspension with sodium chloride solution to adjust the conductivity at 50 μS/cm at the same temperature. Experiments were conducted in triplicates and the results were presented as mean±SD.

Nanoparticle Interaction with the Immune Cells

The particles were investigated in terms of their interaction with the immune cells. Briefly, macrophages and DCs were seeded separately in 96-well plates with a density of $10^5$ cells per well and were incubated with the inhibitors of various uptake pathways 30 minutes prior to and for the duration of the experiments. These included chlorpromazine hydrochloride—10 μg/mL, nystatin—69 μg/mL, methyl-β-cyclodextrin (MβCD)—10 mmol/L, Cytochalasin D—10 μg/mL, and 5-(N,N-dimethyl) amiloride hydrochloride (DMA)—440 μg/mL (all from Sigma-Aldrich) in serum-free medium. To investigate the extent of binding, the cells were incubated at 4° C. 30 min prior to and for the duration of the experiments. The cells were subsequently treated with Coumarin 6 loaded nanoparticles at a concentration of 100 μg/mL for 4 hours, washed twice with cold phosphate buffered saline (PBS), lysed with 100 μL of ethanol, and the association was determined through the fluorometric quantification of Coumarin 6 levels.

To investigate the toxicity profile of the nanoparticles for the immune cells, RAW 264.7 macrophages and JAWS II DCs were separately seeded with a density of $4 \times 10^5$ cells per well (in 24-well plates). The cells were left overnight to adhere and were subsequently treated with different concentrations of RSNP and RLNP. Following overnight incubation, the supernatant was collected for further investigations and the toxicity of the particles for macrophages and DCs was assessed by means of the MTT assay.

Concentration of pro-inflammatory cytokines (TNF-α, IL-12$_{p40}$, IL-1β, IL-6 and IFN-γ) was determined in the supernatant of RAW 264.7 and JAWS II DCs collected within the previous step using enzyme-linked immunosorbent assay (ELISA, eBioscience, BD Bioscience) and according to the manufacturer instructions. To better understand the mechanism of cytokine induction, we checked whether the inhibition of endocytosis and active uptake could impact the TNF-α induction. For this purpose, in an analogous set of experiments, $4 \times 10^5$ RAW 267.4 were incubated for 30 min and for the duration of the experiments either at 4° C. or with MβCD (10 mmol/L), and treated with AMCNPs for 4 h. The induction of TNF-α with or without endocytosis/active uptake inhibition was investigated using ELISA (eBioscience).

NF-κB Induction and TLR4 Involvement

To explore whether the observed cytokine induction is NF-κB dependent, RAW Blue cells, a cell line derived from RAW 264.7 expressing a secreted embryonic alkaline phosphatase (SEAP) gene inducible by NF-κB and AP-1 transcription factors, were seeded in 96-well plates with a density of $10^5$ cells per well and left for adherence. The cells were then incubated overnight with RLNP or RSNP in both sizes (100 μg/ml), and the NF-κB induction was subsequently determined through the quantification of SEAP levels using Quanti Blue assay (Invivogen) and according to the manufacturer instructions. To investigate whether the pro-inflammatory properties of the nanoparticles are TLR4-mediated, an analogous set of experiments was conducted in which the cells were pre-incubated with 3 μg/mL CLI-095 (Invivogen), a selective TLR4 inhibitor, for 6 h prior to exposure to AMCNPs. In addition, a control set of experiments was conducted in which the cells were incubated both with AMCNPs and with 10 μg/mL Polymyxin B (PMB, Invivogen) to neutralize the possible endotoxin contamination. The results were expressed as fold compared to control by dividing the obtained optical density (measured at 640 nm) of the treated cells to that obtained for an untreated control.

Co-Culture Experiments $2 \times 10^5$ C26 cells were incubated with $5 \times 10^6$ freshly isolated splenocytes while treated overnight with 30 μg/mL of different AMCNPs. Concentration of pro-inflammatory and immunosuppressive cytokines (TNF-α, IL-12$_{p40}$, IL-1β, IL-6, IL-10 and TGF-β) was measured in the supernatant using ELISA (eBioscience, BD Bioscience) and according to the manufacturer instructions. Additionally, apoptotic tumor cell death was evaluated through the measurement of caspase 3 levels within the cell debris using EnzChek® Caspase-3 Assay Kit #2, Z-DEVD-R110 substrate (Life Technologies).

In Vivo Antitumor Efficiency 6 week-old male BALB/c mice were injected with $3\times10^5$ C26 cells in their right flank. When the tumor reached a size of 40-50 mm$^3$, treatment was initiated as biweekly injections of the nanoparticle suspensions in three corners around the tumor. The peritumoral injection was selected to maximize the summons of the immune cells from the surrounding tissues. The animals were treated with RSNP-100 nm, RSNP-700 nm, RLNP-100 nm, or RLNP-700 nm in two different concentrations (10 and 100 mg/mL). Control animals received injections of phosphate buffer (pH 7.4) in a manner analogous to the experimental groups. Animals were monitored biweekly in terms of tumor size and body weight. Tumor volume was calculated based on the formula (volume=(width)$^2 \times$length/2), and served as a measure to evaluate the therapeutic efficiency of the particles. Animals were sacrificed once the tumor volume exceeded 1000 mm$^3$, and the tumor and spleen were harvested. The isolated tumors were fixed in 4% paraformaldehyde solution for further investigations. Splenocytes were isolated from the spleen of the treated and control mice, and were incubated overnight either with $2\times10^5$ C26 cells to which they had been previously subjected, or with the same number of GL261 cells to which they had had no previous encounter. Apoptosis levels were determined within the cell debris as previously described.

Figure 14:
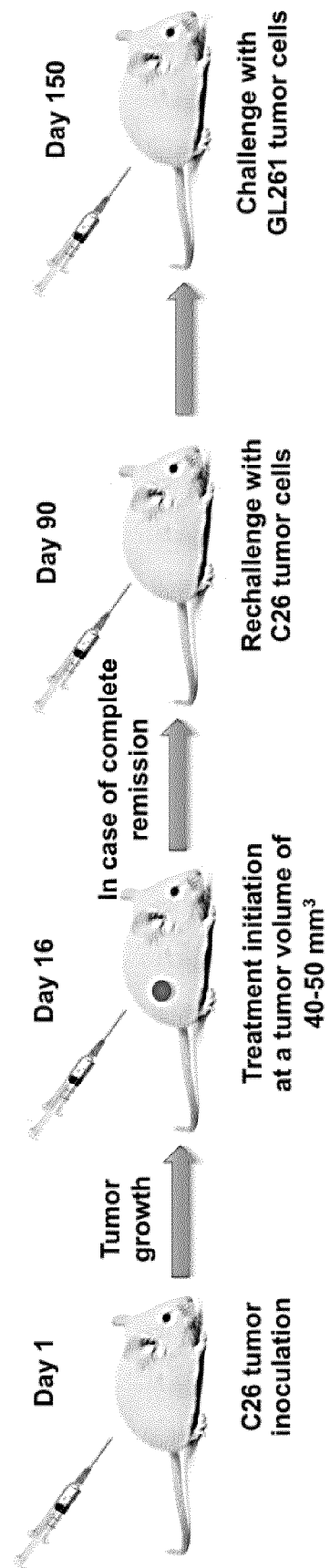
FIG. 14. Schematic of the animal trial setup in Example 3.

Additionally, surviving animals were rechallenged with a second injection of $3\times10^5$ C26 cells three months after the initial tumor inoculation. A further challenge with the injection of $3\times10^5$ GL261 cells succeeded the C26 rechallenge at the beginning of the fifth post-inoculation month to investigate the presence of cross-immunity. A schematic of the animal trial setup is shown in FIG. 14.

Histological and Immunological Evaluation

Tumors isolated from the sacrificed animals and fixed in paraformaldehyde (4%) for 24 h were embedded in paraffin and cut into 5 μm cross sections. The obtained sections were thereafter either subjected to typical hematoxylin and eosin staining or TUNEL (deoxynucleotidyl transferase dUTP nick end labeling) staining (Roche Life Sciences). The latter was utilized to assess apoptosis in the tumor site and was used as instructed by the manufacturer. A negative and a positive control were prepared as instructed to help adjust the optical settings of the microscope and to avoid the detection of the false negative or positive signals. Hematoxylin-eosin and TUNEL stained samples were then examined using normal light microscopy (Leica Leitz DMR, Leica, Germany) and confocal laser scanning microscopy (Nikon Eclips Ti, Nikon Corporation Inc., Japan), respectively. The extent of apoptosis in TUNEL-stained cross sections was determined semi-quantitatively through the measurement of the percentage of stained surface area in 10 random fields captured from various areas of 3 different tumor cross sections using Image J® software.

Statistical Analysis

Statistical analysis of the in vitro experiments was conducted with Graphpad InStat3. One-way Analysis of Variance (ANOVA) followed by Dunnett Multiple Comparison Test was used to compare the data points with the control. Significance levels included P<0.05 (*), P<0.01 (), and P<0.001 (*). In vitro dose-response fitting and LC50 calculation as well as in vivo survival analysis was performed using Origin Lab® 8. Log-rank test was used to explore the significance of inter-group survival differences based on the obtained Kaplan-Meier curves.

Physicochemical Properties of AMCNPs

The particles were prepared in two different sizes, with the small and large particles having a size of around 100 nm and 700 nm, respectively. All particles possessed positive zeta potential values, which were proven to be both polymer and size dependent. Having a higher content of functional quaternary ammonium groups, nanoparticles formulated with type A AMC exhibited a higher density of surface positive charge than those prepared with type B AMC, while the increase of size reversely impacted the zeta potential values, in other words, larger particles were associated with lower zeta potential values than the small ones. Detailed information on the nanoparticle physicochemical properties can be seen in Table 4.

TABLE 4

Formulation parameters and physicochemical properties of the particles

| Particle | Polymer | Final polymer conc. (mg/mL) | Homogenization method, power (%) or speed (rpm) | Volume of aqueous phase (mL) | Ethyl acetate/ acetone ratio | Particle size (nm) ± SD | Polydispersity index (PDI) ± SD | Zeta potential (mV) ± SD |
|---|---|---|---|---|---|---|---|---|
| RLNP-100 nm | Eudr. RL PO | 10 | Ultra-Turrax, 22000 | 20 | 4/3 | 96 ± 17 | 0.171 ± 0.005 | +66 ± 9.1 |
| RSNP-100 nm | Eudr. RS PO | 10 | Ultrasonic cell disrupter, 50% | 20 | 3/1 | 88 ± 14 | 0.153 ± 0.007 | +53 ± 2.4 |
| RLNP-700 nm | Eudr. RL PO | 10 | Ultra-Turrax, 22000 | 10 | 3/1 | 679 ± 37 | 0.248 ± 0.006 | +42 ± 2.3 |
| RSNP-700 nm | Eudr. RS PO | 10 | Ultra-Turrax, 22000 | 20 | 3/1 | 734 ± 43 | 0.298 ± 0.007 | +34 ± 3.2 |

Interaction with Macrophages and DCs

The nanoparticle-induced toxicity pattern differed for the tested cell lines, with size playing a more highlighted role in case of the macrophages, and surface charge exerting higher impact in case of the DCs. However, at a given size, RLNPs were associated with lower LC50 values when compared to RSNPs, signifying the role of cationic charge density upon the toxicity of the nanoparticles for the immune cells (FIG. 15). Investigation of the cytokine induction levels revealed a significant increase of TNF-α, IL-6, IL-1β, IL-12 and IFN-γ. The stimulation of the latter three was limited to the higher and rather toxic concentrations and was most significant in case of RLNP-100 nm. While the increase of particle size led to the augmentation of the TNF-α in both macrophages and DCs, it negatively impacted the induction of IL-12 and IFN-γ in both cell lines. Additionally, inhibition of the major nanoparticle uptake pathways (active uptake and endocytosis) led to a significant decrease of TNF-α induction (FIG. 16).

NF-κB Activation and TLR4 Involvement

As seen in FIG. 17, incubation of RAW Blue macrophages with all AMCNPs resulted in a significant induction of NF-κB compared to the untreated control. The major part of this induction was shown to be independent from endotoxin contamination, for the endotoxin neutralization by Polymyxin B (PMB) only resulted in a slight decrease of NF-κB levels. On the other hand, NF-κB induction was shown to be mainly TLR4 mediated, for a significant (but not complete) reduction of the transcription factor was observed in the cells with inhibited TLR4 signaling.

Antitumor Efficiency in C26-Splenocyte Co-Culture

Incubation of the C26 tumor cells and splenocyte co-culture with 30 μg/mL of all particles resulted in a significant increase of cellular caspase 3 levels within the cell debris compared to the control (FIG. 18-B), signifying remarkable induction of apoptosis within the tumor cells. The increase of cellular caspase 3 was in particular more significant for large nanoparticles. Further, significant increment of pro-inflammatory cytokine concentrations (TNF-α, IL-1β, and IL-12) and the reduction of the immunosuppressive chemokine TGF-β were observed. Additionally, nanoparticles led to a decrease of IL-6 concentration as well as an increase in IL-10 levels (FIG. 18-A). The induction pattern varied for different cytokines, though in general RLNP (both sizes) seemed to be more potent inducers.

Animal Trials

To investigate the antitumor immunotherapeutic efficiency of the nanoparticles, a subcutaneous colorectal tumor was induced in the right flank of the 6-week-old BALB/c mice. As previously discussed, the treatment was initiated when the tumor approached a volume of 40-50 mm$^3$ in the form of biweekly peritumoral injection of the nanoparticle suspension in two concentrations of 10 and 100 mg/mL. The 10 mg/mL nanoparticle suspension was shown to be well tolerated in all animals, with necrotic tumor being observed merely in one case, i.e. one mouse in RLNP-700 nm group (FIG. 19-D). The average tumor volume versus number of injected doses is demonstrated in FIG. 19-B. The tumor volume for individual animals in each group is also depicted (FIG. 19-C-1 to C-5). As observed, the growth of the tumor was significantly retarded in the animals treated with all AMCNPs. Additionally, complete remission was achieved in two animals in RLNP-100 nm group, though one had recurrent tumor in later weeks. Also, one case of significant tumor shrinkage was observed in RSNP-100 nm group, though no complete remission was obtained and the tumor commenced to regrow in the following weeks. No case of complete remission was attained in the mice treated with the 700 nm nanoparticles. Nonetheless, the animals within the RLNP-700 nm group had a remarkably retarded tumor growth until the sixth injection. Henceforth, however, an exponential growth of the tumor was observed. In all, the results were suggestive that all nanoparticles resulted in a significant retardation of the tumor growth, which consequently led to the significant extension of the animals' survival compared to the control group (FIG. 19-A).

RLNP-100 nm was not tolerable for the animals in higher concentration (100 mg/mL), where severe inflammation, and in once case necrosis, was observed around the site of injection following the first dose. Therefore, the experiments were terminated for the animals in this group after the first injection. The other nanoparticles were initially tolerated, leaving no signs of severe inflammation or necrosis. However, the tolerability of the dose seemed to be lower in the long-term run, resulting in side effects such as fatigue, and internal or external necrosis in the tumor site in three cases (FIG. 20-D-1 to D-3), which resulted in the termination of the experiments and the euthanization of these animals. Yet a significant retardation of the tumor growth and the extension of the animals' survival were observed in all groups, with RSNP-700 nm showing the weakest and RLNP-700 nm exhibiting the most potent antitumor efficiency (FIG. 20).

Induction of Immunological Memory

The surviving animal within the RLNP-100 nm group was rechallenged with yet another injection of 3×10$^5$ C26 cells three months after the initial tumor inoculation. No tumor growth was observed following the rechallenge signifying the presence of the immunological memory. The further challenge with GL261 cells resulted in no visible tumor growth within a five-month span following the tumor inoculation. Additionally, the presence of immunological memory as well as the cross immunity was confirmed through the co-incubation of the splenocytes extracted from the treated mice with C26 and GL261 cells. FIG. 21 depicts the significant increase of the caspase 3 levels within the tumor cells incubated with the splenocytes isolated from the mice treated with AMCNPs compared to those incubated with the splenocytes of the PBS-treated controls. Interestingly, and similar to the findings reported above, the immunological memory seemed to have existed not only in case of the C26 cells to which the cells have been previously exposed, but also against the GL261 cells to which the cells had no encounter.

Histological and Immunological Evaluations

Histological evaluation of the tumor microenvironment revealed a significant infiltration of the immune cells in all cases except for the control and RSNP-700 nm (100 mg/mL) groups. In all these groups, the density of the tumor cells was significantly low in many areas of the tumor in particular the margins. Immunogenic cell death was assessed through the investigation of apoptosis induction within the tumor cross sections prepared from the isolated samples from treated and control animals. Despite the difference in the density of the apoptotic cells in various parts of the prepared samples, an overall increase of the apoptotic cells was observed within the tumor samples isolated from the nanoparticle treated animals compared to the control. This was further confirmed by the semi-quantitative determination of the extent of apoptosis induction within the tumor cross sections using Image J® indicating a significant increase of the number of apoptotic cells within the nanoparticle-treated groups compared to the control (FIG. 22).

Example 4: AMC Nanoparticles with LPS

Materials

Bacterial LPS from *Salmonella enterica abortus equi* was purchased from Sigma-Aldrich (Stammheim, Germany). Type A and B ammonio methacrylate copolymers (Eudragit® RL PO and Eudragit® RS PO) were obtained from Evonik Rohm GmbH (Darmstadt, Germany). Ethyl acetate and acetone were obtained from Fisher Scientific (Loughborough, UK) and VWR International (Darmstadt, Germany), respectively. All other reagents were of analytical grade.

Cell Lines

Murine RAW 264.7 (ATCC® TIB-71™) macrophages and JAWS II (ATCC® CRL-11904™) dendritic cells (DCs) were obtained from American Type Culture Collection (ATCC, United Kingdom). C26 colon adenocarcinoma cell line was purchased from National Cancer Institute (NCI, United States). RAW Blue cells were supplied by Invivogen (France). RAW 264.7 and C26 cells were grown in RPMI- 1640 medium supplemented with 10% FBS, 50 µg/mL streptomycin, 50 U/mL penicillin G, and 2 mM L-glutamine. JAWS II cells were cultured in α-MEM with ribonucleosides and deoxyribonucleosides supplemented with 20% FBS, 50 µg/mL streptomycin, 50 U/mL penicillin G, 4 mM L-glutamine, 1 mM sodium pyruvate, and 2.5 µg/mL granulocyte macrophage colony stimulating factor (GM-CSF). RAW Blue cells were kept in DMEM supplemented with 10% FBS, 2 mM L-glutamine, 50 µg/mL streptomycin, 50 U/mL penicillin G, 100 µg/mL Normocin, and 50 µg/mL Zeocin. All the cell lines were cultivated in a 37° C. incubator with 5% $CO_2$ and 95% humidified air.

Splenocytes were isolated from 6-week-old male BALB/c mice and kept in α-MEM with ribonucleosides and deoxyribonucleosides supplemented with 50 µg/mL streptomycin, 50 U/mL penicillin G, 4 mM L-glutamine, 1 mM sodium pyruvate, and 2.5 µg/mL GM-CSF for experimentation.

Animals 6-week-old male BALB/c mice were obtained from Charles Rivers Laboratories, Research Models and Services (Sulzfeld, Germany). The animals were kept at room temperature (22±1.5° C.) and relative humidity of 50-60% under a 12 h light/dark cycle. Food and water were provided ad libitum. All animal experiments were carried out in agreement with the European Union and German guidelines, and were approved by the government of North Rhein-Westphalia.

Particle Preparation and Characterization

RL-LPS and RS-LPS used for the in vitro experiments were prepared with final AMC and LPS concentrations of 5 mg/mL and 1 mg/mL, respectively. To this end, a simple emulsion formation/solvent evaporation technique was used. Briefly, 1 mL of organic phase containing Eudragit® RL PO or Eudragit® RS PO was poured into 2 mL of 1 mg/mL aqueous LPS solution. This coarse emulsion was then homogenized using ultrasonic cell disrupter (Bandelin sonopuls, Berlin, Germany) with 40% (for RL-LPS) or 60% (for RS-LPS) power for 1 min, followed by the removal of ethyl acetate under reduced pressure.

For the conduction of the in vivo experiments, the concentration of AMCs and LPS was adjusted based on the results of the previously conducted animal trials (Chapters two and four) as 10 mg/mL and 100 µg/mL, respectively. Due to the inadequacy of the LPS concentration to stabilize the required mass of AMC using the typical emulsion formation/solvent evaporation technique, an instantaneous emulsification/solvent diffusion method was used. In brief, 200 mg of Eudragit® RL PO or Eudragit® RS PO was dissolved in a mixture of ethyl acetate and acetone (3 mL of ethyl acetate and 1 mL of acetone for Eudragit® RS and 4 mL of ethyl acetate 3 mL of acetone for Eudragit® RL). 20 mL of an aqueous LPS solution (100 µg/mL) was added to the organic phase under homogenization, followed by the removal of the organic phase under reduced pressure. For the purpose of homogenization, Ultra-Thurrax (IKA® Works Inc., Wilmington, N.C., USA; 22000 rpm for RL-LPS) and ultrasonic cell disrupter (50% power for RS-LPS) were used. LPS-free AMCNPs were prepared analogously but using LPS-free aqueous phases.

Both the size and zeta potential of the prepared nanoparticles were determined using particle size/zeta analyzer (Brookhaven Instruments, NY, USA). Particle size was measured in terms of mean diameter and polydispersity index (PDI) at a fixed angle of 90° at 25° C. Zeta potential was determined following the dilution of the nanoparticle suspension with sodium chloride solution to adjust the conductivity at 50 µS/cm at the same temperature. The experiments were conducted in triplicates and the results were reported as mean±standard deviation (SD).

Determination of LPS Incorporation and Release

LPS incorporation was determined indirectly through the quantification of the free LPS concentration within the supernatant of the particles following ultracentrifugation (15000 rpm for 30 min at 4° C.) using Pierce LAL chromogenic endotoxin quantification kit (ThermoFisher Scientific). Similarly, a sample and separate method was used to determine LPS release from the nanoparticles. Briefly, 1 mL of RL-LPS or RS-LPS was added to 9 mL of phosphate buffered saline (PBS, pH 7.4) and kept at 37° C. with constant stirring (300 rpm). Samples (100 µL each) were withdrawn at predetermined intervals and replaced with fresh PBS, while the concentration of the free LPS was determined as previously described.

Cytotoxicity and Cytokine Induction

RAW 264.7 macrophages and JAWS II DCs were seeded with a density of $4 \times 10^5$ cells per well in 24-well plates and left overnight to adhere. The cells were then incubated overnight with different concentrations of LPS, RL-LPS and RS-LPS as well as the equivalent concentrations of RSNP and RLNP as controls. Survival of the immune cells was thereafter determined using the MTT assay. Additionally, concentration of the pro-inflammatory cytokines was measured within the supernatant of the activated cells using enzyme-linked immunosorbent assay (ELISA) and according to the manufacturers' instructions (eBioscience, BD bioscience).

NF-κB Activation

To evaluate the overall immunostimulatory potential of the nanoparticles, cellular levels of NF-κB was determined. To this end, RAW Blue cells were seeded in 96-well plates with a density of $10^5$ cells per well. Following adherence, the cells were incubated with LPS (30 µg/mL), RL-LPS (containing 30 µg/mL and 150 µg/mL of LPS and type A AMC, respectively), RS-LPS (containing 30 µg/mL and 150 µg/mL of LPS and type B AMC, respectively), RLNP (150 µg/mL), and RSNP (150 µg/mL). Furthermore, two control groups treated simultaneously with 30 µg/mL of LPS solution and 150 µg/mL of RLNP or RSNP were included. After 6 h of incubation, NF-κB induction was determined through the quantification of secreted embryonic alkaline phosphatase (SEAP) levels using Quanti Blue assay (Invivogen) and according to the manufacturer instructions. The results were expressed as fold compared to control by dividing the obtained optical density (measured at 640 nm) of the treated cells to those obtained for an untreated control.

Co-Culture Experiments $2 \times 10^5$ C26 cells and $5 \times 10^6$ freshly isolated splenocytes were treated with 30 µg/mL of LPS, RL-LPS, RS-LPS, or the corresponding concentrations of RLNP and RSNP. Following overnight incubation, the induction of apoptosis was assessed through the determination of caspase 3 levels within the cell debris using EnzChek® Caspase-3 Assay Kit #2, Z-DEVD-R110 substrate (Life Technologies). Additionally, concentrations of pro-inflammatory cytokines (TNF-α, IL-12, IL-β, and IL-6) as well as immunosuppressive agents (IL-10 and TGF-β) were measured using ELISA (eBioscience and BD Bioscience).

In Vivo Antitumor Efficiency

The in vivo antitumor efficiency was assessed in 6-week-old male BALB/c mice injected with $3 \times 10^5$ C26 colorectal cancer cells in their right flanks Treatment was initiated once the tumor approached a volume of 40-50 mm³ as the biweekly injection of PBS (control), LPS (100 µg/mL), RL-LPS (prepared with 10 mg/mL type A AMC and 100

µg/mL LPS), RS-LPS (prepared with 10 mg/mL type B AMC and 100 µg/mL LPS), RLNP (10 mg/mL) and RSNP (10 mg/mL) in three to four corners around the tumor. Animals were controlled biweekly in terms of tumor volume (length×(width)/2) as well as the symptoms of systemic toxicity such as severe weight loss, fatigue, anorexia and isolation. Needless to say, trials were terminated in case any of the abovementioned symptoms or severe external or internal localized necrosis were observed, or else once the tumor surpassed a volume of 1000 mm$^3$.

Histological Evaluations

Once the animals were sacrificed, tumors were isolated and fixed in paraformaldehyde (4%) for 24 h, and were subsequently embedded in paraffin and cut into 5 µm cross sections. The obtained sections were thereafter subjected to typical hematoxylin-eosin staining and were examined using normal light microscopy (Leica Leitz DMR, Leica, Germany).

Statistical Analysis

For in vitro experiments, statistical analysis was conducted with Graphpad InStat3. One-way Analysis of Variance (ANOVA) followed by Dunnett Multiple Comparison Test was used to compare the data points with the controls. Significance levels included $P<0.05$ (*), $P<0.01$ (), and $P<0.001$ (*). In vitro dose-response fitting and LC50 calculation as well as the in vivo survival analysis were performed using Origin Lab® 8. Log-rank test was used to explore the significance of inter-group survival differences based on the obtained Kaplan-Meier curves.

Particle Characterization and LPS Release

The size, PDI, zeta potential and LPS loading of the particles are tabulated in Table 5. As observed, all nanoparticles had a size of about 100 nm and positive zeta potential values. For LPS-decorated particles, the percent of LPS incorporation was extremely high for RS-LPS (more than 99% for both in vitro and in vivo formulations) and very high for RL-LPS (about 85% and 95% for in vitro and in vivo particles, respectively). Although LPS was expected to release in a burst manner from the nanoparticles, an increase of LPS concentration within the release medium was not observed. On the contrary, free LPS concentration decreased overtime (FIG. 23-A). Moreover, sedimentation of aggregate-like structures was observed 48 h after the initiation of the release experiments (FIG. 23-B).

than pure LPS solution. In addition to their lower toxicity, both RL-LPS and RS-LPS resulted in higher levels of cytokine induction when compared to pure LPS and AMCNP (FIG. 25).

NF-κB Activation

Investigation of NF-κB in RAW Blue cells demonstrated that incorporation of LPS into the AMC-based polymeric matrix resulted in a significant increase of NF-κB levels compared to LPS solution. This was not the case for the cells simultaneously incubated with LPS solution and AMCNPs, where the NF-κB levels were not significantly increased compared to pure LPS (FIG. 28).

Co-Culture Experiments

Incubation of the C26-splenocyte co-culture with both RL-LPS and RS-LPS led to higher apoptosis induction levels when compared to pure LPS solution and LPS-free AMCNPs (FIG. 27). Though a significant induction of pro-inflammatory cytokines was observed in all LPS and nanoparticle treated groups compared to the control, RS-LPS and RL-LPS seemed to be better inducers of TNF-α, whereas LPS was a more potent activator of IL-12. Compared to the untreated cells, the co-cultures treated with LPS and nanoparticles were associated with lower levels of tumor-induced immunosuppressive agents such as TGF-β. IL-6 induction was most pronounced in case of LPS. As a byproduct of TLR4 activation, however, an increase of IL-10 concentration was observed (FIG. 28).

In Vivo Antitumor Efficiency

The results of the in vivo experiments demonstrated that biweekly peritumoral treatment of the tumor-bearing mice with RL-LPS was associated with a significant improvement of therapeutic efficiency compared to the animals treated with RLNP. This could be inferred from the significantly more pronounced ability of the former to retard the rate of the tumor growth. As observed in FIG. 29, with the exception of the animals with early-stage tumor remission, the size of the tumor in the animals treated with RLNP by the 10$^{th}$ injection had almost reached the termination threshold (1000 mm$^3$). On the contrary, the tumor size of the animals injected with RL-LPS was only around 500 mm$^3$). Nevertheless, due to the LPS-associated systemic side effects, the treatment of the animals in this group was prematurely terminated. As evident from the survival analysis (FIG. 30), however, RL-LPS had improved the long-term tolerability and

TABLE 5

Physicochemical properties of the prepared nanoparticles

| Nanostructure | Abbr. | Mean diameter (nm) | PDI | Zeta potential (mV) | LPS loading (incorporation) (%) |
|---|---|---|---|---|---|
| LPS-decorated Type A AMC nanoparticles | RL-LPS | In vitro: 109 ± 8<br>In vivo: 89 ± 5 | In vitro: 0.123 ± 0.01<br>In vivo: 0.124 ± 0.01 | In vitro: +24.1 ± 3.48<br>In vivo: +44 ± 4.1 | In vitro: 99.7 ± 0.2<br>In vivo: 99.5 ± 0.3 |
| LPS-decorated Type B AMC nanoparticles | RS-LPS | In vitro: 115 ± 10<br>In vivo: 82 ± 6 | In vitro: 0.145 ± 0.007<br>In vivo: 0.112 ± 0.003 | In vitro: +15.5 ± 2.13<br>In vivo: +30 ± 2.6 | In vitro: 85.6 ± 0.7<br>In vivo: 94.6 ± 0.9 |
| Type A AMC nanoparticles | RLNP | 96 ± 17 | 0.171 ± 0.005 | ±66 ± 9.1 | — |
| Type B AMC nanoparticles | RSNP | 88 ± 14 | 0.153 ± 0.007 | ±53 ± 2.4 | — |

Interaction with the Immune Cells

Decoration of LPS on the surface of the AMCNPs resulted in a significant reduction of their toxicity for the immune cells (FIG. 24). This was particularly more pronounced in case of RS-LPS, which was 3-4 times less toxic reduced the LPS-related systemic side effects, which becomes visible by a significant extension of the survival of these animals was observed compared to those treated with pure LPS solution. This is related to the effect that animal studies not only are terminated by tumor death but also by severe necrosis and only suppressing both could significantly extent the animal survival.

RS-LPS seemed to be neither as effective nor as tolerable as RL-LPS, for one case of severe weight loss and two cases of external necrosis occurred within the early stages of the treatment with these particles. Additionally, when compared to the animals treated with RSNP, no significant retardation of the tumor growth was observed in the animals that survived longer.

Histological Evaluations

Microscopic examination of the heamatoxylin-eosin stained tumor cross sections revealed an enhanced infiltration of the immune cells as well as the lower density of the tumor cells in various areas of the tumor in the animals treated with RS-LPS and RL-LPS compared to those having received the LPS-free RLNP and RSNP. This was in particular more pronounced in case of the animals treated with RL-LPS, for similar to the cross sections obtained from the LPS-treated group, areas with extremely low cell densities were observed.

Example 5: Combination of Nanoparticles with Adjuvants

Materials

Type A and B ammonio methacrylate copolymers (AMCs; Eudragit® RL PO and RS PO, respectively) were obtained from Böhringer Ingelheim. CpG ODN 2395 was supplied by Eurofin Genomics. Celecoxib was purchased from Sigma-Aldrich.

Particle Preparation

Type A and B nanoparticles of ammonio methacrylate copolymers (RLNP and RSNP, respectively) with a size of 100 nm were prepared through an instantaneous emulsification solvent diffusion technique. Briefly, the 200 mg of each polymer was dissolved in a mixture of ethyl acetate and acetone with a ratio of 7:3 for Type A and 4:1 for Type B AMC. 20 mL of deionized water was added to this mixture under homogenization (Ultra-Turrax: 22000 rpm for RLNP and ultrasound cell disrupter at 50% power for RSNP) using a needled syringe. The organic solvent was removed under reduced pressure.

CpG ODN 2395 was added to the nanoparticle formulations as a concentrated aqueous solution immediately prior to the experiments.

Animal Trials

A syngeneic tumor model was induced in 6-week-old male BALB/c mice through the subcutaneous injection of $3\times10^5$ C26 colorectal cancer cells in the right flank. Treatment was initiated once the tumor approached a volume of 40-50 mm$^2$, in the form of biweekly peritumoral injections. Control animals received injections of phosphate buffered saline (PBS) in an analogous manner. The animals were monitored in terms of the tumor volume, the body weight and the overall wellbeing. Experiments were terminated once the tumor surpassed a volume of 1000 mm$^3$.

Celecoxib and RLNP Experiments

Figure 31:
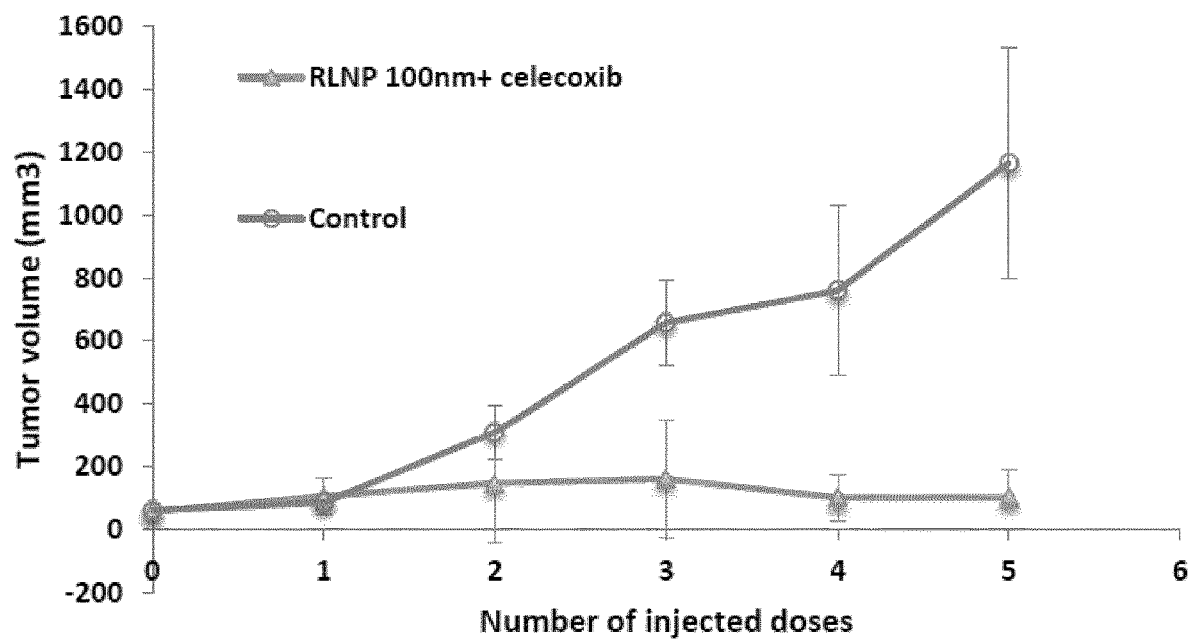
FIG. 31. Comparison of tumor volume for RLNP 100 nm nanoparticles injected with celecoxib in relation to control group.
Figure 32:
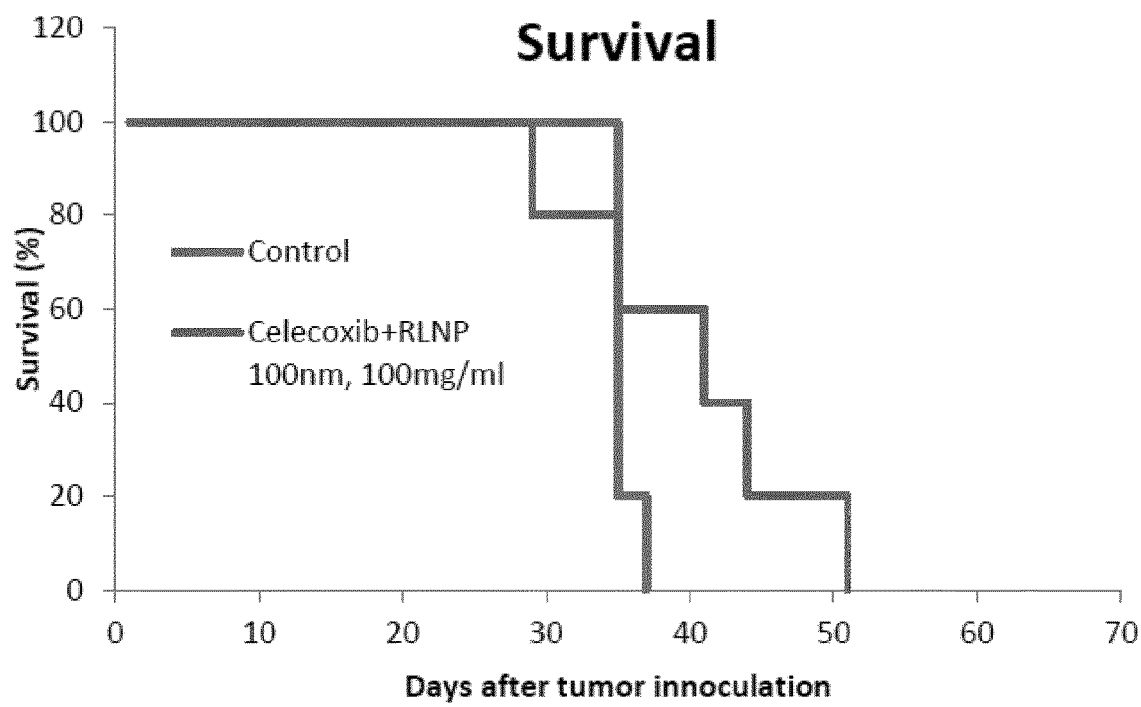
FIG. 32. Survival analysis for RLNP 100 nm nanoparticles injected with celecoxib in relation to control group.
Figure 33:
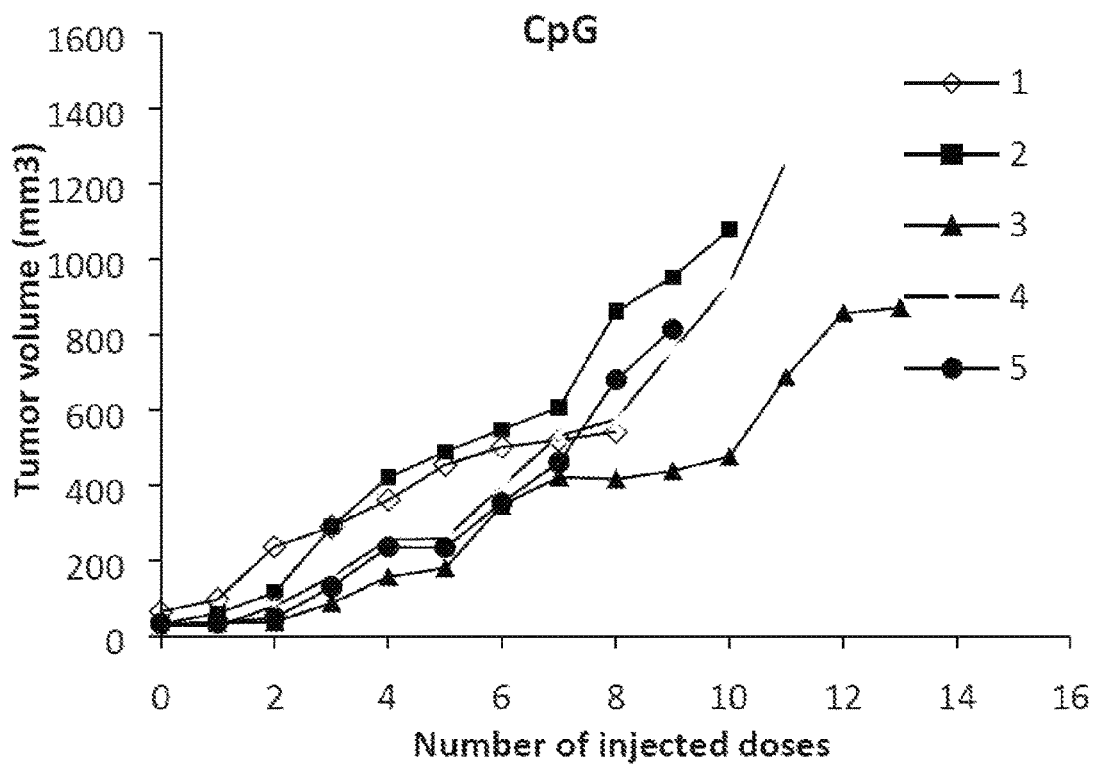
FIG. 33. Tumor volume following the biweekly treatment of C26 tumor-bearing mice with peritumoral injections of CpG.
Figure 34:
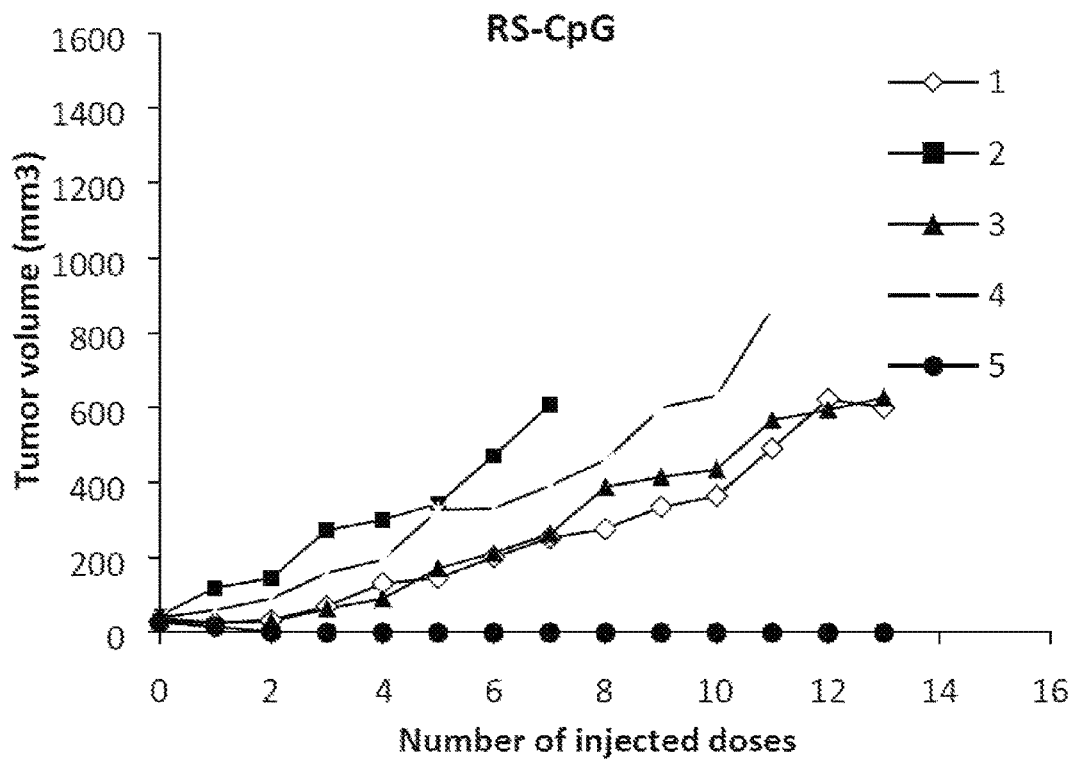
FIG. 34. Tumor volume following the biweekly treatment of C26 tumor-bearing mice with peritumoral injections of CpG associated to type B AMC nanoparticles.
Figure 35:
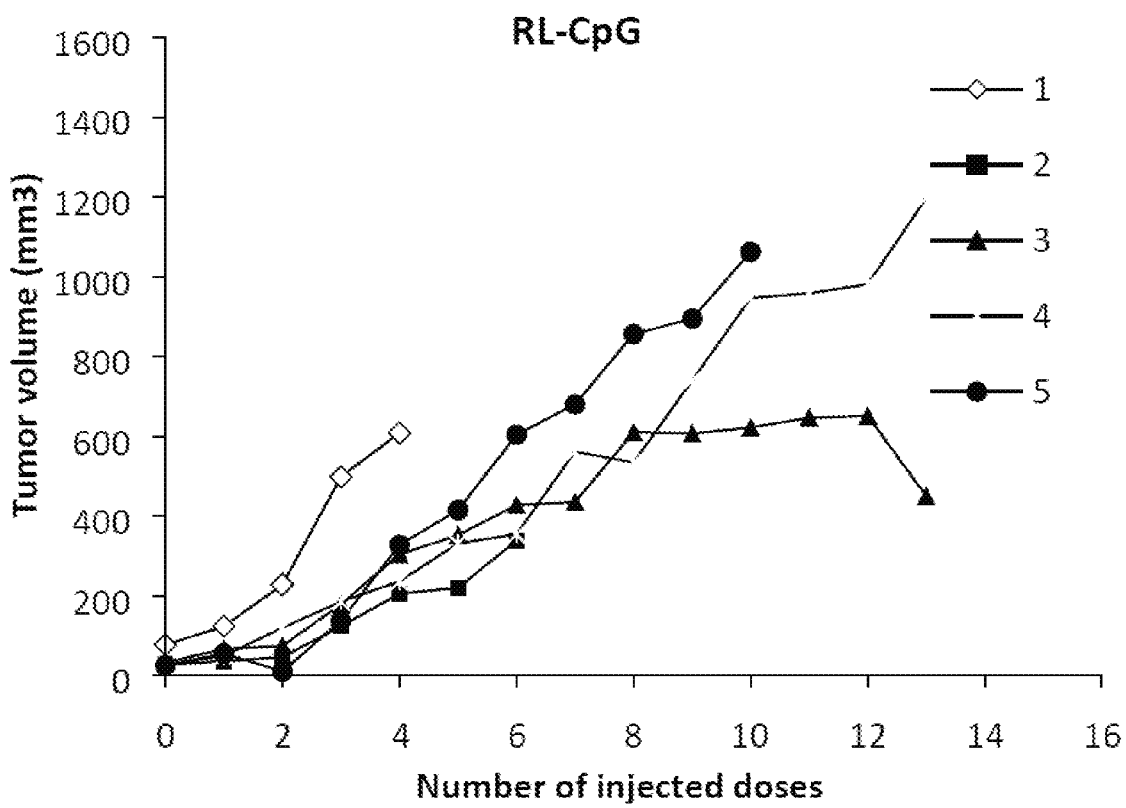
FIG. 35. Tumor volume following the biweekly treatment of C26 tumor-bearing mice with peritumoral injections of CpG associated to type A AMC nanoparticles.
Figure 36:
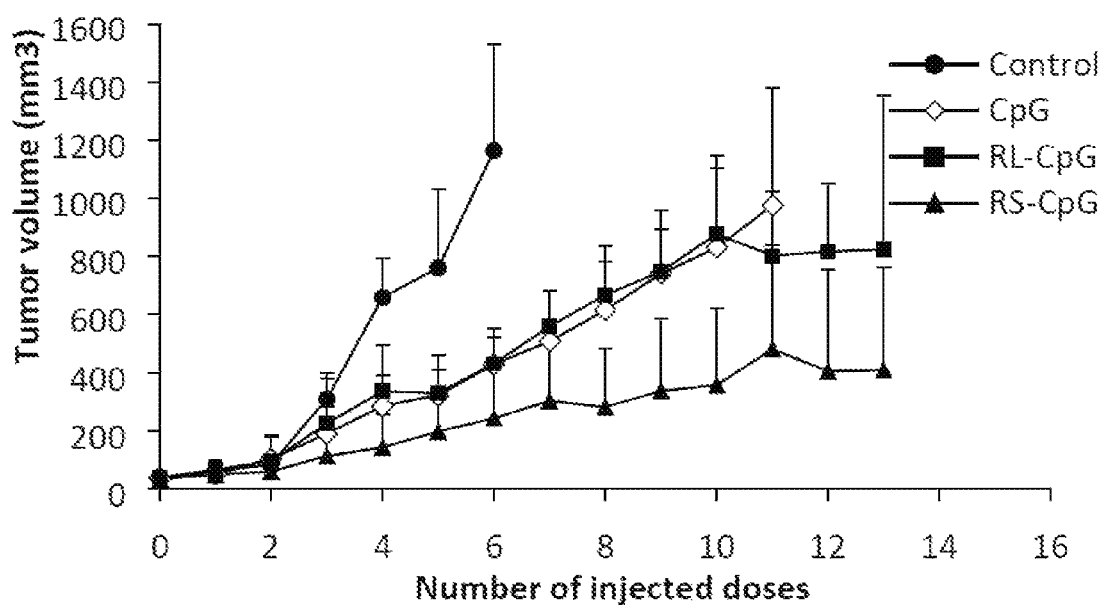
FIG. 36. Tumor volume in C26 tumor-bearing mice (n=5) receiving biweekly injections of PBS (control), CpG, RL-CpG (CpG and type A AMC nanoparticles), RS-CpG (CpG and type B AMC, respectively).
Figure 37:
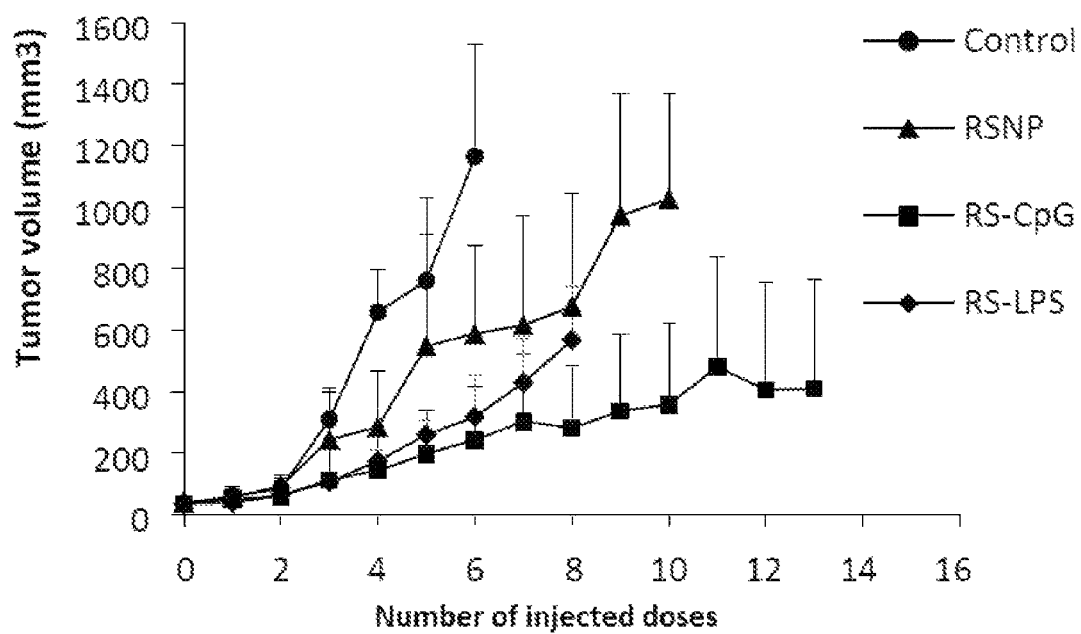
FIG. 37. Tumor volume in C26 tumor-bearing mice (n=5) receiving biweekly injections of PBS (control), RS nanoparticles, RS-LPS (LPS and type B AMC nanoparticles), RS-CpG (CpG and type B AMC, respectively).
Figure 38:
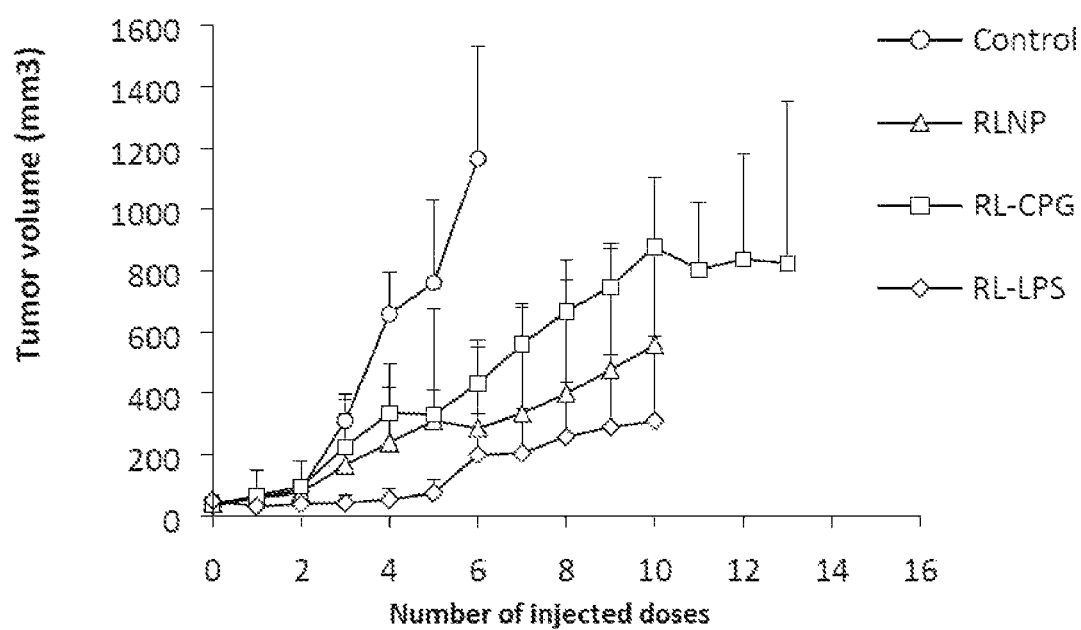
FIG. 38. Tumor volume in C26 tumor-bearing mice (n=5) receiving biweekly injections of PBS (control), RL nanoparticles, RL-LPS (LPS and type A AMC nanoparticles), RL-CpG (CpG and type A AMC, respectively).
Figure 39:
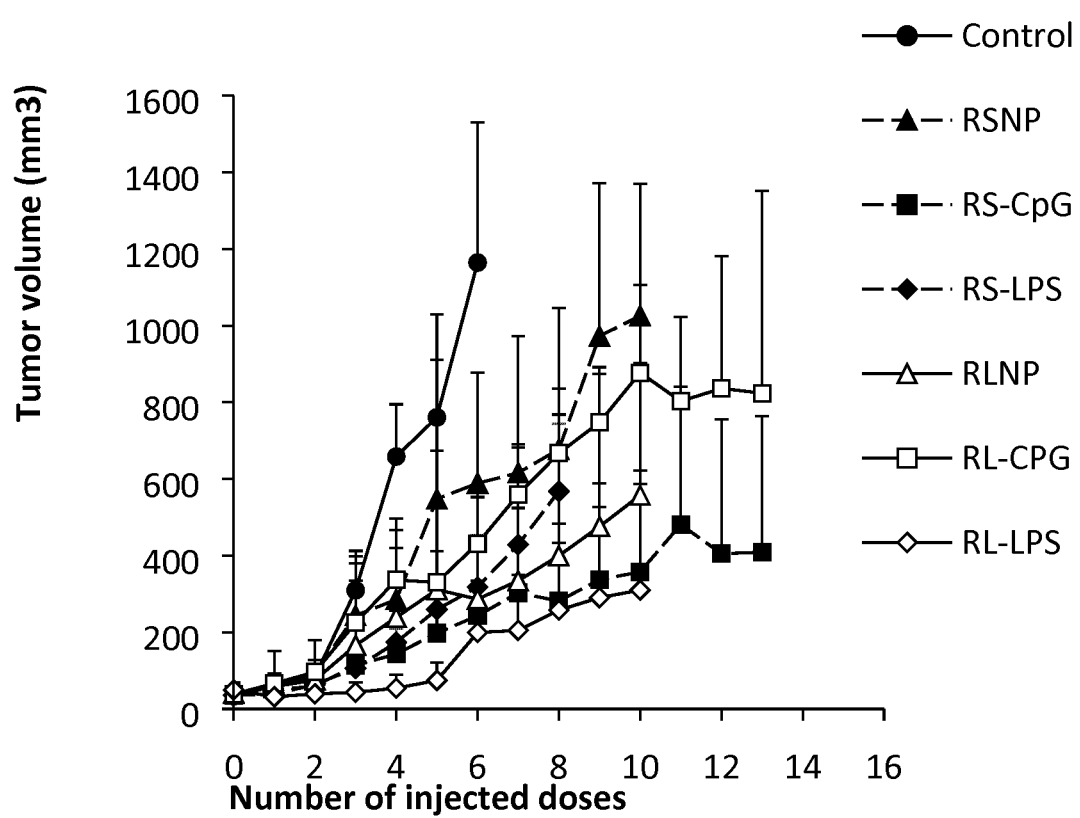
FIG. 39. Tumor volume in C26 tumor-bearing mice (n=5) receiving biweekly injections of PBS (control), RS nanoparticles, RS-LPS (LPS and type B AMC nanoparticles), RS-CpG (CpG and type B AMC, respectively), RL nanoparticles, RL-LPS (LPS and type A AMC nanoparticles), RL-CpG (CpG and type A AMC, respectively).

For these experiments, two groups of tumor-bearing mice were treated with RLNP (100 nm) at a concentration of 100 mg/mL. The animals in one group also received injections of celecoxib as a solution in glycofurol (5 mg/kg body weight). The celecoxib treatment was started one day prior to the first nanoparticle injection and continued on a daily basis with two days of rest over the weekend. Our observations revealed that treatment with RLNP (100 nm) at this concentration resulted in severe inflammation and in one case necrosis at the injection site, which were avoided in case of the treatment with celecoxib. Although the size of the tumor in PBS-treated control group had surpassed the termination threshold (1000 mm$^3$) after the fifth injection, the animals treated with celecoxib and RLNP combination had significantly smaller tumor sizes at this time point (see FIGS. 31 and 32).

RL-CpG and RS-CpG Experiments

As explained above, CpG ODN 2395 (TCGTCGTTTTC-GGCGCGCGCCG) SEQ ID NO: 1 was added to the nanoparticle formulations as a concentrated aqueous solution immediately prior to the experiments. The particle formulations were then peritumorally injected. The concentrations of the injected RLNP or RSNP and CpG ODN 2395 were 10 mg/mL and 300 µg/mL, respectively. The experiments show a much stronger anti-tumor effect by the combination RS-CpG than for each component alone and one animal ended in full remission. For RL-CpG no additional benefit over CpG was observed. The best outcome here was achieved with pure RLNP.

Embodiments

The present disclosure also pertains to the following numbered embodiments.

1. Composition for use as a medicament, the composition comprising nanoparticles, wherein the nanoparticles comprise a polymer selected from the group consisting of PLGA, PLA, PGA, PCL and poly(meth)acrylates, or a lipid.
2. Composition according to embodiment 1, wherein the nanoparticles comprise a polymer selected from the group consisting of PLGAs, amino alkyl methacrylate copolymers, methacrylic acid copolymers, methacrylic ester copolymers, and ammonio alkyl methacrylate copolymers, and preferably wherein the polymer is selected from the group consisting of PLGAs and amino alkyl methacrylate copolymers.
3. Composition for use according to embodiment 2, wherein the polymer of the nanoparticles is an ammonio methacrylate copolymer, preferably selected from Eudragit RS and/or Eudragit RL.
4. Composition for use according to any one of embodiments 1 to 3, wherein the composition further comprises at least an adjuvant selected from the group consisting of an anti-inflammatory agent, an immuno-stimulating agent, a CpG oligodeoxynucleotide, and a lipopolysaccharide (LPS).
5. Composition for use according to any one of embodiments 1 to 4, wherein the composition further comprises at least an adjuvant, and wherein the adjuvant is an anti-inflammatory agent, preferably wherein the anti-inflammatory agent is an NSAID; further preferably wherein the NSAID is a COX-1 and/or COX-2 inhibitor; still further preferably wherein the NSAID is selected from the group consisting of aspirin, choline and magnesium salicylates, choline salicylate, celecoxib, diclofenac potassium, diclofenac sodium, diclofenac sodium with misoprostol, diflunisal, etodolac, fenoprofen calcium, flurbiprofen, ibuprofen, indomethacin, ketoprofen, magnesium salicylate, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib, and combinations thereof; and still further preferably, wherein the NSAID is selected from the group consisting of aspirin, ibuprofen, celecoxib, and combinations thereof.

6. Composition for use according to any one of embodiments 1 to 5, wherein the composition further comprises at least an adjuvant, and wherein the adjuvant is an immuno-stimulating agent, preferably wherein the immuno-stimulating agent is selected from the group consisting of one surface active compound and/or their respective oil-in-water emulsion.

7. Composition for use according to any one of embodiments 1 to 6, wherein the composition further comprises at least an adjuvant, and wherein the adjuvant is a CpG oligodeoxynucleotide, wherein the CpG oligodeoxynucleotide has a sequence which is at least 90% identical to SEQ ID NO: 1, more preferably wherein the CpG oligodeoxynucleotide has a sequence selected from the group SEQ ID NO: 1.

8. Composition for use according to any one of embodiments 1 to 7, wherein the composition further comprises at least an adjuvant, and wherein the adjuvant is a lipopolysaccharide (LPS).

9. Composition for use according to any one of embodiments 1 to 8, wherein the composition is used for the treatment of cancer, preferably wherein the cancer is selected from the group consisting of breast cancer, gastric carcinoma, bladder cancer, colorectal cancer, pancreatic cancer, colon cancer, lung cancer, prostate cancer, gliomas and melanomas, still further preferably wherein the cancer is selected from the group consisting of breast cancer, colon cancer, lung cancer, prostate cancer, gliomas and melanomas, still further preferably wherein the cancer is colon cancer.

10. Nanoparticle comprising a polymer selected from the group consisting of PLGA, PLA, PCL and poly(meth)acrylates, or a lipid.

11. Nanoparticle according to embodiment 10 wherein the polymer is selected from the group consisting of PLGAs, amino alkyl methacrylate copolymers, methacrylic acid copolymers, methacrylic ester copolymers, and ammonio alkyl methacrylate copolymers, and preferably wherein the polymer is selected from the group consisting of PLGAs and amino alkyl methacrylate copolymers.

12. Nanoparticle according to any one of embodiments 10 or 11 wherein the polymer is an ammonio methacrylate copolymer, preferably selected from Eudragit RS and/or Eudragit RL.

13. Nanoparticle according to any one of embodiments 10 to 12 wherein the nanoparticle further comprises at least an adjuvant selected from the group consisting of an anti-inflammatory agent, an immuno-stimulating agent, a CpG oligodeoxynucleotide, and a lipopolysaccharide (LPS).

14. Nanoparticle according to any one of embodiments 10 to 13, wherein the nanoparticle further comprises at least an adjuvant, and wherein the adjuvant comprises a lipopolysaccharide (LPS).

15. Nanoparticle according to any one of embodiments 10 to 13, wherein the nanoparticle further comprises at least an adjuvant, and wherein the adjuvant comprises at least one anti-inflammatory agent.

16. Nanoparticle according to any one of embodiments 10 to 13, wherein the nanoparticle further comprises at least an adjuvant, and wherein the adjuvant comprises a CpG oligodeoxynucleotide.

17. Nanoparticle according to any one of embodiments 10 to 13 and 15, wherein the nanoparticle further comprises at least an adjuvant, and wherein the adjuvant is an anti-inflammatory agent, preferably wherein the anti-inflammatory agent is an NSAID; further preferably wherein the NSAID is a COX-1 and/or COX-2 inhibitor; still further preferably wherein the NSAID is selected from the group consisting of aspirin, choline and magnesium salicylates, choline salicylate, celecoxib, diclofenac potassium, diclofenac sodium, diclofenac sodium with misoprostol, diflunisal, etodolac, fenoprofen calcium, flurbiprofen, ibuprofen, indomethacin, ketoprofen, magnesium salicylate, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib, and combinations thereof; and still further preferably, wherein the NSAID is selected from the group consisting of aspirin, ibuprofen, celecoxib, and combinations thereof.

18. Nanoparticle according to any one of embodiments 10 to 13, 15 and 17, wherein the polymer is an ammonio methacrylate copolymer and the at least one adjuvant is celecoxib.

19. Nanoparticle according to any one of embodiments 10 to 14, wherein the nanoparticle further comprises at least an adjuvant, and wherein the adjuvant is a lipopolysaccharide (LPS).

20. Nanoparticle according to any one of embodiments 10 to 13, and 19, wherein the polymer is an ammonio methacrylate copolymer and the at least one adjuvant is a lipopolysaccharide (LPS).

21. Nanoparticle according to any one of embodiments 10 to 14, wherein the nanoparticle further comprises at least an adjuvant, and wherein the adjuvant is an immuno-stimulating agent, preferably wherein the immuno-stimulating agent is selected from the group consisting of one surface active compound and/or their respective oil-in-water emulsion.

22. Nanoparticle according to any one of embodiments 10 to 14, wherein the nanoparticle further comprises at least an adjuvant, and wherein the adjuvant is a CpG oligodeoxynucleotide, wherein preferably the CpG oligodeoxynucleotide has a sequence which is at least 90% identical to SEQ ID NO. 1, more preferably wherein the CpG oligodeoxynucleotide has a sequence selected from the group SEQ ID NO: 1.

23. Nanoparticle according to any one of embodiments 10 to 21, wherein the adjuvant loading is from about 25 wt.-% to 100 wt-%, from about 50 wt.-% to 100 wt-%, from about 75 wt.-% to 100 wt-% based on the weight of the nanoparticle without adjuvant loading.

24. Nanoparticle according to any one of embodiment 10 to 23, wherein the nanoparticle has a mean diameter from about 50 nm to about 900 nm, from about 50 nm to about 800 nm, from about 75 nm to about 800 nm, or from about 90 nm to about 750 nm.

25. Composition for use according to any one of embodiments 1 to 9, or nanoparticle according to any one of embodiments 10 to 24, wherein the adjuvant is released in-vitro in an amount of about 10% to about 60% after 1 hour, in an amount of about 20% to about 80% after 2 hours, and in an amount of about 30% to about 90% after 4 hours.

26. Composition for use according to any one of embodiments 1 to 9, or nanoparticle according to any one of embodiments 10 to 24, the nanoparticle is PLGA and the adjuvant is LPS, wherein the adjuvant is released in-vitro in an amount of about 10% to about 60% after 1 hour, in an amount of about 20% to about 80% after 2 hours, and in an amount of about 30% to about 90% after 4 hours.

27. Composition for use according to any one of embodiments 1 to 3, or nanoparticle according to any one of claims 10 to 14, wherein at least one adjuvant is administered separately from the composition or nanoparticle, preferably wherein the at least one adjuvant is administered before, concomitantly or after the administration of the composition or nanoparticle.

28. Composition for use according to any one of embodiments 1 to 3, or 27, or nanoparticle according to any one of claims 10 to 14, or 27, wherein at least one adjuvant is selected from the group consisting an anti-inflammatory agent, an immuno-stimulating agent, and a CpG oligodeoxynucleotide.

29. Composition comprising at least one of the nanoparticles according to any one of embodiment 13 to 28.

30. Method for preparing a composition according to embodiment 29, the method comprising the steps of:
    a) providing a solution or emulsion of the polymer selected from the group consisting of PLGA, PLA, PCL and poly(meth)acrylates, or a lipid in a solvent;
    b) mixing the solution or emulsion of step a) with a solution or emulsion of the at least one adjuvant;
    c) optionally homogenizing the resulting solution or emulsion of step b); and
    d) optionally at least partly removing the solvent.

31. Method according to embodiment 30, wherein the solvent comprises or is an organic solvent; preferably wherein the solvent is selected from the group consisting of ketones, esters, ethers, alcohols, and mixtures thereof; further preferably wherein the solvent is a mixture of ethyl acetate and acetone.

32. Composition as defined in any one of embodiments 1 to 9.

33. Composition for use according to any one of embodiments 1 to 9, or nanoparticle according to any one of embodiments 10 to 24, wherein at least two different adjuvants are present, preferably at least an anti-inflammatory agent and a lipopolysaccharide in combination.

34. Composition for use according to any one of embodiments 1 to 9, or nanoparticle according to any one of embodiments 10 to 24, wherein the nanoparticles consist of ammonio alkyl methacrylate copolymers, preferably an Eudragit® grade, in particular Eudragit® RL and/or Eudragit® RS, and wherein the nanoparticles are free of other materials, preferably for use in the treatment of cancer.

35. Composition for use according to any one of embodiments 1 to 9 for the treatment of cancer, comprising a combination of LPS, nanoparticles and at least one further adjuvant selected from an anti-inflammatory agent (preferably an NSAID), an immuno-stimulating agent, and a CpG oligodeoxynucleotide.

The invention claimed is:

1. A method for treatment of cancerous cells, the method comprising:
    administering a composition to a subject in need thereof, wherein the composition comprises a nanoparticle consisting of a therapeutic agent and at least one adjuvant;
    wherein the therapeutic agent consists of at least one ammonio methacrylate copolymer;
    wherein the at least one adjuvant is selected from the group consisting of an anti-inflammatory agent, an immune-stimulating agent, a CpG oligodeoxynucleotide, and a lipopolysaccharide;
    wherein the at least one ammonio methacrylate copolymer induces one or more of:
        apoptosis in the cancerous cells;
        TNF-α, IL-6, IL-1β, IL-12 and/or IFN-γ at a toxic level; and
        NF-κB activation; and
    wherein the composition comprises no further therapeutic agent or adjuvant for the treatment of cancer.

2. The method according to claim 1, wherein the at least one adjuvant is an anti-inflammatory agent.

3. The method according to claim 2, wherein the anti-inflammatory agent is a nonsteroidal anti-inflammatory drug.

4. The method according to claim 3, wherein the nonsteroidal anti-inflammatory drug is at least one selected from the group consisting of a COX-1 inhibitor, a COX-2 inhibitor, aspirin, choline and magnesium salicylate, choline salicylate, celecoxib, diclofenac potassium, diclofenac sodium, diclofenac sodium with misoprostol, diflunisal, etodolac, fenoprofen calcium, flurbiprofen, ibuprofen, indomethacin, ketoprofen, magnesium salicylate, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium and valdecoxib.

5. The method according to claim 1, wherein the at least one adjuvant is an immuno-stimulating agent.

6. The method according to claim 5, wherein the immuno-stimulating agent is at least one selected from the group consisting of a surface active compound and an oil-in-water emulsion of the surface active compound.

7. The method according to claim 1, wherein the at least one adjuvant is a CpG oligodeoxynucleotide, and wherein the CpG oligodeoxynucleotide has a sequence which is at least 90% identical to SEQ ID NO: 1.

8. The method according to claim 1, wherein the at least one adjuvant is a lipopolysaccharide.

SEQUENCE LISTING

<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: CpG oligodeoxynucleotide

<400> SEQUENCE: 1
tcgtcgtttt cggcgcgcgc cg                                    22

9. The method according to claim 1, wherein the at least one adjuvant is released in-vitro in an amount of about 20% to about 60% after 1 hour, in an amount of about 25% to about 80% after 2 hours, and in an amount of about 30% to about 90% after 4 hours.

10. The method according to claim 1, wherein the composition is prepared by:
a) providing a solution or emulsion of the ammonio methacrylate copolymer in a solvent;
b) mixing the solution or emulsion of a) with a solution or emulsion of the at least one adjuvant;
c) optionally, homogenizing the resulting solution or emulsion of b); and
d) optionally, at least partly removing the solvent(s).

11. The method according to claim 1, wherein the cancerous cells are selected from the group consisting of breast cancer, gastric carcinoma, bladder cancer, colorectal cancer, pancreatic cancer, colon cancer, lung cancer, prostate cancer, glioma, and melanoma.

12. The method according to claim 1, wherein the ammonio methacrylate copolymer is an ammonio alkyl methacrylate copolymer having from 0.1 to 0.2 molar parts of ammonio alkyl methacrylate monomer per 3 molar parts alkyl acrylate and/or alkyl methacrylate monomers.

13. The method according to claim 1, wherein the at least one adjuvant comprises a CpG oligodeoxynucleotide.

14. A method for treatment of cancerous cells, the method comprising:
administering a nanoparticle consisting of a therapeutic agent and at least one adjuvant to a subject in need thereof, wherein the therapeutic agent consists of at least one ammonio methacrylate copolymer;
wherein the at least one adjuvant is selected from the group consisting of an anti-inflammatory agent, an immune-stimulating agent, a CpG oligodeoxynucleotide, and a lipopolysaccharide;
wherein the at least one ammonio methacrylate copolymer induces one or more of:
apoptosis in the cancerous cells;
TNF-$\alpha$, IL-6, IL-1$\beta$, IL-12, and/or IFN-$\gamma$ at a toxic level; and
NF-$\kappa$B activation; and
wherein no further therapeutic agent or adjuvant is administered for the treatment of cancer.

15. The method according to claim 14, wherein the at least one adjuvant is released in vitro in an amount of about 20% to about 60% after 1 hour, in an amount of about 25% to about 80% after 2 hours, and in an amount of about 30% to about 90% after 4 hours.

16. A method for treatment of cancerous cells, the method comprising:
administering a composition to a subject in need thereof, wherein the composition consists of at least one ammonio methacrylate copolymer and a solvent;
wherein the at least one ammonio methacrylate copolymer induces one or more of:
apoptosis in the cancerous cells;
TNF-$\alpha$, IL-6, IL-1$\beta$, IL-12, and/or IFN-$\gamma$ at a toxic level; and
NF-$\kappa$B activation.

* * * * *